United States Patent [19]
Berliner et al.

[11] Patent Number: 5,969,168
[45] Date of Patent: *Oct. 19, 1999

[54] ANDROSTANES FOR INDUCING HYPOTHALAMIC EFFECTS

[75] Inventors: David L. Berliner, Atherton, Calif.; Nathan W. Adams; Clive L. Jennings-White, both of Salt Lake City, Utah

[73] Assignee: Pherin Corporation, Menlo Park, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/316,435

[22] Filed: Sep. 29, 1994

Related U.S. Application Data

[63] Continuation-in-part of application No. 08/127,908, Sep. 28, 1993, abandoned, which is a continuation-in-part of application No. 07/903,604, Jun. 24, 1992, abandoned, which is a continuation-in-part of application No. 07/708,936, May 31, 1991, abandoned, which is a continuation-in-part of application No. 07/638,185, Jan. 7, 1991, abandoned.

[51] Int. Cl.$^6$ ................................. C07J 3/00; C07J 1/00
[52] U.S. Cl. .................. 552/611; 552/632; 552/633; 552/636; 552/638; 552/640
[58] Field of Search .................. 552/530, 610, 552/611, 632, 633, 636, 638, 640, 641, 642, 643, 646, 647, 649

[56] References Cited

U.S. PATENT DOCUMENTS

| | | | |
|---|---|---|---|
| 2,846,451 | 8/1958 | Sondheimer | 260/397.3 |
| 3,681,490 | 8/1972 | Melrose et al. | |
| 3,960,841 | 6/1976 | Engel et al. | |
| 4,071,624 | 1/1978 | Grunwell et al. | |
| 4,071,625 | 1/1978 | Grunwell et al. | |
| 4,075,288 | 2/1978 | Marx et al. | |
| 4,087,524 | 5/1978 | Grunwell et al. | |
| 4,133,811 | 1/1979 | Varma | 260/239.55 R |
| 4,139,617 | 2/1979 | Grunwell et al. | |
| 4,239,681 | 12/1980 | Grunwell et al. | |
| 4,330,538 | 5/1982 | Itil et al. | |
| 4,349,474 | 9/1982 | Chinn | 260/239.55 C |
| 4,425,339 | 1/1984 | Pitchford | |
| 4,835,147 | 5/1989 | Roberts | |
| 4,863,911 | 9/1989 | Anderson et al. | |
| 5,155,045 | 10/1992 | Cutler et al. | 436/65 |
| 5,272,134 | 12/1993 | Berliner | |

FOREIGN PATENT DOCUMENTS

| | | |
|---|---|---|
| 0 562 843 A2 | 9/1993 | European Pat. Off. |
| 2631915 | 7/1975 | Germany ............. C07J 1/00 |
| 1175219 | 12/1969 | United Kingdom . |
| WO 93/10141 | 5/1993 | WIPO . |
| WO 94/28904 | 12/1994 | WIPO . |

OTHER PUBLICATIONS

Romer, et al, *Steroids*, 51(5–6) pp. 577–81 (1988).
Matsui, et al, *J. Org Chem*, 35(3) pp. 561–4 (1970).
Garcia–Velasco et al., *Aesth. Plast. Surg.* 19:451–454 (1995).
Axel, *Scientific American*, Oct. 1995 pp. 154–159.
M. Adamczyk, et al., "A New Procedure for the One–Carbon Homologation of Ketones to α–Hydroxy Aldehydes", The Journal of Organic Chemistry, vol. 49, No. 8, Apr. 20, 1984, pp. 1378–1382.
John F. Templeton, et al., "Proton Magnetic Resonance Spectra", Steroids, vol. 41, No.4, Apr. 1983, pp. 484–491.
E. Ghera, et al., "Zinc–induced Free–radical Reactions of Aromatic α–Halogenoketones with Terminal Olefins", J.C.S. Chem. Comm., 1973, pp. 858–859.
B.S. Macdonald, et al., "The Identification of 17–α–Hydroxy–17–Methyl–1, 4–Androstadien–3–one as a Metabolite of the Anabolic Steroid Drug in Man", Steroids an International Journal, vol. 18, No. 6, Dec. 1971, pp. 753–766.
T.L. Johnson, "Chemical Abstracts", 42–Steroids, vol. 62, 1965, pp. 11871–11872.
G. Ortar, et al., "Oxidation of 17–Methylene Steroids by Thallium (III) and Mercury (II) Acetates", Steroids, vol. 17, No. 2, Feb. 1976.

*Primary Examiner*—Jose' G. Dees
*Assistant Examiner*—Barbara Badio
*Attorney, Agent, or Firm*—Heller Ehrman White & McAuliffe

[57] ABSTRACT

The invention relates to novel, androstane steroids which are the ligand semiochemicals which bind to neuroepithelial receptors. The steroids are useful as ligands to neuroepithelial receptors in the human vomeronasal gland to stimulate autonomic and hypothalamic activity.

7 Claims, 25 Drawing Sheets

5,969,168

ANDROSTANES FOR INDUCING HYPOTHALAMIC EFFECTS

BACKGROUND

Cross-Reference to Related Applications

This application is a continuation-in-part of U.S. Ser. No. 08/127,908, filed Sep. 28, 1993, now abandoned, which is a continuation-in-part of U.S. application Ser. No. 07/903,604, filed Jun. 24, 1992, now abandoned, which is a continuation-in-part of U.S. application Ser. No. 07/708,936, filed May 31, 1991, now abandoned, which is a continuation-in-part of U.S. application Ser. No. 07/638,185, filed Jan. 7, 1991, now abandoned.

The application also relates to another continuation-in-part of U.S. patent application Ser. No. 07/903,604, U.S. patent application Ser. No. 08/077,359, filed Jun. 15, 1993, and to commonly assigned, co-pending U.S. patent application Ser. No. 07/903,525, filed Jun. 24, 1992 (a continuation-in-part of U.S. application Ser. No. 07/707,862, filed May 31, 1991, which in turn is a continuation-in-part of U.S. application Ser. No. 07/638,743, filed Jan. 7, 1991, now abandoned) entitled "Estrene Steroids as Neurochemical Initiators of Change in Human Hypothalamic Function and Related Pharmaceutical Compositions and Methods"; and to the commonly assigned, co-pending continuation-in-part of application Ser. No. 07/903,525, U.S. patent application Ser. No. 08/077,140, filed Jun. 15, 1993. The aforementioned U.S. patent applications are each incorporated herein by reference.

Finally, this application may relate to a co-pending U.S. patent application entitled "Fragrance Compositions Containing Human Pheromones", filed Mar. 24, 1992, U.S. Ser. No. 07/856,435.

TECHNICAL FIELD

This invention relates generally to pharmaceutical compositions and methods for effectuating change in human hypothalamic function, thereby altering certain behavior and physiology mediated by the hypothalamus of individuals. More particularly, the invention relates to the use of certain Androstene steroids as neurochemical effectuators of physiology and behavior.

DESCRIPTION OF THE RELATED ART

The present invention relates to certain compounds, namely Androstane steroids, particularly Androstene steroids and related compounds as will be described herein, and methods of using these compounds as human semiochemicals in order to alter hypothalamic function, thereby affecting certain consequent behavior and physiology, e.g., the reduction of anxiety. Androstane steroids are typified by testosterone and they are characterized by a four ring steroidal structure, a methylation at the 13-position and at the 10-position. Androstenes are a subset of Androstanes and have at least one double bond. Ohloff, G. et al. (*Helv. Chim. Acta* (1983) 66:192–217), which is incorporated herein by reference, have shown that several members of this group of steroids have an odor which varies with different isomeric, diastereomeric, and enantiomeric forms. Some members of this group have been reported to act as a pheromone in some mammalian species—for instance, 5α-androst-16-en-3-one and 5α-androst-16-en-3α-ol in pigs (Melrose, D. R., et al., *Br. vet. J.* (1971) 127:497–502). These 16-Androstenes produced by the boar induce mating behavior in estrus sows (Claus, et al., *Experimentia* (1979) 35:1674–1675).

Some studies have noted that, in some species, various characteristics of certain 16-Androstenes (including 5α-Androst-16-en-3α-ol and 5α-Androst-16-en-3-one), such as concentration, metabolism, and localization, are sexually dimorphic (Brooksbank et al., *J. Endocr.* (1972) 52: 239–251; Claus, et al., *J. Endocr.* (1976) 68:483–484; Kwan, et al., *Med. Sci. Res.* (1987) 15:1443–1444). For instance, 5α-Androst-16-en-3α-ol and 5α-Androst-16-en-3-one, as well as Androsta-4,16-dien-3-one, have been found at different concentrations in the peripheral blood, saliva and axillary secretions of men and of women (Kwan, T. K., et al., *Med. Sci. Res.* (1987) 15:1443–1444), and their function as a human pheromone, to the extent of affecting choice and judgement, has been suggested (Id.; see also Gower, et al., "The Significance of Odorous Steroids in Axillary Odour", In, *Perfumery*, pp. 68–72, Van Toller and Dodd, Eds., Chapman and Hall, 1988); Kirk-Smith, D. A., et al., *Res. Comm. Psychol. Psychiat. Behav.* (1978) 3:379). Androstenol (5α-androst-16-en-3α-ol) has been claimed to exhibit a pheromone-like activity in a commercial men's cologne and women's perfume (Andron™ for men and Andron™ for women by Jōvan). Japanese Kokai No. 2295916, refers to perfume compositions containing androstenol and/or its analogues. 5α-Androstadien-3β-ol (and perhaps the 3α-ol) has also been identified in human axillary secretion (Gower, et al., Supra at 57–60. On the other hand, there is little agreement in the literature as to whether or not any putative pheromone actually plays any role in the sexual or reproductive behavior of mammals, particularly of humans. See: Beauchamp, G. K., et al., "The Pheromone Concept in Mammalian Chemical Communication: A Critique", In: *Mammalian Olfaction, Reproductive Processes and Behavior*, Doty, R. L., Ed., Academic Press, 1976). See also: Gower, et al., supra at 68–73.

An embodiment of the subject invention concerns the non-systemic, nasal administration of certain Androstane and Androstene steroids to affect a specific behavioral or physiological response in human subjects, e.g., a reduction of negative affect, mood, and character traits. In particular, nasal administration provides for contacting neurochemical receptors of a heretofore poorly understood neuroendocrine structure, commonly known as the vomeronasal organ ("VNO"; also known as "Jacobson's organ"), with one or more steroid(s) or with compositions containing the steroid (s). This organ is accessed through the nostrils of most higher animals—from snakes to humans, and has been associated, inter alia, with pheromone reception in certain species (see generally Muller-Schwarze & Silverstein, *Chemical Signals*, Plenum Press, New York (1980)). The axons of the neuroepithelia of the vomeronasal organ, located supra palatinal, form the vomeronasal nerve and have direct synaptic connection to the accessory olfactory bulb and indirect input from there to the cortico-medial amygdaloid basal forebrain and hypothalamic nuclei of the brain. The distal axons of terminalis nerve neurons may also serve as neurochemical receptors in the VNO. Stensaas, L. J., et al., *J. Steroid Biochem. and Molec. Biol.* (1991) 39:553. This nerve has direct synaptic connection with the hypothalamus.

Johnson, A. et al. (*J. Otolaryngology* (1985) 14:71–79) report evidence for the presence of the vomeronasal organ in most adult humans, but conclude that the organ is probably non-functional. Contravening results which suggest that the VNO is a functional chemosensory receptor are reported by Stensaas, L., et al., supra; and by Moran, D. T., et al., Garcia-Velasco, J. and M. Mondragon; Monti-Bloch, L. and B. Grosser all in *J. Steroid Biochem. and Molec. Biol.* (1991) 39.

It is apparent that it would be desirable to identify and synthesize human semiochemicals and pheromones and to develop pharmaceutical compositions and methods of use to influence hypothalamic function. This invention relates to the unexpected discovery that, when nasally administered to human subjects, certain neurochemical ligands, particularly Androstane steroids, more particularly Androstene steroids and related compounds, or pharmaceutical compositions containing Androstanes, Androstenes or related compounds, specifically bind to chemoreceptors of certain nasal neuroepithelial cells and this binding generates a series of neurophysiological responses resulting in an alteration of hypothalamic function of an individual. When properly administered, the effect of certain of these compounds on the hypothalamus affects the function of the autonomic nervous system and a variety of behavioral-or physiological phenomena which include, but are not limited to the following: anxiety, premenstrual stress, fear, aggression, hunger, blood pressure, and other behavioral and physiological functions normally regulated by the hypothalamus. Otto Appenzeller. The Autonomic Nervous System. An introduction of basic and clinical concepts (1990); Korner, P. I. Central nervous control of autonomic cardiovascular function, and Levy, N. M. and Martin, P. J. Neural control of the heart, both in Handbook of Physiology; Section 2: Cardiovascular System—the heart, Vol I, Washington D.C., 1979, American Physiological Society; Fishman, A. P., et al. editors, Handbook of Physiology. Section 3: Respiratory System. Vol. II. Control of breathing. Bethesda Md. 1986. American Physiological Society.

In some instances a single Androstane steroid, or related compound, is administered, in some instances combinations of Androstane steroids and/or related compounds are administered.

SUMMARY OF THE INVENTION

Accordingly, it is an object of this invention to provide novel steroid compounds which are pheromones and are suitable for nasal administration in an individual.

It is another object of this invention to provide compounds useful for altering hypothalamic function which have the following advantages: 1) administration directly to the chemoreceptors in the nasal passage and the vomeronasal organ, without pills or needles—i.e., non-invasively; 2) a mode of drug action through the nervous system and not through the circulatory system—thus brain function can be affected without consideration of the blood-brain barrier; 3) a direct means of affecting the hypothalamus—there is only one synaptic junction between pheromone receptors and the hypothalamus; and, 4) providing a highly specific drug effect, thereby greatly reducing the potential for undesirable side-effects—this because sensory nerves are addressed to a specific location in the brain.

Additional objects, advantages and novel features of the invention will be set forth in part in the description which follows, and in part will become apparent to those skilled in the art upon examination of the following, or may be learned by practice of the invention.

Objects of this invention are achieved by providing a novel steroid compound suitable for nasal administration in an individual. The compound is an androstane steroid with the formula:

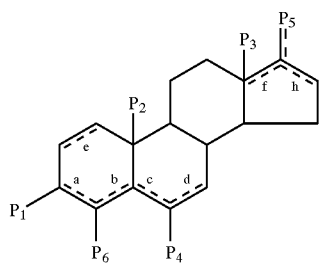

wherein $P_1$ is selected from the group consisting of oxo, α-(β-) hydroxy, α-(β-) acetoxy, α-(β-) propionoxy, α-(β-) methoxy, α-(β-) lower acyloxy, α-(β-) lower alkyloxy, and α-(β-) benzoyloxy; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is absent or is selected from the group consisting of hydrogen, methyl, hydroxymethyl, acyloxymethyl, alkoxymethyl, lower alkyl, hydroxyalkyl, acyloxyalkyl, and alkoxylalkyl; $P_4$ is selected from the group consisting of hydrogen, oxo, halo, hydroxy, alkoxy, and acyloxy; $P_5$ represents one or 2 substituents, wherein $P_5$ is one or two hydrogen or methyl groups, methylene, or one or two halo atoms; $P_6$ is hydrogen or halo; and "a", "b", "c", "d", "e", "f", and "h" are alternative sites for optional double bonds; with provisos that:

I: if "f" and "h" are absent and $P_2$ is methyl, $P_5$ cannot be two hydrogen atoms;

II: if "h" is present; $P_3$ is a methyl group, $P_5$ is hydrogen, then (a) $P_1$ cannot be hydrogen, if "e" and "a" are absent and "b" is present; or (b) "d" cannot be present if $P_1$ is oxo, "b" is present, and "e" is absent;

(c) $P_4$ cannot be hydrogen if "c" and "d" are absent, "b" is present, $P_1$ is oxo, and $P_2$ is methyl or hydroxymethyl;

(d) $P_4$ cannot be oxo if "e", "c" and "d" are absent, "b" is present, and $P_1$ is oxo;

(e) $P_4$ and $P_6$ cannot be hydrogen if $P_1$ is oxo, "e" and "b" are present and "c" and "d" are absent;

(f) $P_4$ cannot be hydrogen if $P_1$ is β-hydroxy, "c" is present and "a", "b", "e" and "d" are absent;

(g) $P_4$ cannot be hydrogen if $P_1$ is methoxy, "a" and "c" are present and "e", "a" and "d" are absent.

III: $P_4$ and $P_6$ cannot be hydrogen if $P_1$ is oxo, "b" is present, $P_5$ is methylene and "a", "e", "c" and "d" are absent;

IV: $P_4$ and $P_6$ cannot be hydrogen if $P_1$ is β-hydroxy, "c" is present, $P_5$ is methylene, and "a", "e", "b" and "d" are absent;

V: $P_4$ and $P_6$ cannot be hydrogen if $P_1$ is oxo; "b" and "f" are present, $P_5$ is methyl and "e", "a", "c", "d" and "h" are absent.

One class of preferred steroids has "b" as a double bond, particularly wherein "h" is also a double bond. Yet another preferred class has $P_2$ as hydroxymethyl, and "c" as a double bond. Another preferred class has "b" as a double bond and $P_5$ as methylene.

By halo, it is meant, F, Cl, Br, or I. The term lower alkyl, lower alkoxy, etc., is meant to encompass carbon chains of 1 to 6 carbon atoms, preferably 1 to 4 carbon atoms.

Other objects of this invention are achieved by providing a method of altering hypothalamic function and/or autonomic function in an individual. A ligand for a chemoreceptor displayed on the surface of a nasal neuroepithelial cell is provided wherein the cell is a part of tissue other than olfactory epithelia; and, the ligand is administered within a nasal passage of the individual such that the ligand binds specifically to the chemoreceptor, resulting in an alteration of hypothalamic function of the individual.

All embodiments of this application relate to and include the functional equivalents of the steroid structures disclosed in these embodiments and to those modified steroids which demonstrate said functional equivalence, whether or not the modified steroids are explicitly disclosed.

DETAILED DESCRIPTION OF THE INVENTION

I. Definitions

Figure 1:
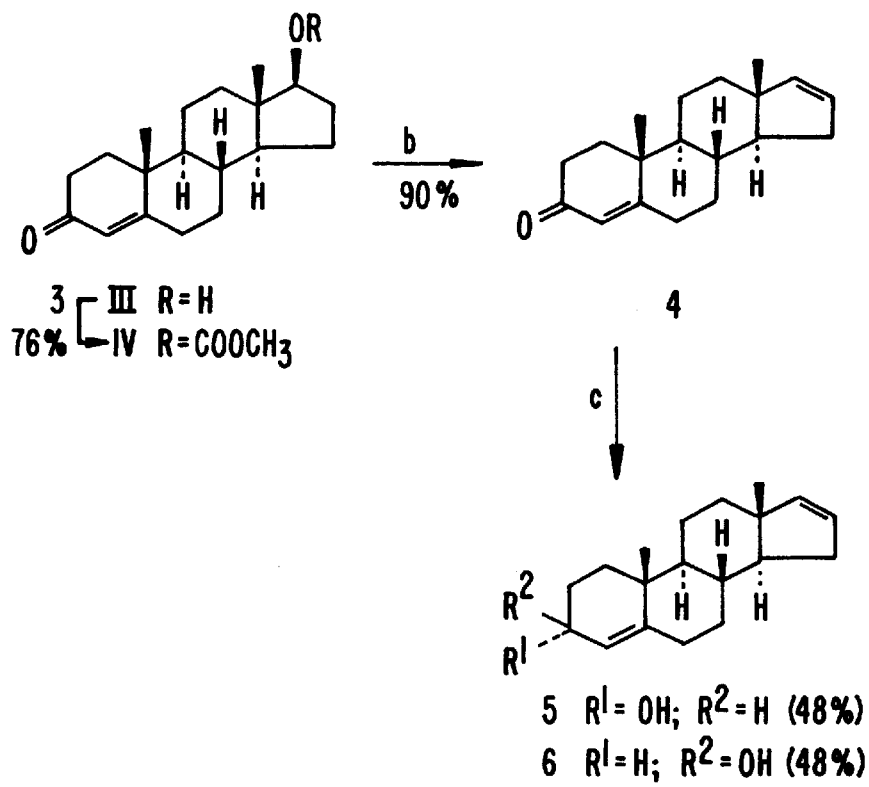
FIG. 1 illustrates the synthesis of Androsta-4,16-dien-3-one, Androsta-4,16-dien-3α-ol, and Androsta-4,16-dien-3β-ol.

An "affect" is a transient feeling state. Typical negative affects are feelings of nervousness, tenseness, shame, anxiousness, irritability, anger, rage, and the like. "Moods" are longer lasting feeling states such as guilt, sadness, hopelessness, worthlessness, remorsefulness, misery, unhappiness and the like. "Character traits" are more permanent aspects of an individual's personality. Typical negative character traits are sensitivity, regretfulness, blameworthiness, stubbornness, resentfulness, bitterness, timidness, laziness and the like.

"Androstane steroids" are aliphatic polycyclic hydrocarbons characterized by a four-ring steroidal structure with a methylation at the 10- and 13-positions. An Androstene is a subset of Androstanes commonly understood to mean that the compound has at least one double bond. Commonly, unless a compound is described as a gonane, it is understood that the compound has an 18-carbon group. However, it is intended herein that 18-Nor-Androstanes are herein regarded as Androstane steroids. Furthermore, all derivatives which have the structural characteristics described above are also referred to generically as Androstane steroids.

A "chemoreceptor" is a receptor molecule displayed on the surface of a "chemosensory" neuroepithelial cell which binds in a stereospecific fashion to a particular ligand or ligands. This specific binding initiates a signal transduction which initiates an afferent nerve impulse. Chemoreceptors are found, inter alia, in taste buds, olfactory epithelium and vomeronasal tissue.

"Estrene steroids", as the term is used herein, are aliphatic polycyclic hydrocarbons with a four-ring steroidal structure, at least one double bond in the A-ring, no methylation at the 10-position and an oxo, hydroxyl or hydroxyl derivative such as an alkoxy, ester, benzoate, cypionate, sulfate or glucuronide, at the 3-position. Derivatives which contain these structural characteristics are also referred to generically as Estrene steroids.

The following structure shows the four-ring steroidal structure common to Androstane and Estrene steroids. In describing the location of groups and substituents, the following numbering system will be employed:

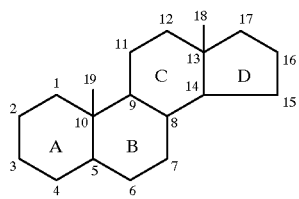

"Sexually dimorphic" refers to a difference in the effect of, or response to, a pharmaceutical agent between males and females of the same species.

An "effective amount" of a drug is a range of quantity and/or concentration which brings about a desired physiological and/or psychological effect when administered to an individual in need of the drug. In the present case, a needy individual is one with a physiological or behavioral trait which is normally regulated by the hypothalamus and wherein it is desirable to affect the function of the hypothalamus or the trait. The effective amount of a given drug may vary depending upon the function to be affected, the desired effect, route of administration, and the like. For example, when the steroid is administered as a solution applied to the facial skin of a subject an effective concentration is from 1 microgram/ml to 100 µg/ml, preferably 10 to 50 µg/ml and most preferably 20 to 30 µg/ml. When the steroid is introduced directly into the VNO an effective amount is about 1 picogram to about 1 nanogram, more preferably about 10 picograms to about 50 picograms. When the steroid is administered to the nasal passage, by ointment, cream or aerosol, or the like, an effective amount is about 100 pg to about 100 micrograms, preferably about 1 ng to about 10 micrograms. It follows that some drugs may be effective when administered by some routes, but not effective when administered by other routes.

The "hypothalamus" is the portion of the diencephalon comprising the ventral wall of the third ventricle below the hypothalamic sulcus and including structures forming the ventricle floor, including the optic chiasma, tuber cinereum, infundibulum, and mammillary bodies. The hypothalamus regulates the autonomic nervous system and controls several physiological and behavioral functions such as the so-called fight and flight responses, sexual motivation, water balance, sugar and fat metabolism, hunger, regulation of body temperature, endocrine secretions, and others. The hypothalamus is also the source of vasopressin which regulates blood pressure, and oxytocin which induces parturition and milk release. All hypothalamic functions are potentially modulatable by the semiochemical therapy described herein.

A "ligand", as used herein, is a molecule which acts as a chemical signal by specifically binding to a receptor molecule displayed on the surface of a receptor cell, thereby initiating a signal transduction across the cell surface. Binding of ligands to chemosensory receptors can be measured. Chemosensory tissue, such as vomeronasal neuroepithelium or olfactory neuroepithelium, contains a multiplicity of neuroreceptors cells, each displaying at least one cell surface receptor. Many of the receptor molecules have identical ligand specificity. Therefore, when the tissue is exposed to a ligand for which it has specificity (for example a exposure of the VNO to a semiochemical) a summated change in cell surface receptor potential can be measured.

As used herein, "lower alkyl" means a branched or unbranched saturated hydrocarbon chain of 1 to 4 carbons, such as, for example, methyl, ethyl, n-propyl, i-butyl and the like. "Alkoxy" as used herein is used in its conventional sense to mean the group —OR wherein R is alkyl as herein defined.

A "pheromone" is a substance that provides chemical means of communication between members of the same species through secretion and nasus reception. In mammals pheromones are usually detected by receptors in the vomeronasal organ of the nose. Commonly, pheromones effect development, reproduction and related behaviors. A "semiochemical" is a more general term which includes pheromones and describes a substance from any source which functions as a chemosensory messenger, binds to a specific neuroepithelial receptor, and induces a physiological or behavioral effect. A "vomeropherin" is a semiochemical whose physiologic effect is mediated through the vameronasal organ.

A picogram (pg) is equal to 0.001 nanograms (ng). A ng is equal to 0.001 micrograms (µg). A µg is equal to 0.001 mg.

II. Modes for Carrying Out the Invention

A. Androstanes useful in the Invention

The invention is directed to a group of certain Androstane steroids. Testosterone (17-hydroxy-Androsta-4-en-3-one) is a typical Androstane.

Androstanes especially suitable for use in the present invention include those where, independently, $P_1$=oxo, α-hydroxy, β-hydroxy; $P_2$=methyl, lower alkyl, hydroxymethyl, hydroxyalkyl; $P_3$=hydrogen or methyl; $P_4$=hydrogen, hydroxy, or oxo; $P_5$=hydrogen or methyl; and there is at least one double bond, usually at the 4- or 16-position.

Preferred Androstanes include Androsta-4,16-dien-3-one ($P_1$=oxo, b,h=double bond, $P_2$, $P_3$=methyl; $P_4$, $P_5$, $P_6$=hydrogen, commercially available from Steraloids, Inc.), Androsta-4,16-dien-3β-ol ($P_1$=β-OH, b,h=double bond, $P_2$, $P_3$=methyl, $P_4$, $P_5$, $P_6$=hydrogen), and 6-keto-Androsta-4,16-diene-3-one ($P_1$=oxo; b,h=double bond, $P_2$, $P_3$=methyl, $P_5$, $P_6$=hydrogen, $P_4$=oxo), synthesis of which are described herein.

A subset of Androstanes within the group are believed to be novel. Syntheses are described herein for the following compounds as designated on the chart: 17-methylene-Androst-4-en-3β-ol (A3/N3), 17-methylene-Androst-4-en-3α-ol (A4/N3), 17-methylene-6-oxo-Androst-4-en-3-one (A6/N3), and 6β-OH-Androsta-4,16-dien-3-one (A11/N1).

Chart 1 includes androstanes to which the invention is directed, but do not limit its scope. The synthesis diagrams that follow depict intermediate and substructure syntheses for the preparation of these androstanes:

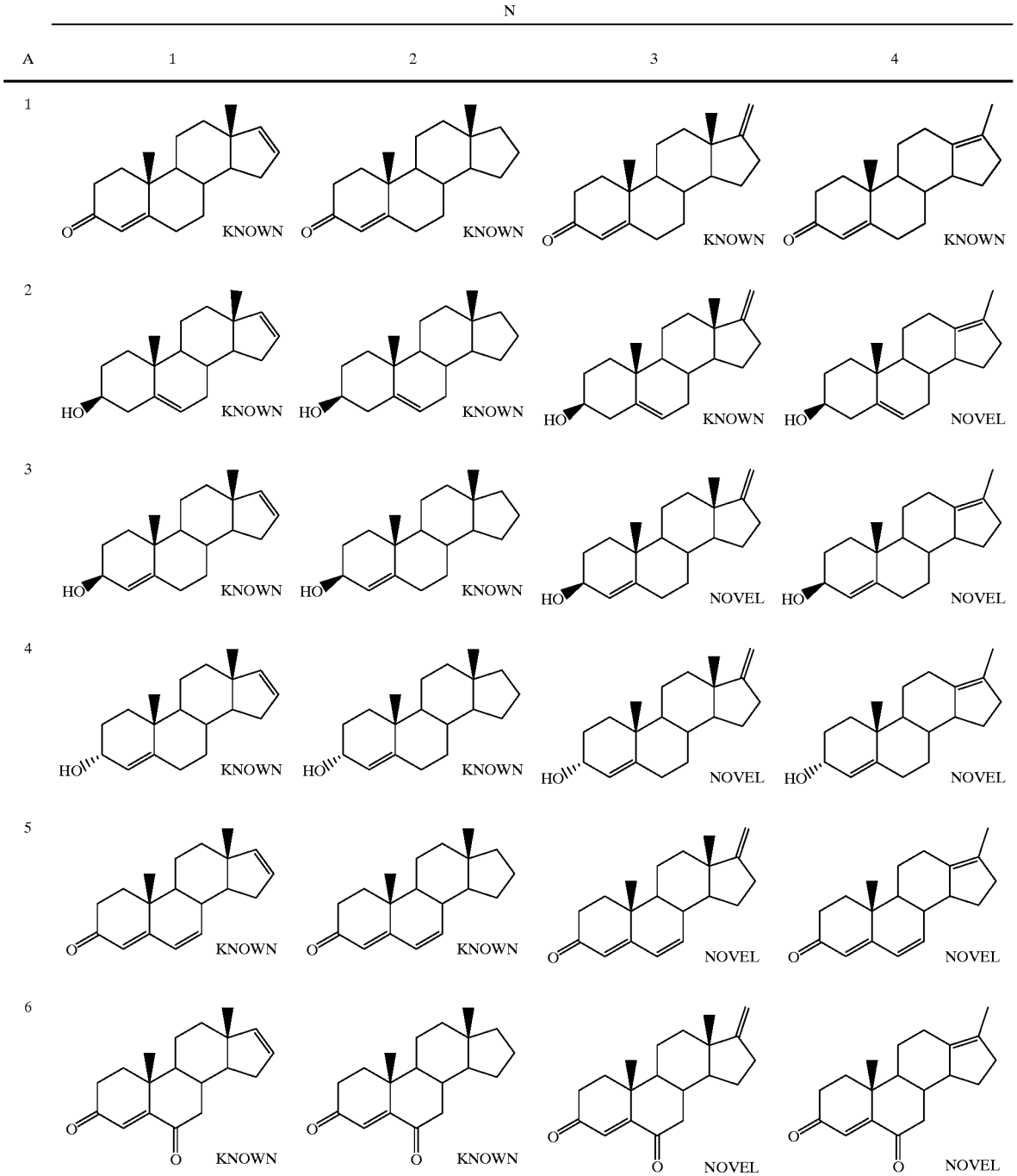

-continued

ANDROSTANES

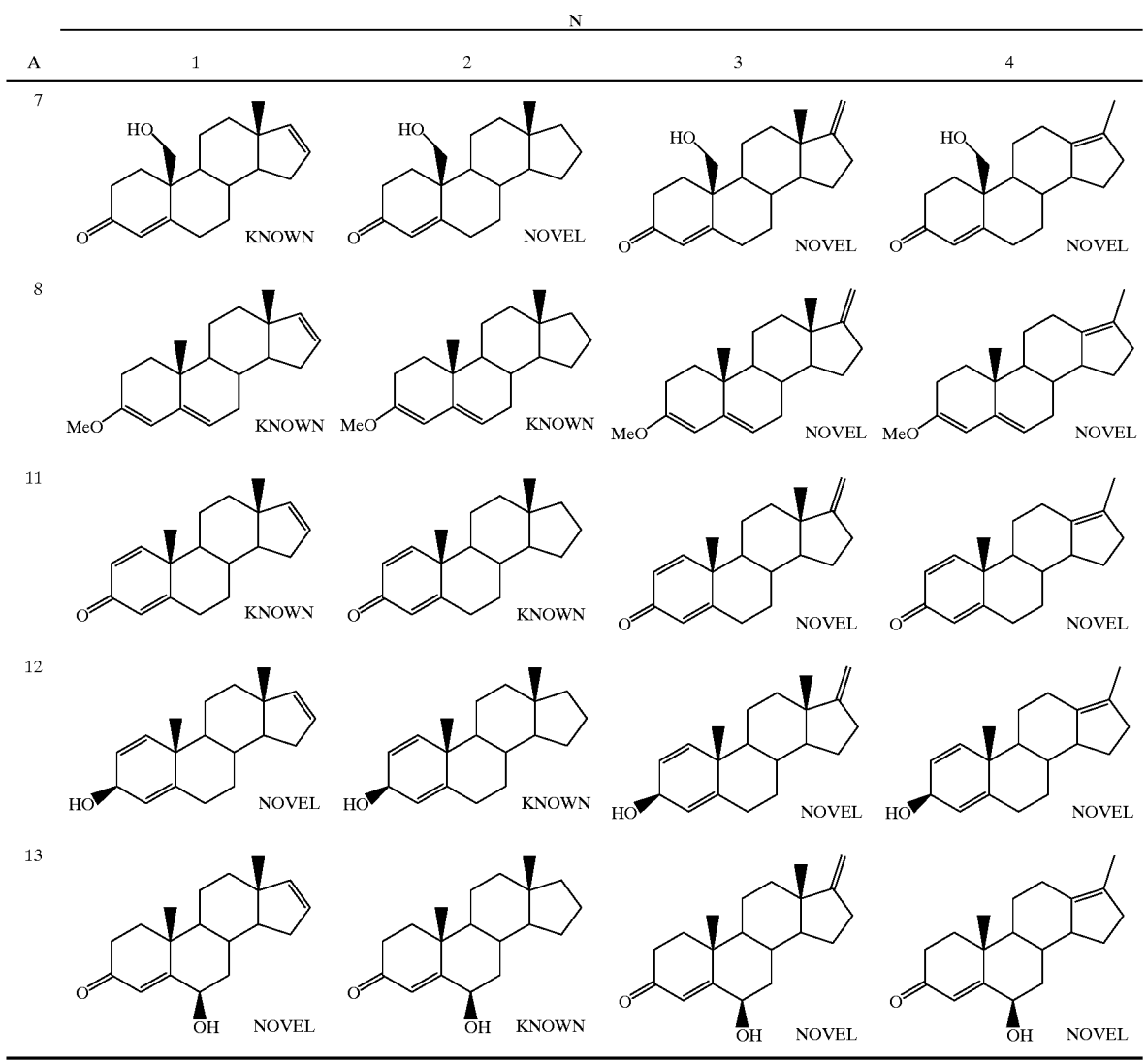

NOVEL ANDROSTANES

17-METHYLENEANDROST-4-EN-3α-OL (A4/N3)

17-METHYLENEANDROST-4-EN-3β-OL (A3/N3)

6β-HYDROXYANDROSTA-4,16-DIEN-3-ONE (A13/N1)

6β-HYDROXY-17-METHYL-18-NORANDROSTA-4,13(17)-DIEN-3-ONE (A13/N4)

ANDROSTA-5,16-DIEN-3β,19-DIOL (19-HYDROXY DERIVATIVE OF A2/N1)

17-METHYLENEANDROST-4-ENE-3,6-DIONE (A6/N3)

17-METHYL-18-NORANDROSTA-4,13(17)-DIEN-3α-OL (A4/N4)

17-METHYL-18-NORANDROSTA-4,13(17)-DIEN-3β-OL (A3/N4)

17β-METHYLANDROST-4-ENE-3,6-DIONE (17β METHYL derivative of A6/N2)

3-METHOXY-17-METHYLENEANDROSTA-3,5-DIENE (A8/N3)

6β-HYDROXY-17-METHYLENEANDROST-4-EN-3-ONE (A13/N3)

17-METHYLENEANDROSTA-1,4-DIEN-3-ONE (A11/N3)

6β-HYDROXYANDROSTA-1,4,16-TRIEN-3-ONE (6β-HYDROXY derivative of A11/N1)

6β-HYDROXY-17-METHYLENEANDROSTA-1,4-DIEN-3-ONE (6β-HYDROXY derivative of A11/N3)

17β-METHYLANDROST-4-EN-3α-OL (17β-METHYL derivative of A4/N2)

17β-METHYLANDROST-4-EN-3β-OL (17β-METHYL derivative of A3/N2)

3-METHOXY-17-METHYL-18-NORANDROSTA-3,5,13(17)-TRIENE (A8/N4)

SUBSTRUCTURE SYNTHESES

Referring to the preceding table, the following are exemplary syntheses for intermediates in a given row (A1 through A11) or column (N1 through N4).

Type A
A1:
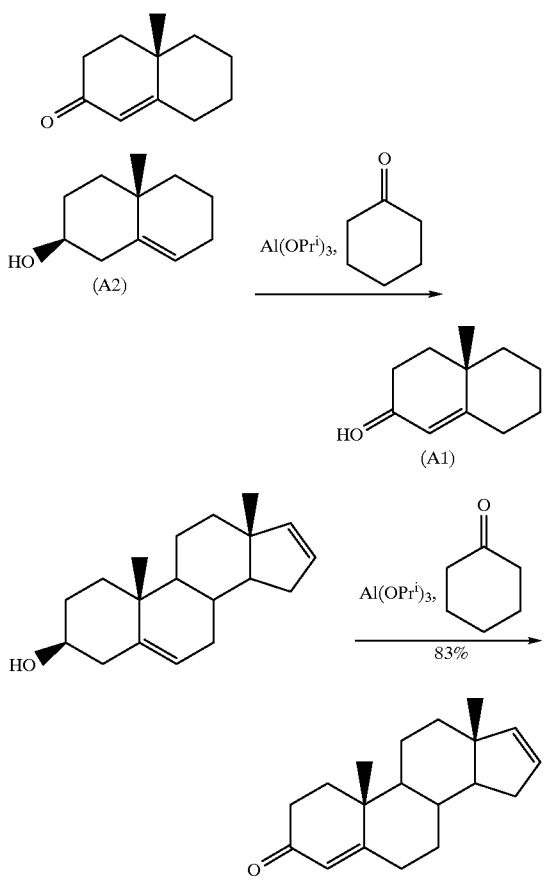
A2:
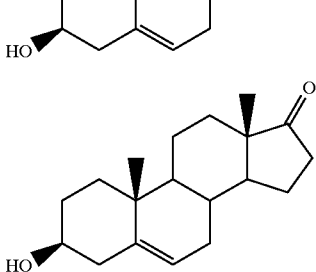
This is a commercially available substructure, for example, DEHYDRO EPI ANDROSTERONE.
A3:
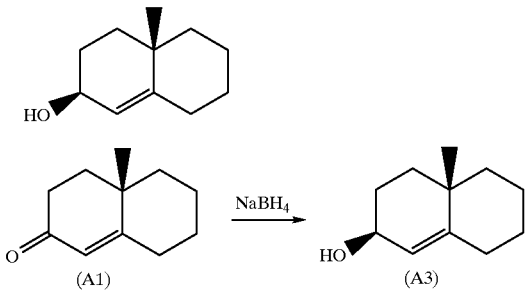
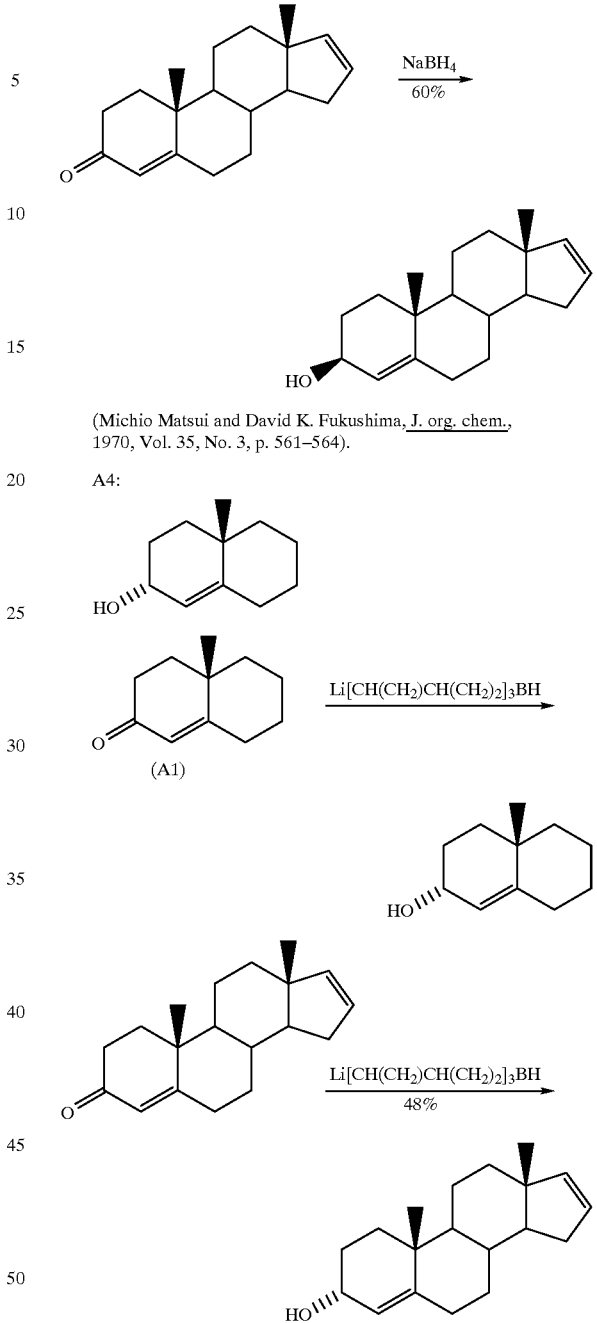
(Michio Matsui and David K. Fukushima, J. org. chem., 1970, Vol. 35, No. 3, p. 561–564).
A4:
Ohloff, G. et al. (Helv. Chim. Acta (1983) 66: 192-217).
A5:
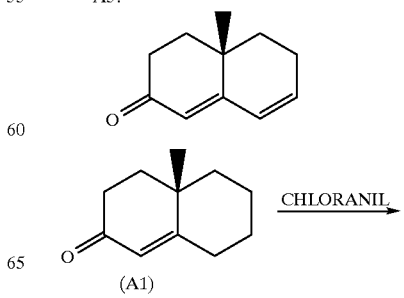

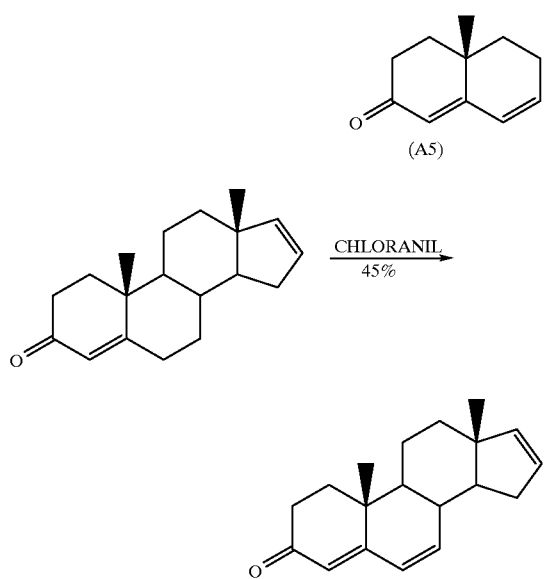
German Off. 2,631,915.
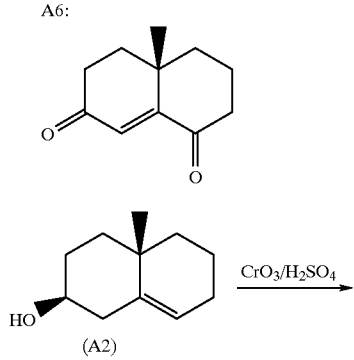
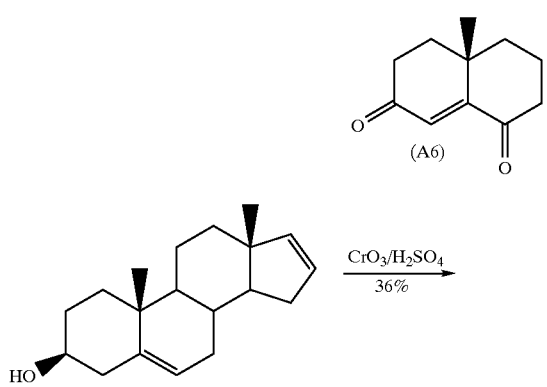
J. Römer, H. Wagner, and W. Sihade, steroids, 1988, 51/5–6, p. 577–581).
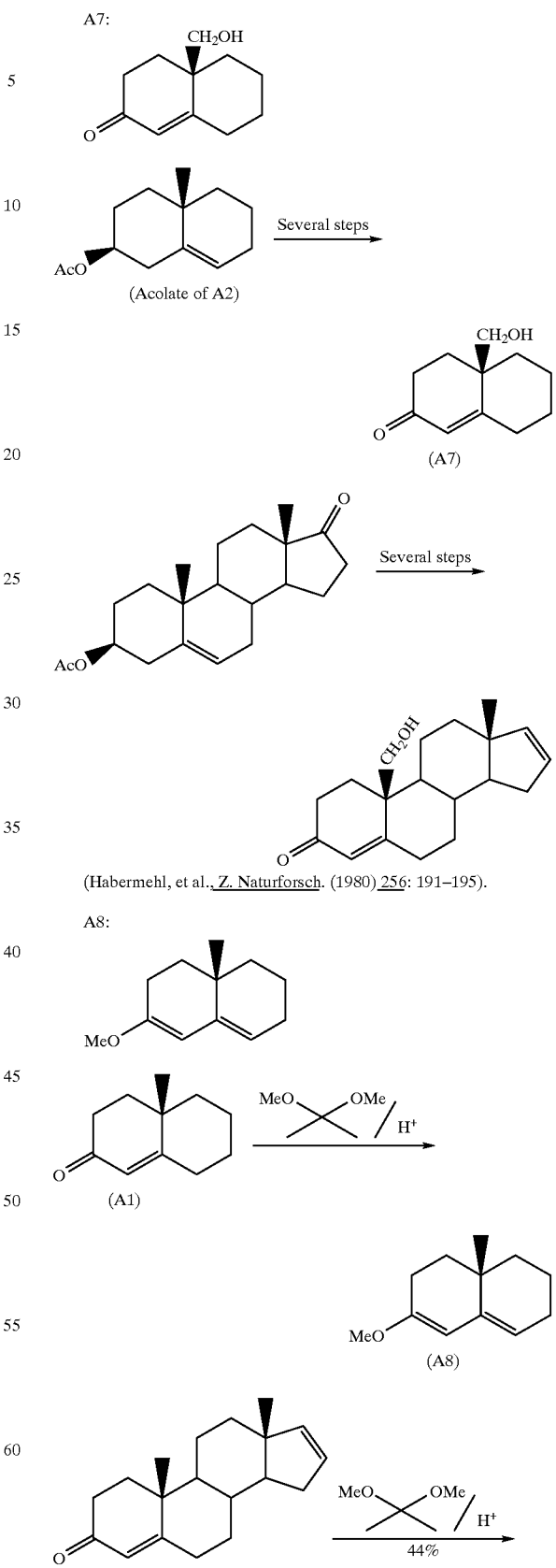
(Habermehl, et al., Z. Naturforsch. (1980) 256: 191–195).

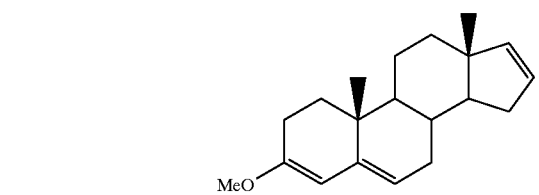
SEE EXAMPLE 15
A9:
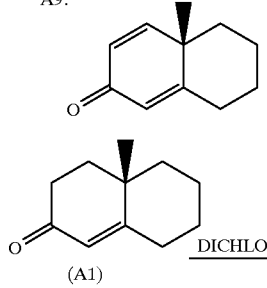
(A1) → DICHLORODICYANO BENZOQUINONE →
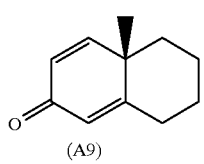
(A9)
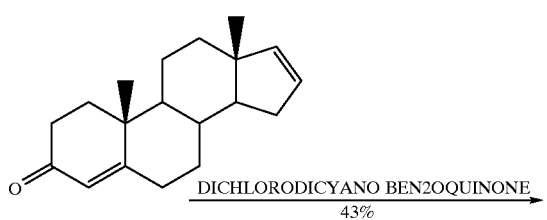
→ DICHLORODICYANO BENZOQUINONE, 43% →
Ohloff, G. et al. (Helv. chim. Acta (1983) 66: 192–217).
A10:
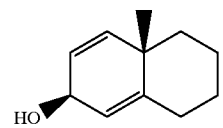
(A9) → LiAlH₄ → 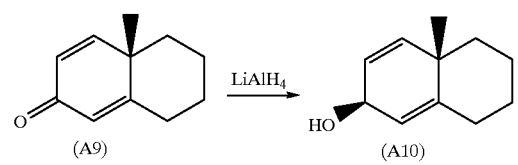 (A10)
→ LiAlH₄, 30% →
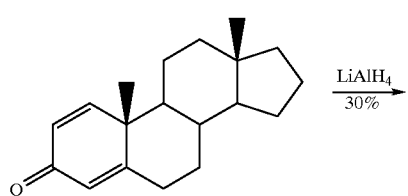
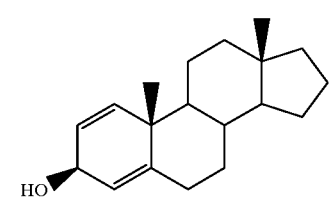
V. I. Mel'nikova and K. K. Pivnitskii, Zhurnal Organickeskoi Khisnii, 1972, Vol. 8, No. 1, pp. 68–74).
A11:
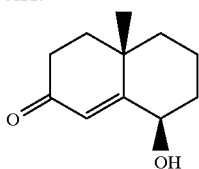
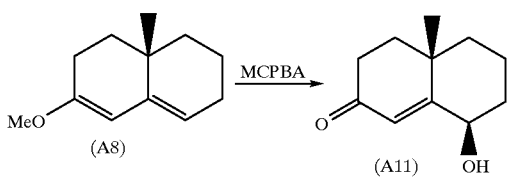
(A8) → MCPBA → (A11)
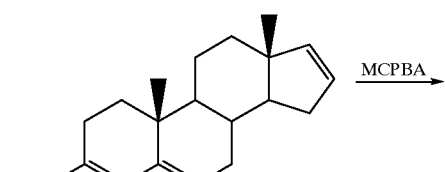 → MCPBA →
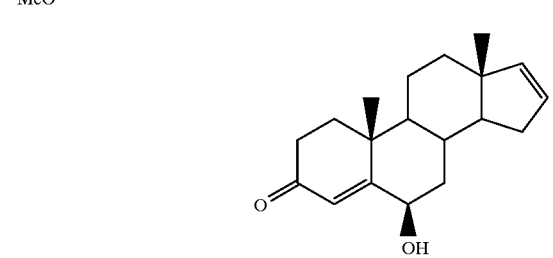
SEE EXAMPLE 19
Type N
N1:
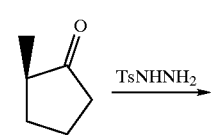 → TsNHNH₂ →
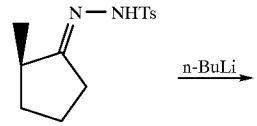 → n-BuLi →

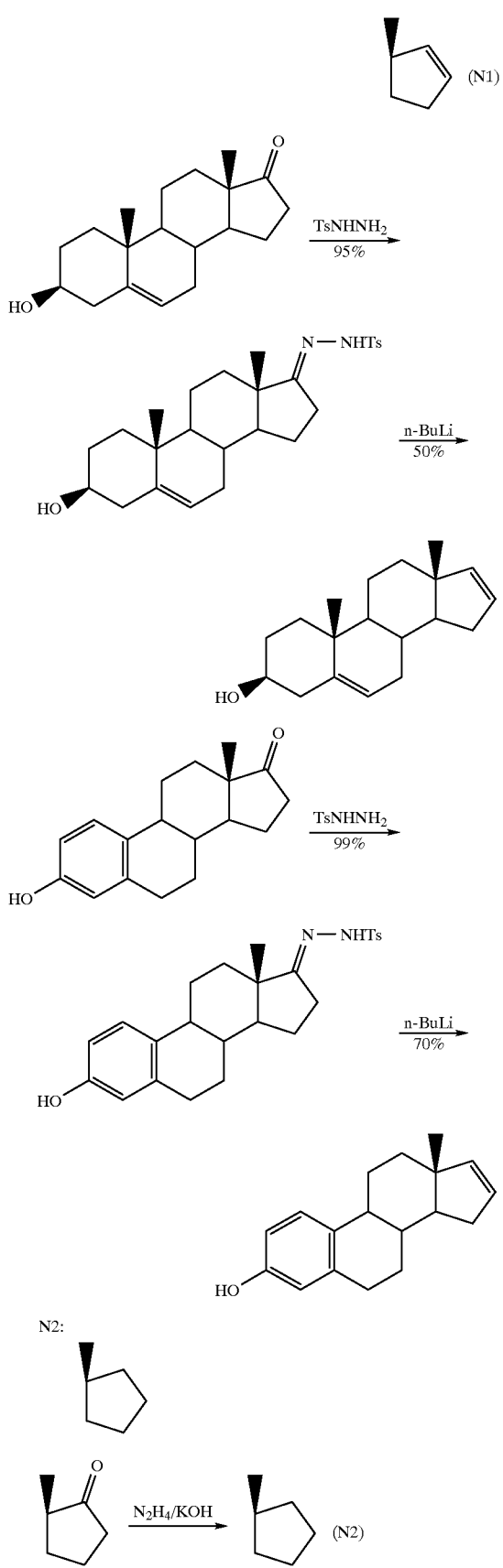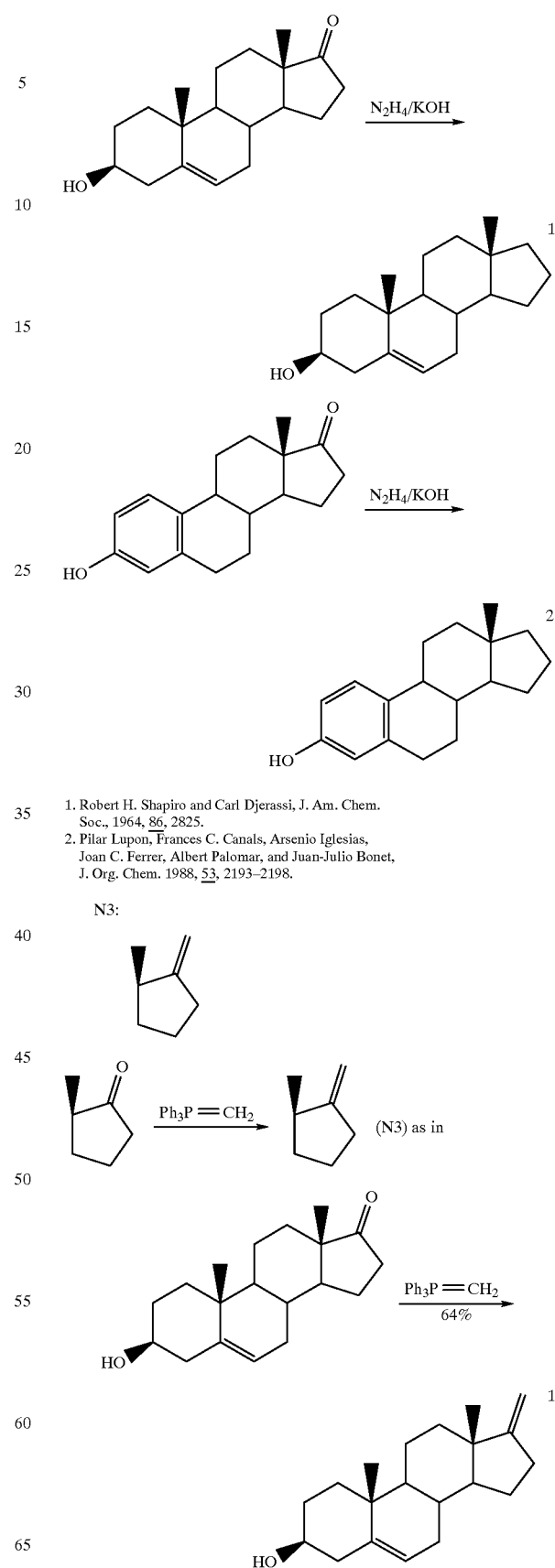
1. Robert H. Shapiro and Carl Djerassi, J. Am. Chem. Soc., 1964, 86, 2825.
2. Pilar Lupon, Frances C. Canals, Arsenio Iglesias, Joan C. Ferrer, Albert Palomar, and Juan-Julio Bonet, J. Org. Chem. 1988, 53, 2193–2198.
N3:
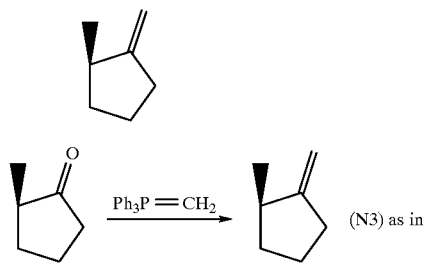

-continued

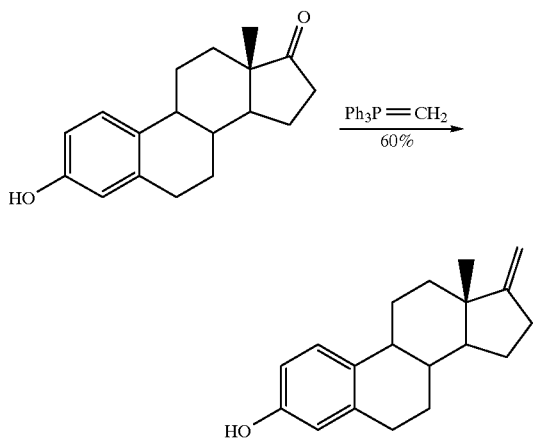

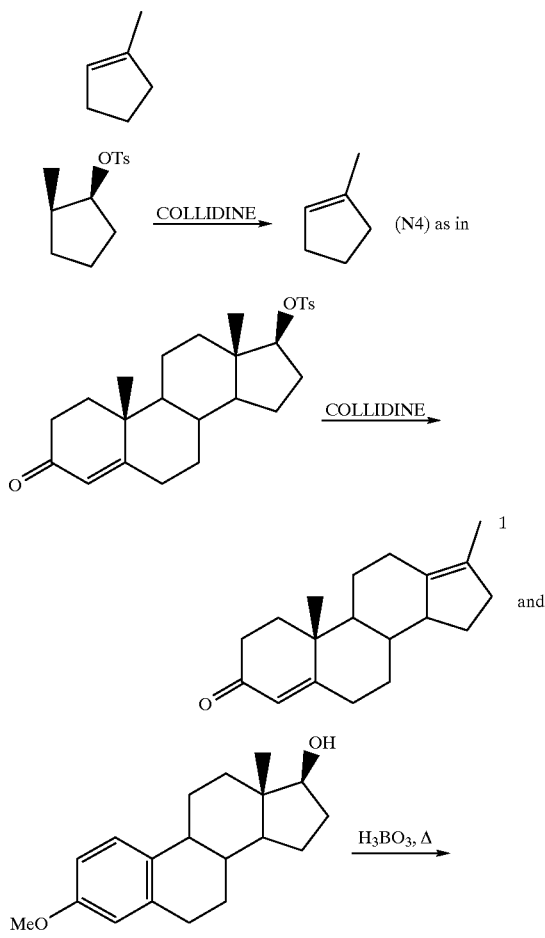

1. Günther Drefahl, Kurt Ponold and Hans Schick, Berichte, 1965, 98, 604.
2. Richard H. Peters, David F. Crows, Mitchell A. Avery, Wesley K. M. Chong, and Masako Tanabe, J. Med. Chem., 1989, 32, 1642.

-continued

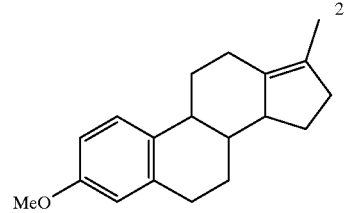

1. Franz Sondheimer, O. Mancera, M. Urquiza & G. Rosenkranz, J. Am. Chem Soc., 1955, 77, 4145.
2. William F. Johns, J. Org. Chem., 1961, 26, 4583.

Methylandrostenes

German Off. 2,631,915 teaches preparation of

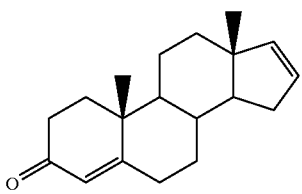

with a methyl group at any one of the following positions: 1α, 2α, 4, 6α, 6β, 7α, and 16.

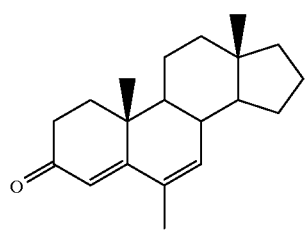

6-METHYLANDROSTA-4,6-DIEN-3-ONE

German Off. 2,428,679.

Syntheses of the 17-METHYLANDROSTENES:

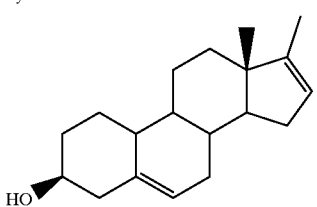

and

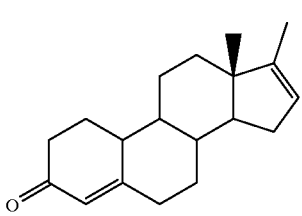

Daniel Bertin and Lucien Nedelac, Mémoires Présentes a la Société Chimique, 1964, No. 345, p. 2140.
Synthesizable compounds therefore include these, together with those derived from them; i.e., N1 with methyl at 1α, 2α, 4, 6α, 6β, 7α, 16 or 17 combined with A1, A3, A4, A5, A8, A9, A10 or A11, as well as A2 or A6 with a 17-methyl.
Haloandrostenes
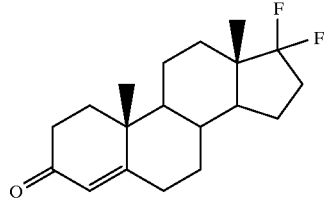
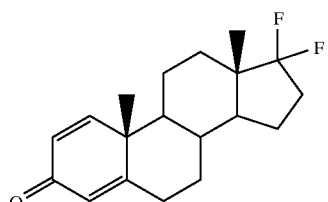
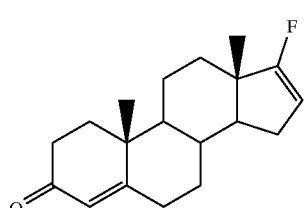
U.S. Pat. No. 3,413,321.
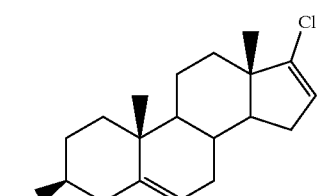
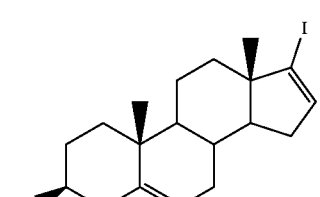
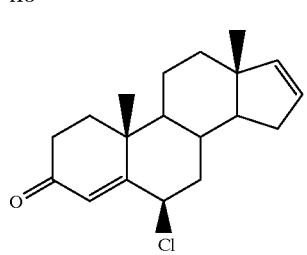
-continued
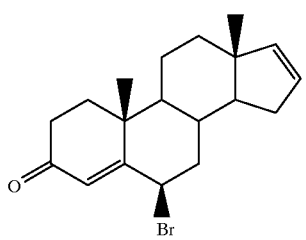
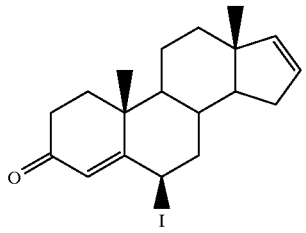
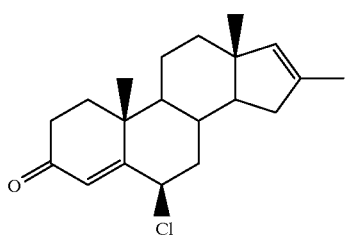
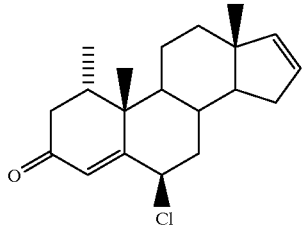
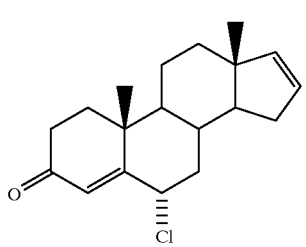
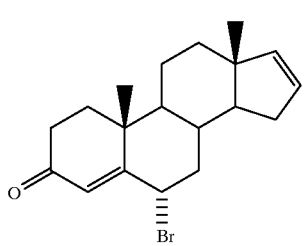
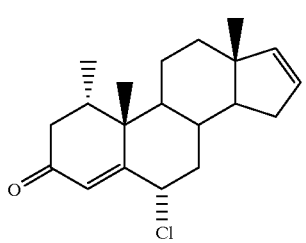

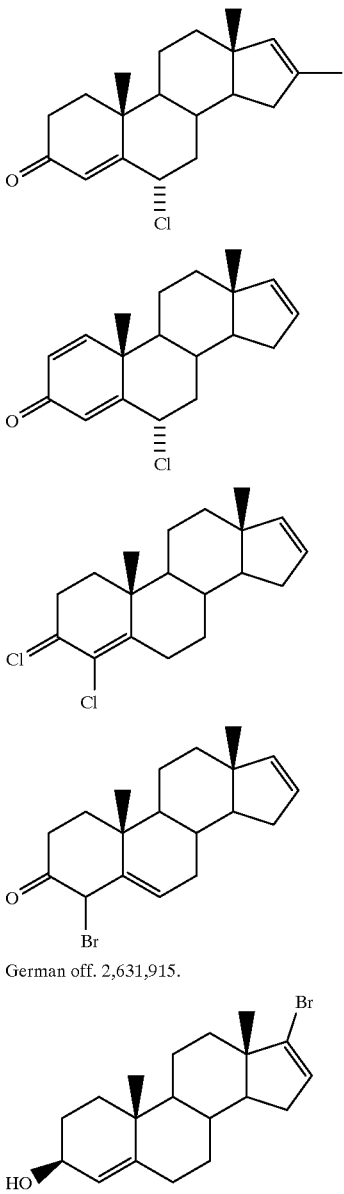

German off. 2,631,915.

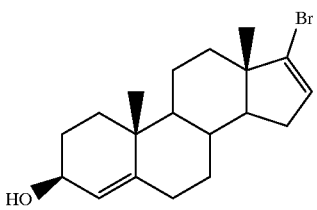

European Patent Application EP 208,497.

Synthesizable compounds therefore include these, together with those derived from them; i.e., (4-Chloro, 4-Bromo, 6α-Chloro, 6α-Bromo, 6β-Chloro, 6β-Bromo, or 6β-Iodo)-A1 in comination with N1, N2, N3, or N4. In addition, (17-Fluoro, 17-Chloro, 17-Bromo, or 17-Iodo)-N1 in combination with A1, A2, A3, A4, A5, A6, A8, A9, A10 or A11.

B. Synthetic Methods

1. Preparation of 3-, 5-, 6-, 18- and 19- position derivatives.

The compounds used in the methods of this invention are Androstane steroids substituted at the 3-, 5-, 6-, 18- and 19-positions. Many of the 3- and 5-substituted steroids are known compounds which may be derived from 17-hydroxy- and 17-oxo-steroids (commercially available e.g. from Aldrich Chemical Co) by elimination or reduction to the Δ16 homologue. The syntheses of most of these compounds are described by Ohloff (supra). As shown in FIG. 1, 17β-hydroxy-5α-Androstan-3-one (I) and methyl chloroformate (a) in pyridine gives the methyl carbonate, 17β-methoxycarbonyloxy-5α-Androstan-3-one (II) which provides a starting material for the 5α-Androst-16-en-(3-one and 3-ols) (Ohloff, supra at pg 200).

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as NaH, KM or KOBut, silver oxide or barium oxide in polar, aprotic solvents as for example, DMF, DMSO and hexamethylphosphoramide.

General procedures for synthetic reactions of steroids are known to those skilled in art. Where time and temperature of reactions must be determined, these can be determined by a routine methodology. After addition of the required reagents, the mixture is stirred under an inert atmosphere and aliquots are removed at hourly intervals. The aliquots are analyzed by chromatography to monitor the disappearance of starting material, at which point the work-up procedure is initiated. If the starting material is not consumed within twenty-four hours, the mixture is heated to reflux and hourly aliquots are analyzed, as before, until the starting material disappears. In this case the mixture is allowed to cool before the work-up procedure is initiated.

Purification of the products is accomplished by means of chromatography and/or crystallization, as known to those skilled in the art.

2. Preparation of 19-OH derivatives

Synthesis of 19-OH-Androsta-4,16-diene-3-one.

This compound has been disclosed as an intermediate in the synthesis of 19-oxo-3-aza-A-homo-5B-androstane (Habermehl, et al., Z. Naturforsch. (1970) 25b:191–195). A method of synthesizing this compound is provided.

C. Pharmaceutical Compositions and Methods of Use

An embodiment of the subject invention is a method of altering the hypothalamic function of an individual. Another embodiment is altering an autonomic function of an individual. These autonomic functions include but are not limited to heart rate, respiratory rate, brain wave patterns (percentage alpha cortical activity), body temperature. Other embodiments include, but are not limited to, methods of diminishing negative affect, negative mood or negative character traits of an individual. Another embodiment is a method of treating female premenstrual stress. All of these embodiments are accomplished by means of the non-systemic, nasal administration of certain 16-Androstene steroids, or combinations of 16-Androstene steroids.

This particular mode of administration is distinguished from alternative modes, such as ingestion or injection, in several important ways, these by virtue of the direct contact with the VNO provided by the nasal administration of the steroid ligand. In the methods of this invention, the appropriate ligand is administered directly to the chemoreceptors in the nasal passage and the vomeronasal organ, without pills or needles—i.e., non-invasively. Drug action is mediated through binding of the ligands, described herein, to specific receptors displayed by neuroepithelial cells in the nose, preferably in the VNO. This Furthermore, the mode of drug action is through the nervous system and not through the circulatory system—thus brain function can be affected without consideration of the blood-brain barrier. These methods of treatment provide a direct means of affecting the hypothalamus through the nervous system because there is only one synaptic junction between pheromone receptors and the hypothalamus. Because sensory nerves are addressed to a specific location in the brain, this method has a highly specific drug effect, thereby greatly reducing the potential of undesirable side-effects.

VNO contact is important because the VNO is associated with chemoreceptive/pheromonal function. The VNO consists of a pair of blind tubular diverticula which are found at the inferior margin of the nasal septum. The VNO contains neuro-epithelia, the axons of which have direct synapses to the amygdala and from there, to the hypothalamus. The existence of the VNO has been well documented in most terrestrial vertebrates including the human fetus; however, in adult humans it is generally thought to be rudimentary (See Johnson, et al., supra).

The ligand substances described herein, or their sulfated, cypionated, benzoated, propionated, or glucuronated derivatives, may be administered directly, but are preferably administered as compositions. They are prepared in a liquid dosage form such as, for example, liquids, suspensions or the like, preferably in unit dosage forms suitable for single administration of precise dosages. Liquid dosages may be administered as nose drops or as an aerosol. Alternatively, the active compound can be prepared as a creme or an ointment composition and applied topically within the nasal cavity. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials 2,201, 1981). Natural polymers, such as gelatin and cellulose slowly dissolve in a matter of minutes to hours while silicone remains intact for a period of months. The compositions will include a conventional pharmaceutical carrier or excipient, one or more of the active Androstene compound(s) of Formula I. In addition, the compositions may include other medicinal agents, pharmaceutical agents, carriers, adjuvants, etc.

The most likely means of communication of a semiochemical ligand is the inhalation of a naturally occurring pheromone present on the skin of another. Several 16-Androstene steroids, including 5α-Androst-16-en-3α-ol and 5α-Androst-16-en-3-one, 4, 16-Androstadien-3-one, 5α-Androstadien-3β-ol, and perhaps 5α-Androstadien-3α-ol, are naturally occurring in humans and may be present on the skin. It is estimated that the naturally occurring maximum concentration of a 16-Androstene steroid on human skin is from 2 to 7 ng/cm$^2$. During intimate contact it is estimated that a human would be exposed to no more than 700 ng of a naturally occurring steroid. Since these compounds are relatively nonvolatile, it is estimated that, even during intimate contact, a human subject would inhale no more than 0.7 pg of a naturally occurring steroid from the skin of another. From the amount inhaled only about 1% would reach the receptors of the vomeronasal organ. Thus the estimated maximum natural exposure to naturally produced pheromones would be 0.007 pg.

The amount of semiochemical ligand administered will of course, be dependent on the subject being treated, the severity of the affliction, the manner of administration, the frequency of administration, and the judgment of the prescribing physician. However, a single dosage of at least about 10 picograms, delivered directly into the lumen of the vomeronasal organ, is effective in eliciting a transient autonomic response. When administered to the nasal cavity, the dosage is about 100 picograms to about 100 micrograms, preferably about 1 nanogram to about 10 micrograms, more preferably about 10 nanograms to 1 about microgram. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Co., Easton, Pa., 15th Ed., 1975. The composition or formulation to be administered will, in any event, contain a quantity of one or more of the active compound(s) in an amount effective to alleviate the symptoms of the subject being treated.

For aerosol administration, the active ingredient is preferably supplied in finely divided form along with a surfactant and a propellant. Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, olestearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates or sorbitan, e.g., those sold under the trademarks "Arlacel C" (sorbitan sesquioleate), "Span 80" (sorbitan monoleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

Yet another means of administration is topical application of a volatile liquid composition to the skin, preferably facial skin, of an individual. The composition will usually contain an alcohol such as ethanol or isopropanol. A pleasant odorant may also be included in the composition.

D. Measuring Affect, Mood and Character Trait.

Feeling states associated with affects, moods and character traits are generally measured by use of a questionnaire. For example questionnaires comprising a number of adjectives which refer to feeling states may be administered to an individual. The individual evaluates his or her feeling state described by the adjective and rates the intensity of the feeling on a numerical scale. Clustering of related adjectives and statistical analysis of a subject's evaluation of each adjective provides a basis for the measurement of various feeling states.

Alternatively, feeling states may be measured by autonomic changes, such as those used in polygraphic evaluations (galvanic skin response, pulse rate and the like). Cabanac, M. Annual Review of Physiology (1975) 37:415; Hardy, J. D., "Body Temperature Regulation", Chapter 59, pp. 1417. In: Medical Physiology. Vol. IIEd.: VB Mountcastle (1980); Wolfram Bouscein. Electrodermal Activity (Plenum Press 1992). In addition, non-verbal cues such as facial expression and body posture may be evaluated.

III. EXAMPLES

The following examples are intended to illustrate but not to limit the invention.

Abbreviations used in the examples are as follows: aq.= aqueous; RT.=room temperature; PE=petroleum ether (b.p. 50–70°); DMF=N,N-dimethylformamide; DMSO=dimethyl sulfoxide; THF=tetrahydrofuran.

Example 1

Androsta-4,16-dien-3-one (4).

This synthesis is depicted in FIG. 1. Several methods are known for the conversion of testosterone into Androsta-4, 16-dien-3-one (Brooksbank et al., *Biochem. J.* (1950) AZ:36). Alternatively, thermolysis (460°) of the methyl carbonate of testosterone gives Androsta-4,16-dien-3-one in 90% yield. 17B-MethoxyCarbonyioxy-androst-4-en-3-one (IV) was prepared from testosterone (III. Fluka) with methyl chloroformate/pyridine (a) in 76% yield (after recrystallization from MeOH). M.p. 140–141°, [a $]_D$=+95.4° (c=1.10)—IR. (CDCl$_3$): 1740s, 1665s, 1450s, 1280s,—$^1$H-NMR. (360 MHz): 0.87 (s, 3 H); 1.20 (s, 3 H); 3.77 (s, 3 H); 4.53 (br. t, J 8, 1 H); 5.75 (s, 1 H). A solution of the methyl carbonate IV in toluene was pyrolyzed (b) as described for I. Recrystallization of the crude product from acetone at RT. gave pure ketone 4 in 90% yield. M.p. 127–129.5°, (a)$_D$+118.9° (C=1.32) ([3]: m.p. 131.5–133.5° (hexane), [a]$_D^{16}$=+123±3.5° (C=1.03)).—IR. (CDCl$_3$): 3050w, 1660s, 1615m.—$^1$H-NMR. (360 MHz): 0.82 (s, 3 H); 1.22 (s, 3 H); 5.70 (m, 1 H); 5.73 (s, 1 H); 5.84 (m, 1 H).

Example 2

Androsta-4,16-dien-3α-ol (5) and -3β-ol (6).

These syntheses are depicted in FIG. 1. Androsta-4,16-dien-3-one (4) was reduced at −55° with lithium tris (1, 2-dimethylpropyl) hydridoborate in THF (c) as described for the preparation of 2 (FIG. 1). Chromatography on silica gel with CH$_2$Cl$_2$/ethyl acetate 9:1 gave pure axial alcohol 5 (48% yield) and pure equatorial alcohol 6 (48% yield). Analytical samples were further purified by recrystallization (from PE at −30° for 5, from cyclohexane at RT. for 6).

Data of 5. M.p. 77–79°, [a]$_D$ +120.6° (C=1.26)—IR. (CDCl$_3$): 3620m, 3440m br., 1660m, 1595w.—$^1$H-NMR. (360 MHz): 0.79 (s, 3 H); 1.02 (s, 3 H); 4.07 (m, w$_{1/2}$≈10, 1 H); 5.48 (dxd, J 5 and 2, 1 H); 5.71 (m, 1 H); 5.85 (m, 1 H).

Data of 6. M.p. 116.1190, [a]$_D$ +53.9° (C=1.28) ([47]: m.p. 116.1180, [$^8$)D +59.3° (C=0.4)—IR. (CDCl$_3$): 3610m, 3420m br., 3050m, 1660m, 1590w.—$^1$H-NMR. (360 MHz): 0.78 (s, 3 H); 1.08 (s, 3 H); 4.15 (m, w$_{1/2}$≈20, 1 H); 5.30 (m, w$_{1/2}$≈5, 1 H); 5.71 (m, 1 H); 5.85 (m, 1 H).

Example 3

Androsta-5,16-dien-3α-ol (7).

Figure 2:
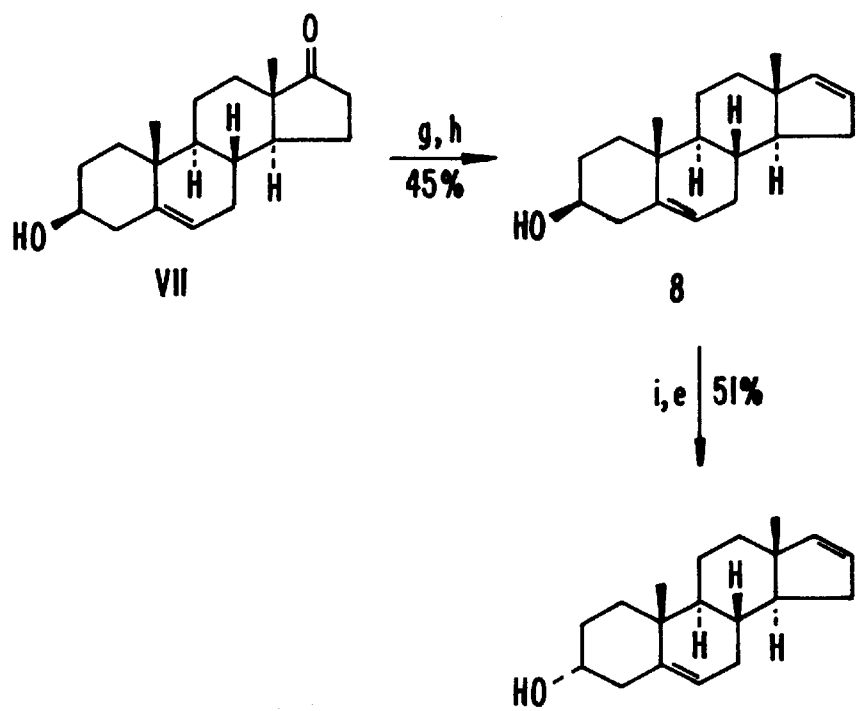
FIG. 2 illustrates the synthesis of Androsta-5,16-dien-3α-ol and Androsta-5,16-dien-3β-ol.

This synthesis is depicted in FIG. 2. To a solution of alcohol 8 (545 mg, 2.0 mmol) in acetone (100 ml) at 0° C. under N$_2$was added rapidly Jones reagent (i, 1.5 ml, ca. 4 mmol). After 5 min., the mixture was poured into a dilute phosphate buffer (pH 7.2, 1200 ml) and extracted with ether. The extracts were washed with sat. aq. NaCl solution, dried (Na$_2$SO$_4$) and evaporated to give mainly Androsta-5,16-dien-3-one as an oil (567 mg). The crude product was dissolved In THF (7 ml) and reduced with lithium tris (1,2-dimethylpropyl) hydridoborate (c) at 0.55° as described for the preparation of 2. The crude product (530 mg) was chromatographed on silica gel (100 g) with CH$_2$Cl$_2$/ethyl acetate 4:1 to give 280 mg (51%) of pure a-alcohol 7 (eluted first) and 13 mg of starting alcohol 8. A small sample of 7 was recrystallized from acetone/water at RT. M.p. 1380, [$^8$]D −77.5° (c=1.2.—IR. (CDCl$_3$): 3580m, 3430m, 1665w, 1590w,—$^1$H-NMR. (360 MHz): 0.80 (s, 3 H); 1.06 (s, 3 H); 4.02 (m, w$_{1/2}$≈8, 1 H); 5.44 (m, 1 H); 5.72 (m, 1 H); 5.86 (m, 1 H).

Example 4

Androsta-5,16-dien-3β-ol (8).

This compound was prepared in 73% yield by a known procedure (Marx, A. F., et al., Ger. Offen. 2,631,915; Chem. Abst. 87:23614p (1977)) from commercial (Fluka) 3B-hydroxy-androst-5-en-17-one (VII). M.p. 137°, [a]$_D$ =−71.9° (c=1.5) ([48]: m.p. 140–141°, [a]$_D$=68°.—IR. (CDCl$_3$): 3600m, 3420m br., 1670w, 1590w,—$^1$H-NMR. (360 MHz): 0.80 (s, 3 H); 1.05 (s, 3 H); 3.53 (m, w$_{1/2}$≈22, 1 H); 5.38 (m, 1 H); 5.72 (m, 1 H); 5.86 (m, 1 H). This synthesis is depicted in FIG. 4.

Example 5

Alternate synthesis of Androsta-4,16-dien-3-one (25).

Figure 3:
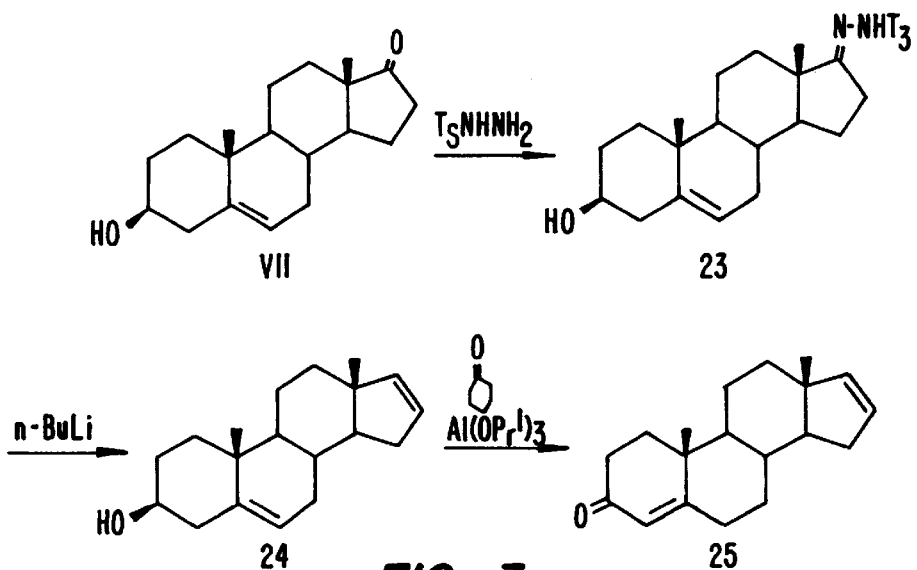
FIG. 3 illustrates an alternate synthesis of Androsta-4,16-dien-3-one.

The following method of synthesis is depicted in FIG. 3:
Dehydroepiandrosterone p-Toluenesulfonylhydrazone (23)

Dehydroepiandrosterone (VII) (14.4 g, 50.0 m mole) and p-toluenesulfonylhydrazide (12.75 g, 68.5 m mole) in dry methanol (300 ml) were heated under reflux for 20 hours. The mixture was transferred to a conical flask and allowed to cool. The crystalline product was filtered under suction and washed with methanol (50 ml). Further crops of product were obtained by sequentially evaporating the filtrate to 75 ml and 20 ml, and allowing crystallization each time. Total yield was 21.6 g (95%).

Androsta-5, 16-dien-3β-ol (24)

Dehydroepiandrosterone p-toluenesulfonylhydrazone (23) (22.8g, 50.0 m mole) in dry tetrahydrofuran (1.0 liters) was cooled in a dry ice/isopropanol bath, The-mixture was stirred while n-butyl lithium (125 ml of 1.6 M solution in hexane, 200 m mole) was added. The mixture was allowed to warm to room temperature and was stirred for 24 hours. Water (50 ml) was added with cooling in ice. The mixture was poured into saturated ammonium chloride solution/ice (500 ml) and extracted with ether (x2). The organic layers were washed with saturated sodium bicarbonate solution (500 ml) and saturated sodium chloride solution (500 ml), dried (MgSO$_4$) and evaporated in vacuo to give the crude product. This was purified by flash chromatography on 190 g silica gel 60, 230–400 mesh, eluting with ethyl acetate/ hexane (20:80→50:50) to give crystalline material. The product was recrystallized from methanol (45 ml)/3% hydrogen peroxide −(8 ml) washing with methanol (30 ml)/water (8 ml) to give pure product (6.75 g, 50%).

Androsta-4, 16-dien-3-one (25)

A solution of 10 g of Androsta-5,16-dien-3β-ol (24) in 475 cc of toluene and 75 cc of cyclohexanone was distilled (ca. 50 cc of distillate was collected) to eliminate moisture, 5 g of Al(OPr$^i$)$_3$ in 50 cc of toluene was added and the solution was refluxed for 1 hour. Water then was added, volatile components were removed by steam distillation and the residue was extracted with chloroform. Evaporation of the dried extract, followed by crystallization of the residue from chloroform-hexane, yielded 7.53 g of Androsta-4,16-dien-3-one (25). Another 0.97 g (total, 8.5 g, 86%) was obtained by chromatography of the mother liquor on neutral alumina.

Example 6

Synthesis of Androsta-3,5,16-trien-3-yl methyl ether (12).

To a partial solution of androsta-4,16-dien-3-one (1.00 g, 3.70 mmol) in 2.2-dimethoxypropane (5.0 mL, 41 mmol) and 5 mL DMF were added methanol (0.2 mL) and p-toluenesulfonic acid monohydrate (26.4 mg, 0.139 mmol). The mixture was refluxed 5 h, after which it was cooled and sodium bicarbonate (152.5 mg) was added. The suspension was partitioned between 50 mL of ice water and 50 mL of ethyl acetate. The organic layer was washed with two 50 mL portions of water +50 mL of brine, dried over magnesium sulfate, filtered, and concentrated under reduced pressure. The residual oil was taken up in 50 mL of hot hexane and filtered through a 12 mm×30 mm column of silica gel 60 using 150 mL of hot hexane. The combined filtrates were concentrated under reduced pressure and recrystallized from acetone/methanol to give white crystals (468.0 mg, 1.645 mmol, 44%), m.p. 83–92° C.

Example 7

Synthesis of 17-methylene-Androst-4-en-ols.

To 20-homoandrosta-4,17-dien-3-one (119.0 mg, 0.4184 mmol) in 5 mL of methanol were added sodium borohydride (6.0 mg, 0.16 mmol) and 77 μL of water. After stirring 2 h further sodium borohydride (32.0 mg, 0.846 mmol) was added and the mixture was stirred overnight. After concentrating under reduced (5% ethyl acetate/hexane on silica gel) to give a more polar (59.8 mg) and a less polar (1.7 mg) product.

Example 8

Synthesis of 17-methylene-6-oxo-Androsta-4-en-3-one.

To a cooled solution of 20-homoandrosta-5,17-dien-3-ol (399.4 mg, 1.394 mmol) in 50 mL of acetone was added 2.67M Jones reagent (2.0 mL, 5.3 mmol). After stirring 1 h the reaction was quenched with isopropanol (1.0 mL, 13 mmol) and poured into 100 mL of water. The mixture was extracted three times with 50 mL portions of ethyl acetate and the combined organic extracts were washed with 50 mL of saturated sodium bicarbonate +50 mL of brine. The organic phase was then dried over magnesium sulfate, filtered, and concentrated under reduced pressure. The residue was recrystallized from 95% ethanol to give an almost white powder (177.8 mg, 0.5958 mmol, 43%), m.p. 113–115° C.

Example 9

Synthesis of 6β-OH-Androsta-4,16-dien-3-one.

To a solution of androsta-3,5,16-trien-3-yl methyl ether, (12) (200.5 mg, 0.7049 mmol), in 5 mL of 1,2-dimethoxyethane (DME) and 1 mL of water was added m-chloroperbenzoic acid (MCPBA, 77.4%, 173.2 mg, 0.776 mmol) suspended in 5 mL of DME +1 mL of water +0.40 g of 5% (w/w) NaOH dropwise, with stirring, over a period of 90 min. After stirring 18 h further MCPBA (247.0 mg, 1.11 mmol) suspended in 10 mL of DME +2 mL of water +0.8 g of 5% (w/w) NaOH was added dropwise, with stirring, over 1½ h. The reaction mixture was stirred ½ h and then poured into 25 mL of saturated sodium bicarbonate. The aqueous mixture was extracted three times with 25 mL of ether and the combined organic extracts were washed with 50 g of 5% (w/w) sodium thiosulfate+three 50 mL portions of brine, dried over magnesium sulfate, filtered through Celite, and concentrated under reduced pressure. The resulting crystalline residue was purified by preparative TLC (35% ethyl acetate/hexane on silica gel) followed by two-fold recrystallization from aqueous ethanol to give lustrous white platelets (102.3 mg, 0.3571 mmol, 51%), m.p. 165–166° C.

Example 10

Figure 12:
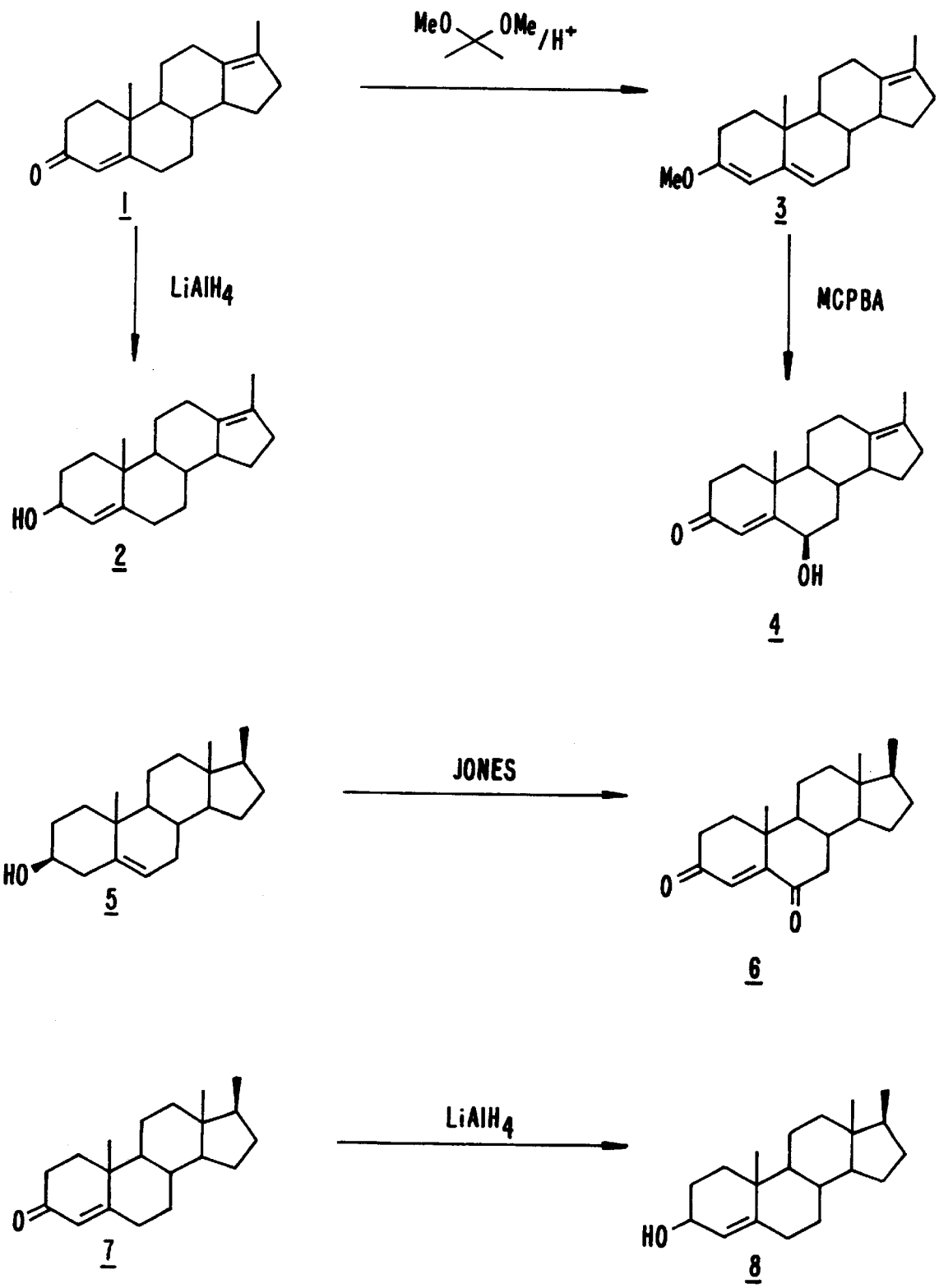
FIG. 12 illustrates the steps of synthesis for Examples 10 through 14.

18-Nor-17-methylandrosta-4,13(17)-dien-3-ol, 2:

Refer to FIG. 12. To a solution of 18-nor-17-methylandrosta-4,13(17)-dien-3-one (1, 378.2 mg, 1.399 mmol) in 7.5 mL of ahh. ether were added 59.7 mg (1.57 mmol) of lithium aluminum hydride (LAH). After stirring the resulting suspension for 30 min. 2.00 g of Glauber's salt were added and the mixture was stirred a further 30 min. The mixture was then filtered and extracted with four 25 mL portions of ether. The combined filtrates were concentrated under reduced pressure and then subjected to preparative TLC (silica gel GF, 1000μ, 5% ethyl acetate/methylene chloride as eluent) to give a less polar fraction ($R_f$ 0.63, 34.5 mg, 0.127 mmol, 9%) and a more polar fraction ($R_f$ 0.45, 273.8 mg, 1.005 mmol, 72%).

(NA- 1994A-209)

Example 11

18-Nor-17-methylandrosta-3,5,13(17)-trien-3-yl methyl ether, 3:

Refer to FIG. 12. A solution of 18-nor-17-methylandrosta-4,13(17)-dien-3-one (1, 0.86 g, 3.2 mmol) in 2,2-dimethoxypropane (4.3 mL, 35 mmol) and dimethylformamide (DMF, 4.3 mL) containing anh. methanol (0.17 mL) and p-toluenesulfonic acid monohydrate (21.3 mg) was refluxed 4 h and then allowed to cool. Sodium bicarbonate (0.13 g) was added and the mixture was partitioned between 65 mL of hexanes and 40 mL of ice water. The organic phase was washed with two 40 mL portions of water +40 mL of brine and then flash filtered through a 17 mm high×30 mm dia. column of silica gel (200–400 mesh). Concentration of the combined filtrates followed by recrystallization from acetone/95% ethanol gave bright yellow crystals (489.6 mg, 1.721 mmol, 54%), m.p. 95–101° C. TLC (10% ethyl acetate/hexanes on silica gel) showed a major product at $R_f$ 0.69 with a trace contaminant at the origin.

Example 12

18-Nor-17-methylandrosta-4,13(17)-dien-6β-ol-3-one, 4:

Refer to FIG. 12. Reaction was carried out similar to the procedure of D. N. Kirk and J. M. Wiles, *J. Chem. Soc., Chem. Commun.* 1974, 927. To a stirred solution of 18-nor-17-methylandrosta-3,5,13(17)-trien-3-yl methyl ether (477.0 mg, 1.677 mmol) in 1,2-dimethoxyethane (DME, 26 mL) was added 77% m-chloroperbenzoic acid (MCPBA, 999.7 mg, 4.48 mEq) suspended in DME (39 mL), water (8 mL), and 5% (w/w) sodium hydroxide (7.1 mL), over a period of 88 min. After stirring 20 h the reaction mixture was poured into saturated sodium bicarbonate (50 mL) and extracted with three 50 mL portions of ether. The combined organic extracts were washed with 50 g of 5% (w/w) sodium thiosulfate pentahydrate+three 50 mL portions of brine, dried over magnesium sulfate, and filtered through diatomaceous earth. The residue was washed with 25 mL of ether and the combined filtrates were concentrated under reduced pressure to give a yellow syrup. Purification by preparative TLC (silica gel GF, 1000μ, 35% ethyl acetate/hexanes as eluent) gave an off-white crystalline film (132.1 mg, 0.4612 mmol, 28%) which TLC (35% ethyl acetate/hexanes on silica gel) showed contained a major component ($R_f$ 0.23) and a minor component ($R_f$ 0.18).
(NA-1994A-223)

Example 13
17β-Methylandrost-4-en-3,6-dione, 6:

Refer to FIG. 12. Jones reagent (2.67 M, 0.88 mL, 2.3 mmol) was added to a solution of 17β-methylandrost-5-en-3β-ol (5, 135.5 mg, 0.4697 mmol) (J. B. Jones and K. D. Gordon, *Can. J. Chem.* 1972, 50, 2712–2718) in acetone (15 mL) and the mixture was stirred 45 min. The reaction was quenched with the addition of 2-propanol (0.44 mL). After stirring a further 10 min. the reaction mixture was poured into 30 mL of water and extracted with three 15 mL portions of ethyl acetate. The combined organic extracts were washed with 15 mL of saturated sodium bicarbonate +15 mL of brine, dried over magnesium sulfate, and filtered through diatomaceous earth. The residue was washed with 10 mL of ethyl acetate and the combined filtrates were concentrated under reduced pressure. Preparative TLC (silica gel GF, 1000μ, 25% ethyl acetate/hexanes as eluent), and recrystallization from aqueous ethanol gave lustrous off-white crystals (37.5 mg, 0.125 mmol, 27%), m.p. 94–95° C., homogeneous to TLC (25% ethyl acetate/hexanes on silica gel, $R_f$ 0.39).
(NA-1994A-298)

Example 14
17β-Methylandrost-4-en-3-ol, 8:

Refer to FIG. 12. LAH (21.3 mg, 0.561 mmol) was added to a solution of 17β-methylandrost-4-en-3-one (7, 143.2 mg, 0.4999 mmol) (J. B. Jones and K. D. Gordon, *Can. J. Chem.* 1972, 50, 2712–2718) in 2.8 mL of anh. ether. After stirring the suspension for 30 min. Glauber's salt (0.76 g) was added and the mixture stirred a further ½ h. Ether (10 mL) was added and the suspension was filtered through diatomaceous earth. The residue was washed with three 10 mL portions of ether and the combined filtrates were concentrated under reduced pressure. The crude product was separated by preparative TLC (silica gel GF, 1000μ, 5% ethyl acetate/methylene chloride as eluent) into a more polar component ($R_f$ 0.30, 77.9 mg, 0.270 mmol, 54%) and a less polar component ($R_f$ 0.43, 10.3 mg, 0.0357 mmol, 7%).
(NA-1994A-300)

Figure 13:
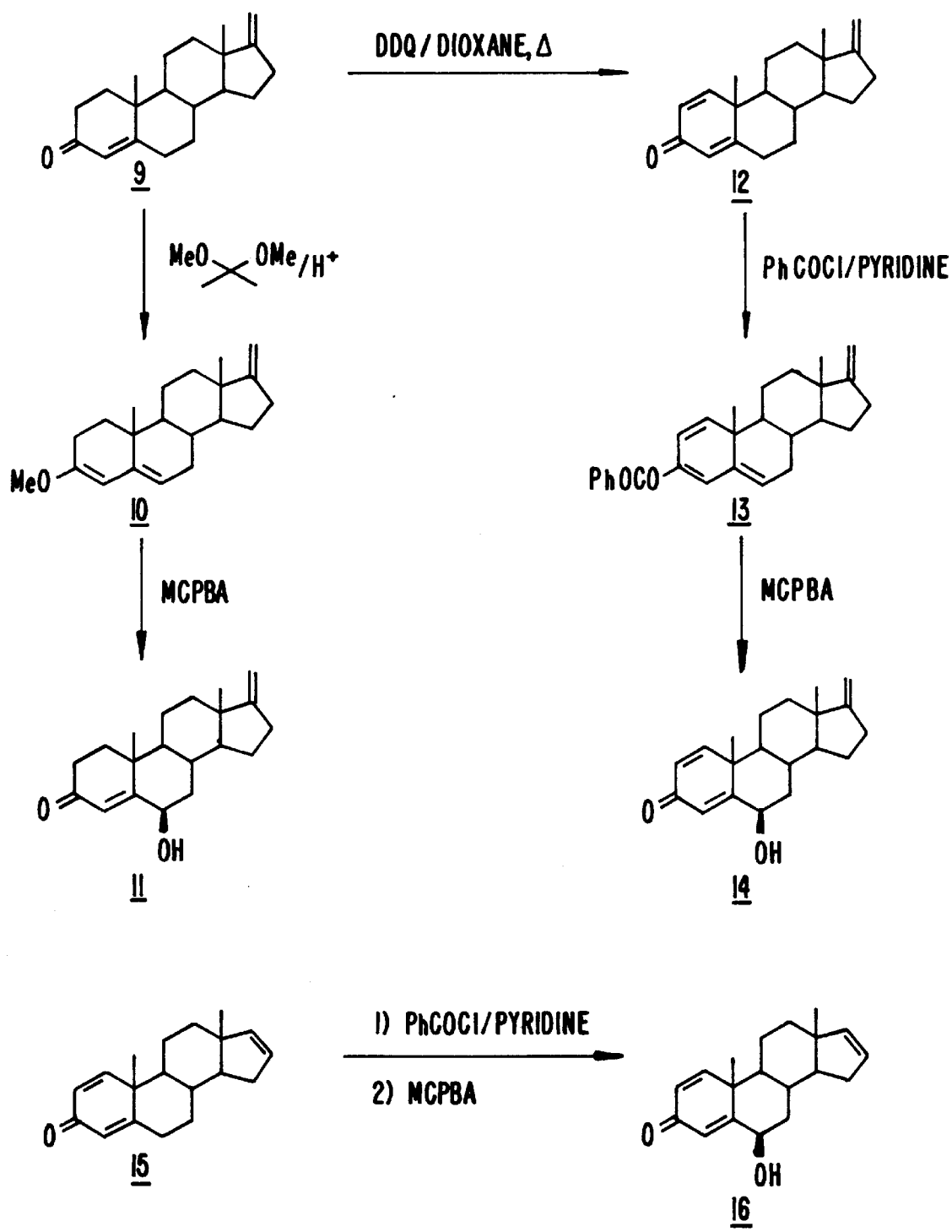
FIG. 13 illustrates the steps of synthesis for Examples 15 through 20.

Example 15
17-Methylenandrosta-3,5-dien-3-yl methyl ether, 10:

Refer to FIG. 13. To 17-methylenandrost-4-en-3-one (9, 2.0000 g, 7.0314 mmol) in 2,2-dimethoxypropane (9.4 mL, 76 mmol) and DMF (9.4 mL) were added 0.37 mL of anh. methanol and 47.0 mg of p-toluenesulfonic acid. After refluxing 4 h the reaction mixture was allowed to cool and then partitioned between 140 mL of hexanes and 90 mL of water. The organic phase was washed with two 90 mL portions of water +90 mL of brine, dried over magnesium sulfate, and flash filtered through a 30 mm dia.×37 mm high column of silica gel (200–400 mesh). Product continued eluting with 200 mL of hexanes. Concentration of the combined filtrates under reduced pressure and recrystallization of the residue from acetone/methanol gave very slightly yellow platelets (1.5291 g, 5.1231 mmol, 73%), m.p. 97–99° C., homogeneous to TLC (25% ethyl acetate/hexanes on silica gel, $R_f$ 0.72).
(NA-1994A-226)

Example 16
17-Methylenandrost-4-en-6β-ol-3-one, 11:

Refer to FIG. 13. To a stirred solution of 17-methylenandrosta-3,5-dien-3-yl methyl ether (10, 500.1 mg, 1.676 mmol) in DME (10 mL) was added MCPBA (318.6 mg, 1.846 mmol) in DME (10 mL) and water (4 mL) over a period of 15 min. After stirring 30 min. the mixture was poured into 50 mL of saturated sodium bicarbonate and extracted with three 50 mL portions of ether. The combined organic extracts were washed with 50 g of 5% (w/w) sodium thiosulfate pentahydrate+three 50 mL portions of brine, dried over magnesium sulfate, and filtered through diatomaceous earth. The residue was washed with 25 mL of ether and the combined filtrates were concentrated under reduced pressure. Flash chromatography (45% ethyl acetate/hexanes on silica gel) followed by recrystallization from aqueous ethanol gave slightly yellow crystals (187.1 mg, 0.6228 mmol, 37%), m.p. 192–194° C., which TLC (35% ethyl acetate/hexanes on silica gel) showed consisted of major ($R_f$ 0.17) and minor ($R_f$ 0.13) components.
(NA-1994A-232)

Example 17
17-Methylenandrosta-1,4-dien-3-one, 12:

Refer to FIG. 13. A solution of 17-methylenandrost-4-en-3-one (9, 1.0001 g, 3.5160 mmol) and 2,3-dichloro-5,6-dicyano-1,4-benzoquinone (DDQ, 2.43 g, 10.7 mmol) in dioxane (60 mL, freshly distilled after overnight reflux over sodium) was refluxed 6 h and then cooled with swirling in tap water. Methyl t-butyl ether (MTBE, 50 mL) was added and the suspension was filtered through diatomaceous earth. The residue was washed with two 50 mL portions of MTBE and the combined filtrates were concentrated under reduced pressure. Flash chromatography of the residue (20% ethyl acetate/hexanes on silica gel) followed by recrystallization from 95% ethanol gave off-white crystals (498.9 mg, 1.767 mmol, 50%), m.p. 155–157° C.
(NA-1994A-234)

Example 18
17-Methylenandrosta-1,3,5-trien-3-yl benzoate, 13:

Refer to FIG. 13. Reaction was carried out in a procedure adapted from R. W. Draper et al., *Arzneim.-Forsch.* 1982, 32, 317–322, as follows: 17-Methylenandrosta-1,4-dien-3-one (12, 389.0 mg, 1.378 mmol), anh. pyridine (4.7 mL, 58 mmol), and benzoyl chloride (1.2 mL, 10 mmol) under argon were stirred 18 h in an oil bath (68–73° C). After cooling in ice the reaction mixture was poured into 40 mL of ice-1 N MCl and extracted with three 20 mL portions of methylene chloride. The combined organic extracts were washed with 40 mL of cold 1 N HCl+40 mL of saturated sodium bicarbonate +40 mL of brine, dried over magnesium sulfate, and filtered through diatomaceous earth. The residue was washed with 10 mL of methylene chloride and the combined filtrates were concentrated under reduced pressure. Flash chromatography (4% ethyl acetate/hexanes on silica gel) gave a yellow solid (0.43 g, 1.1 mmol, 81%).
(NA-1994A-284)

Example 19
17-Methylenandrosta-1,4-dien-6β-ol-3-one, 14:

Refer to FIG. 13. Reaction was carried out in a procedure adapted from R. W. Draper et al., *Arzneim.-Forsch.* 1982, 32, 317–322, as follows: MCPBA (211.4 mg, 1.225 nmol) in DME (6.6 mL) and water (2.7 mL) was added to 17-methylenandrosta-1,3,5-trien-3-yl benzoate (13, 0.43 g, 1.1 mmol) in 6.6 mL of DME over a period 20 min. with stirring. stirring was continued 30 min. and the reaction mixture was then poured into 35 mL of saturated sodium bicarbonate. The mixture was extracted with three 35 mL portions of ethyl acetate. The combined organic extracts were washed with 35 g of 5% sodium thiosulfate pentahydrate+three 35 mL portions of brine, dried over magnesium sulfate, and filtered through diatomaceous earth. The residue was washed with 10 mL of ethyl acetate and the combined filtrates were concentrated under reduced pressure. Preparative TLC (silica gel GF, 1000μ, 50% ethyl acetate/hexanes as eluent) gave a yellow crystalline solid (83.7 mg, 0.280 mmol, 25%) homogeneous to TLC (50% ethyl acetate/hexanes on silica gel, R$_f$ 0.50).
(NA-1994A-292)

Example 20

Androsta-1,4,16-trien-6β-ol-3-one, 16:

Refer to FIG. 13. Androsta-1,4,16-trien-3-one (15, 500.0 mg, 1.863 mmol), anh. pyridine (6.4 mL, 79 mmol), and benzoyl chloride (1.6 mL, 14 mmol) under argon were placed in an oil bath (70–73° C.) and stirred 18 h. After cooling in ice the mixture was poured into 50 mL of ice-1 N HCl and extracted with three 25 mL portions of methylene chloride. The combined organic extracts were washed with 50 mL of cold 1 N HCl+50 mL of saturated sodium bicarbonate+50 mL of brine, dried over magnesium sulfate, and filtered through diatomaceous earth. The residue was washed with 10 mL of methylene chloride and the combined filtrates were concentrated under reduced pressure. Flash chromatography (2% ethyl acetate/hexanes on silica gel) gave yellow crystals (0.47 g, 1.3 mmol, 68%) of intermediate benzoate. This was taken up in chloroform (30 mL) with MCPBA (240.0 mg, 1.391 mmol). After stirring 1 h further MCPBA (239.5 mg, 1.388 mmol) was added and the reaction was stirred another hour. The mixture was then washed with 30 g of 5% (w/w) sodium thiosulfate pentahydrate +30 mL of saturated sodium bicarbonate +30 mL of brine, dried over magnesium sulfate, and filtered through diatomaceous earth. The residue was washed with 10 mL of chloroform and the combined filtrates were concentrated under reduced pressure. Flash chromatography (40–45% ethyl acetate/hexanes on silica gel) gave a yellow resin (106.1 mg, 0.3731 mmol, 29%), which TLC (40% ethyl acetate/hexanes on silica gel) showed contained major (R$_f$ 0.34) and minor (R$_f$ 0.40) components.
(NA-1994A-276)

Example 21

Androsta-4,16-dien-6β-ol-3-one, 16:

To a solution of androsta-3,5,16-trien-3-yl methyl ether, 12 (200.5 mg, 0.7049 mmol), in 5 mL of 1,2-dimethoxyethane (DME) and 1 mL of water was added m-chloroperbenzoic acid (MCPBA, 77.4%, 173.2 mg, 0.776 mmol) suspended in 5 mL of DME +1 mL of water +0.40 g of 5% (wlw) NaOH dropwise, with stirring, over a period of 90 min. After stirring 18 h further MCPBA (247.0 mg, 1.11 mmol) suspended in 10 mL of DME +2 mL of water +0.8 g of 5% (w/w) NaOH was added dropwise, with stirring, over 1½ h. The reaction mixture was stirred ½ h and then poured into 25 mL of saturated sodium bicarbonate. The aqueous mixture was extracted three times with 25 mL of ether and the combined organic extracts were washed with 50 g of 5% (w/w) sodium thiosulfate+three 50 mL portions of brine, dried over magnesium sulfate, filtered through Celite, and concentrated under reduced pressure. The resulting crystalline residue was purified by preparative TLC (35% ethyl acetate/hexane on silica gel) followed by two-fold recrystallization from aqueous ethanol to give lustrous white platelets (102.3 mg, 0.3571 mmol, 51%), m.p. 165–166° C. (NA-1993B-40,43B)

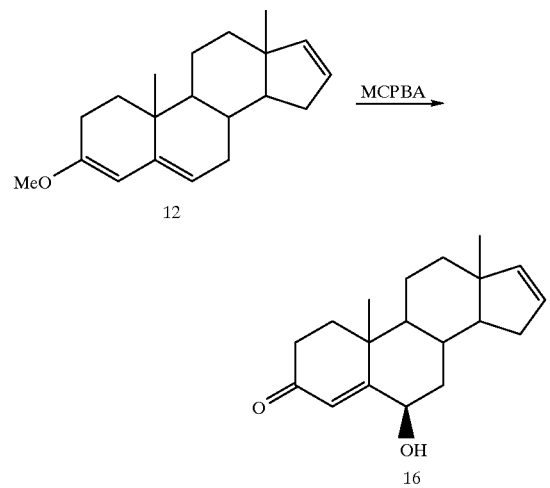

Example 22

Figure 14:
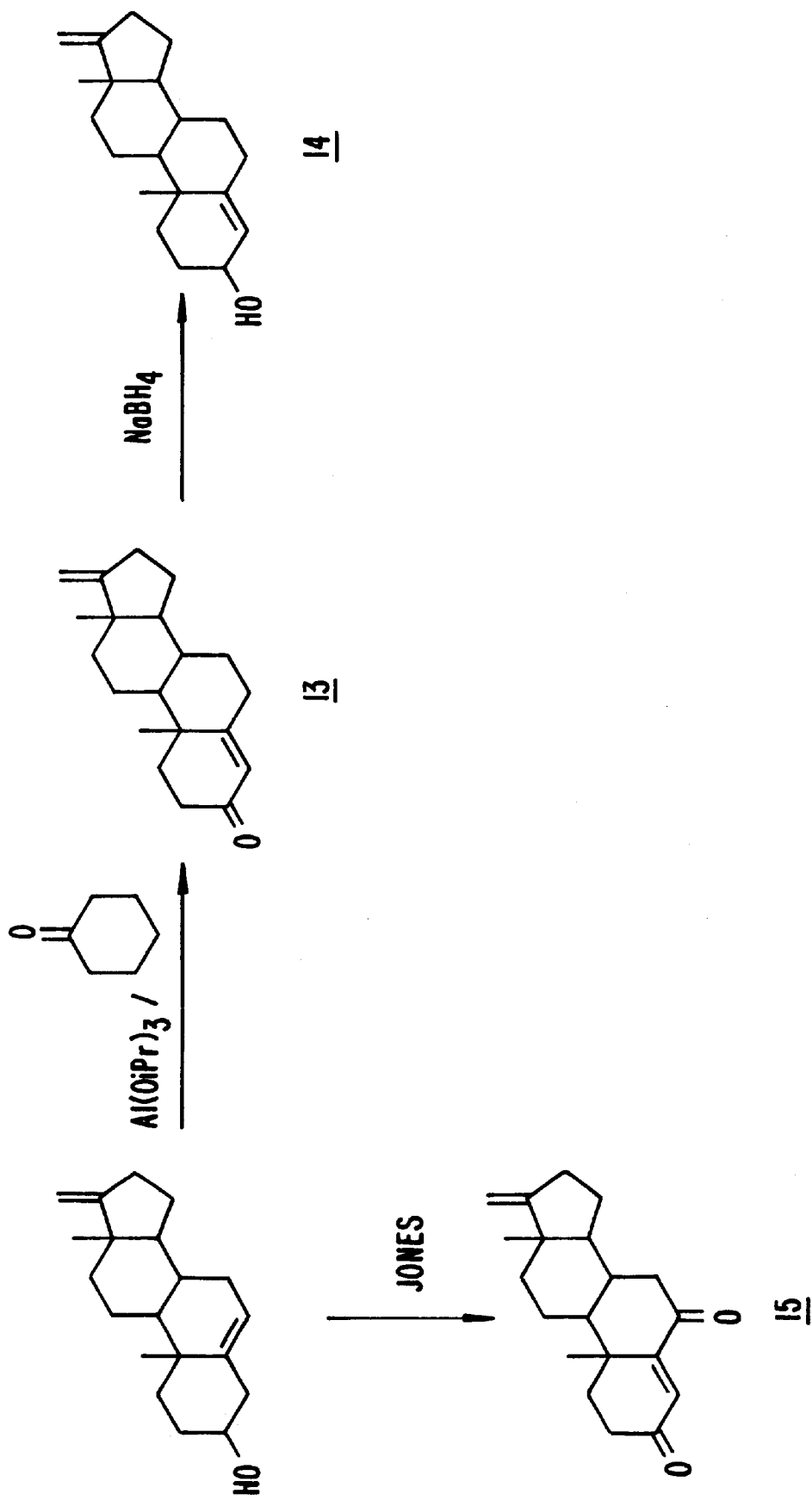
FIG. 14 illustrates the steps of synthesis for Examples 22 through 24.

20-Homoandrosta-4,17-dien-3-one, 13:

Refer to FIG. 14. To a partial solution of 20-homoandrosta-5,17-dien-3-ol (1.0001 g, 3.4911 mmol) in 100 mL of toluene and 20 mL (0.19 mol) of cyclohexanone was added aluminum isopropoxide (2.00 g, 9.79 mmol) in 20 mL of warm toluene. After refluxing 4 h the cooled reaction mixture was shaken 1 min. with 5 mL of water and 12.5 mL of 3.6N sulfuric acid. The organic layer was washed with 50 mL of brine, dried over magnesium sulfate, filtered through Celite, and concentrated under reduced pressure. Following steam distillation to remove cyclohexanone the non-volatile residue was taken up in two 10 mL aliquots of dichloromethane, dried over magnesium sulfate, filtered, and concentrated. The oily residue was purified by flash Chromatography (15% ethyl acetatelhexane on silica gel) and recrystallization from aqueous acetone to give colorless needles (238.8 mg, 0.8400 mmol, 24%), m.p. 130–134° C. [lit. (B. S. Macdonald et al., *Steroids* 1971, 18, 753–766) m.p. 129–131° C.].
(NA-1993A-99, 103B)

Example 23

20-Homoandrosta-4,17-dien-3-ols, 14:

Refer to FIG. 14. To 20-homoandrosta-4,17-dien-3-one (119.0 mg, 0.4184 mmol) in 5 mL of methanol were added sodium borohydride (6.0 mg, 0.16 mmol) and 77 μL of water. After stirring 2 h further sodium borohydride (32.0 mg, 0.846 mmol) was added and the mixture was stirred overnight. After concentrating under reduced pressure the residue was purified by preparative TLC (5% ethyl acetate/hexane on silica gel) to give a more polar (59.8 mg) and a less polar (1.7 mg) product.
(NA-1993A-110A,B)

20-Homoandrosta-4,17-diene-3,6-dione, 15:

Refer to FIG. 14. To a cooled solution of 20-homoandrosta-5,17-dien-3-ol (399.4 mg, 1.394 mmol) in 50 mL of acetone was added 2.67M Jones reagent (2.0 mL, 5.3 mmol). After stirring 1 h the reaction was quenched with isopropanol (1.0 mL, 13 mmol) and poured into 100 mL of water. The mixture was extracted three times with 50 mL portions of ethyl acetate and the combined organic extracts were washed with 50 mL of saturated sodium bicarbonate +50 mL of brine. The organic phase was then dried over magnesium sulfate, filtered, and concentrated under reduced pressure. The residue was recrystallized from 95% ethanol to give an almost white powder (177.8 mg, 0.5958 mmol, 43%), m.p. 113–115° C.
(NA-1993A-91B)

Example 25

Figure 15:
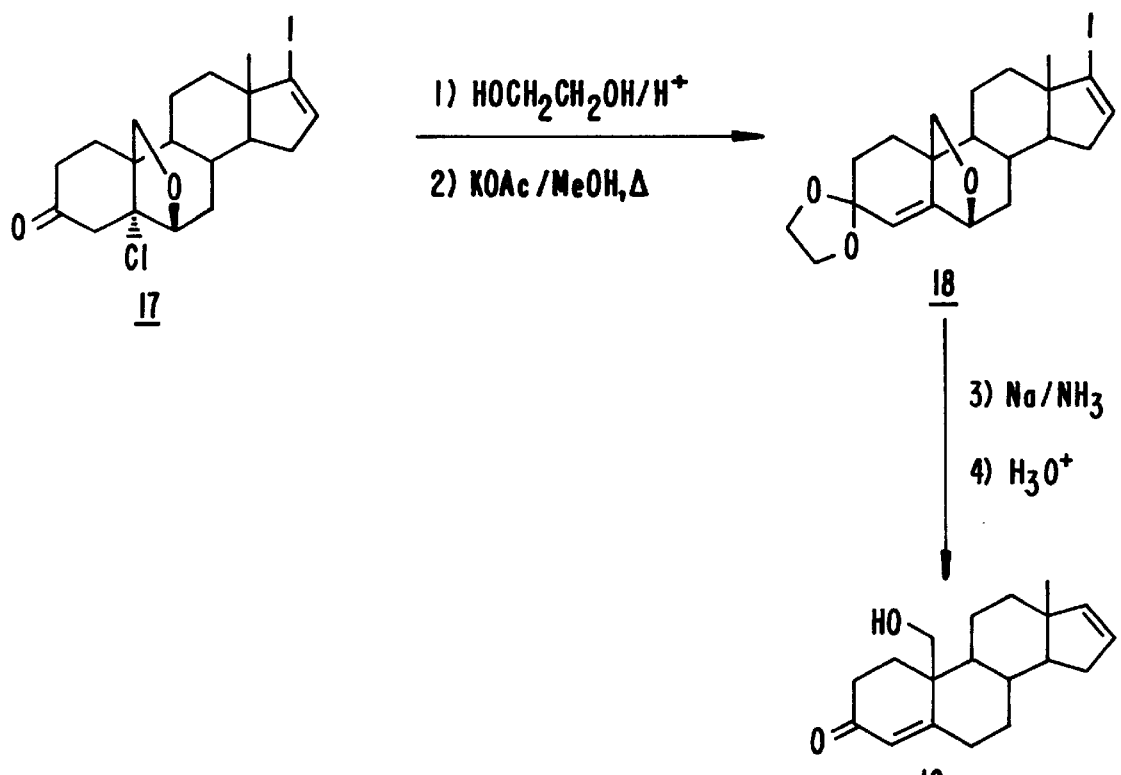
FIG. 15 illustrates the steps of synthesis for Examples 25 through 26.

6β,19-Epoxy-17-iodoandrosta-4,16-diene 3-ethylene ketal, 18:

Refer to FIG. 15. A mixture of crude 6β,19-epoxy-5β-chloro-17-iodoandrost-16-ene (17, 1.38 g, 3.09 mmol) (G. Habermehl and A. Haaf, *Z. Naturforsch.* 1970, 25b, 191–195), ethylene glycol (0.97 g, 16 mmol), toluene (50 mL), and p-toluenesulfonic acid monohydrate (20.3 mg, 0.107 mmol) was refluxed 19 h with azeotropic removal of water (Deen-Stark). After cooling ethyl acetate (100 mL) was added and the reaction mixture was washed with 100 mL of saturated sodium bicarbonate +100 mL of brine. The organic phase was dried over magnesium sulfate and filtered through diatomaceous earth. The residue was washed with 25 mL of ethyl acetate and the combined filtrates were concentrated under reduced pressure to give a tan, crystalline solid (1.47 g). This residue was suspended in anh. methanol (40 mL), potassium acetate (2.44 g, 24.9 mmol) was added, and ca. 26 mL of methanol were distilled off. The remainder was concentrated under reduced pressure, water (50 mL) was added, and the mixture was extracted three times with 25 mL aliquots of methylene chloride. The dried (sodium sulfate) extracts were filtered through diatomaceous earth and the residue was washed with 10 mL of methylene chloride. Concentration of the combined filtrates under reduced pressure gave a yellow solid, which was purified further by flash chromatography (5–7.5–10% ethyl acetate/methylene chloride on silica gel) and recrystallization from methanol to give light yellow needles (914.6 mg, 2.013 mmol, 65%), m.p. 187–189° C. $^1$H-NMR: 6.13 δ, 1H, dd, 16-H; 5.82 δ, 1H, s, 4-H; 4.71 δ, 1H, d, 6α-H; 4.22 δ and 3.53 δ, 2H, AB, 19-H's; 4.10–3.28 δ, 4M, mult., 3-ketal H's; 0.83 δ, 3H, s, 18-Me.
(NA-1994A-141C)

Example 26

Androsta-4,16-dien-19-ol-3-one, 19:

Refer to FIG. 15. Anh. ammonia (ca. 75 mL) was distilled through a KOH tower into a 250 mL flame-dried 3-neck flask fitted with an inlet adapter, a magnetic stirring bar, a dry ice/acetone condenser, and a stopper. A solution of 6β,19-epoxy-17-iodoandrosta- 4,16-diene 3-ethylene ketal (18, 880.4 mg, 1.938 mmol) in dry tetrahydrofuran (THF, 45 mL) was added, followed by metallic sodium (0.20 g, 8.7 mg-atom) cut in small pieces. After stirring under argon pressure for 30 min. the reaction was quenched with the addition of abs. ethanol (1.0 mL). Ammonia was allowed to boil off overnight, 50 mL of water were added, and the mixture was extracted with three 25 mL portions of methylene chloride. The combined organic extracts were washed with 50 mL of brine, dried over magnesium sulfate, and filtered through diatomaceous earth. After washing the residue with 10 mL of methylene chloride the combined filtrates were concentrated under reduced pressure. The intermediate ketal proved remarkably unreactive, but was finally hydrolyzed by refluxing 18 h in 5 mL of chloroform and 2.5 mL of 4 N hydrochloric acid. To the cooled hydrolysis mixture ethyl acetate (50 mL) was added and the layers were separated. The organic phase was washed with 25 mL of saturated sodium bicarbonate +25 mL of brine, dried over magnesium sulfate, and filtered through diatomaceous earth. The residue was washed with 10 mL of ethyl acetate and the combined filtrates were concentrated under reduced pressure. The resulting brown foam was purified by flash chromatography (50% ethyl acetate/hexanes on silica gel) followed by preparative TLC (50% ethyl acetate/hexanes on silica gel GF, 1000μ thickness) to give a partially crystalline film (66.7 mg, 0.233 mmol, 12%). $^1$H-NMR: 5.92 δ, 1H, s, 4-H; 5.87–5.64 δ, 2H, mult., 16,17-H's; 4.10δ and 3.94 δ, 2H, AB, 19-H's; 0.79 δ, 3H, s, 18-Me.
(NA-1994A-244D)

Example 27

Figure 16:
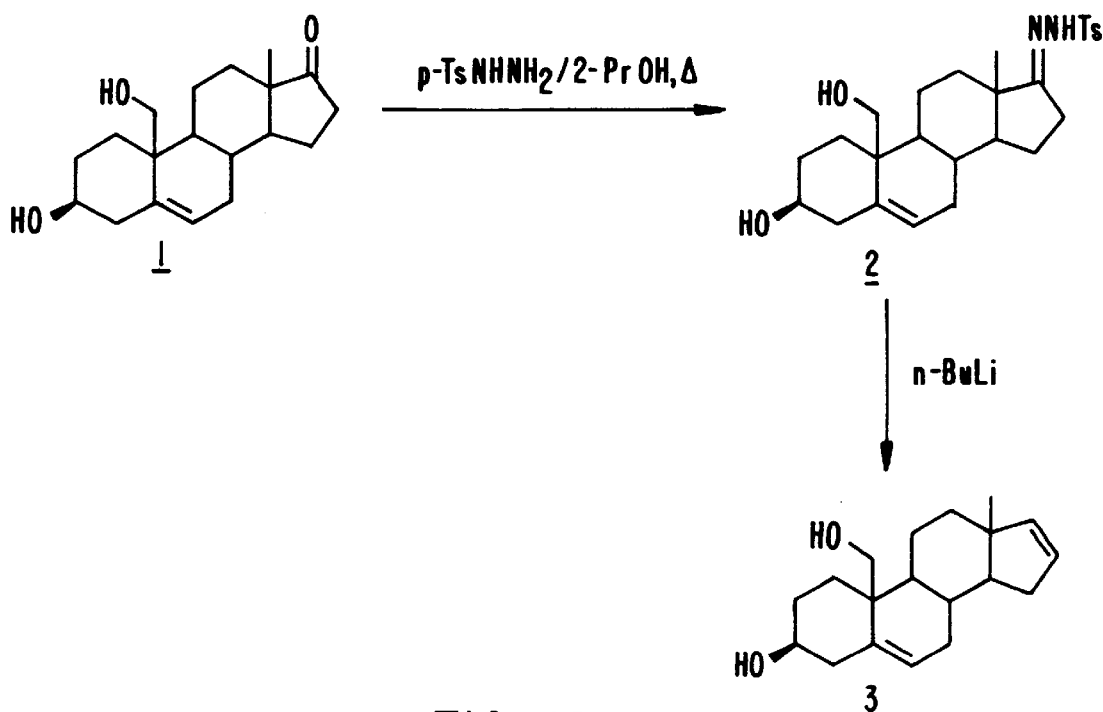
FIG. 16 illustrates the steps of synthesis for Examples 27 through 28.
Figure 17A:
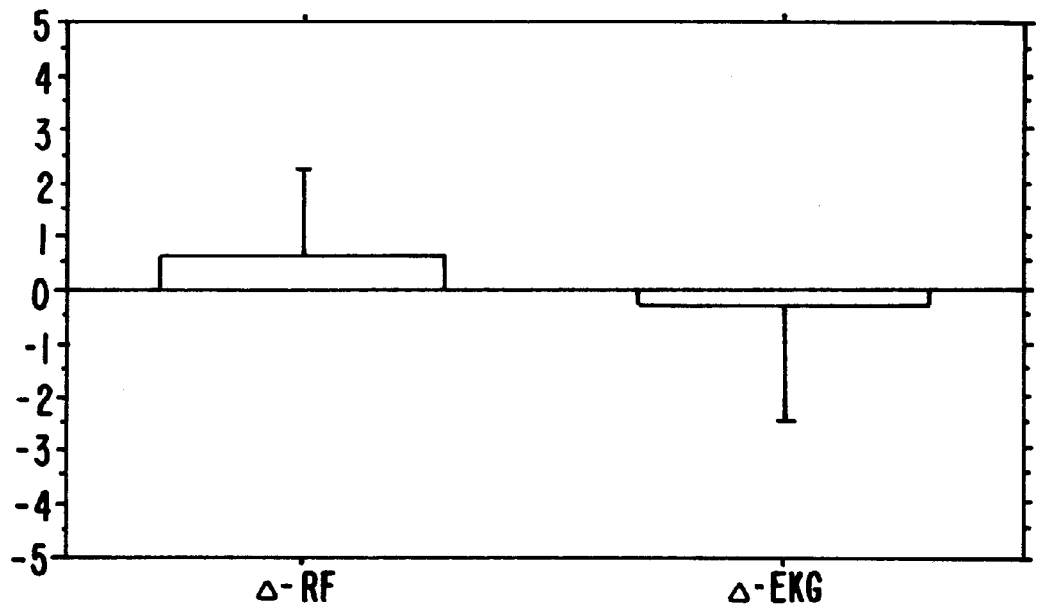
FIG. 17A shows the respiratory frequency and EKG data in males for tests of androsta-5,16-diene-3β,19-diol in the VNO.
Figure 17B:
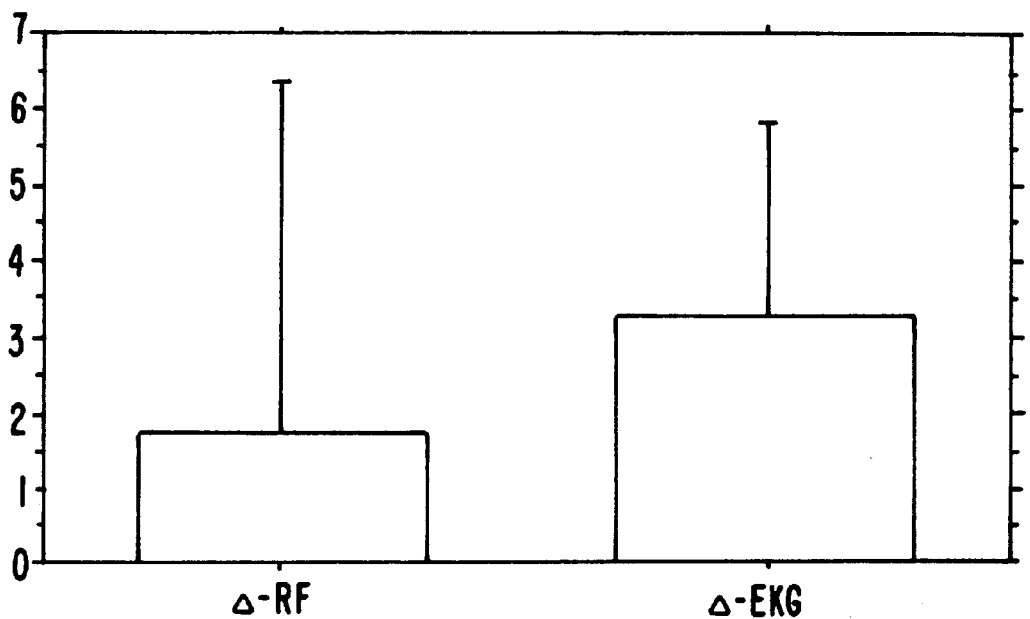
FIG. 17B shows the respiratory frequency and EKG data in females for tests of androsta-5,16-diene-3β,19-diol in the VNO.
Figure 18A:
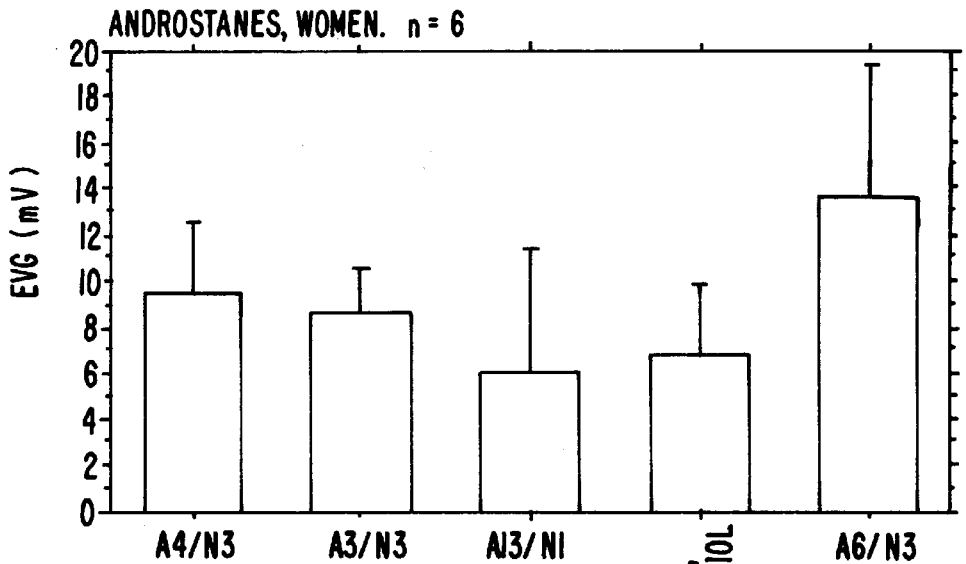
FIGS. 18A, B and C show the EVG, GSR, and ST data in women for four androstanes on the chart and androsta-5,16-diene-3β,19-diol.
Figure 18B:
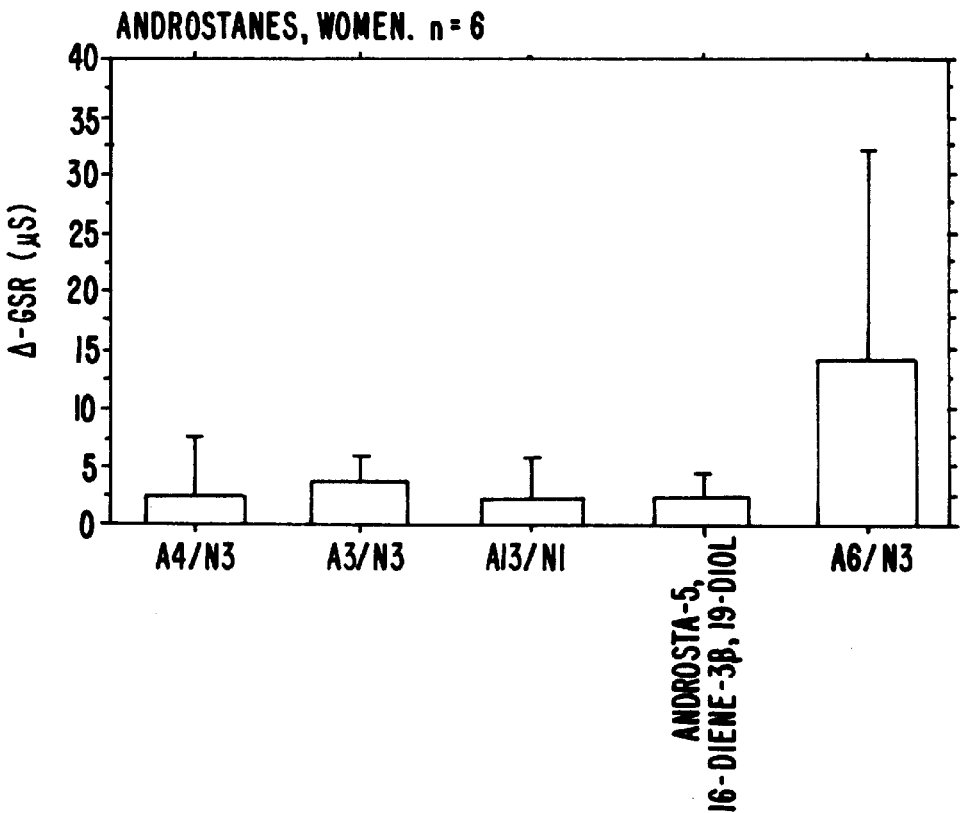
Figure 18C:
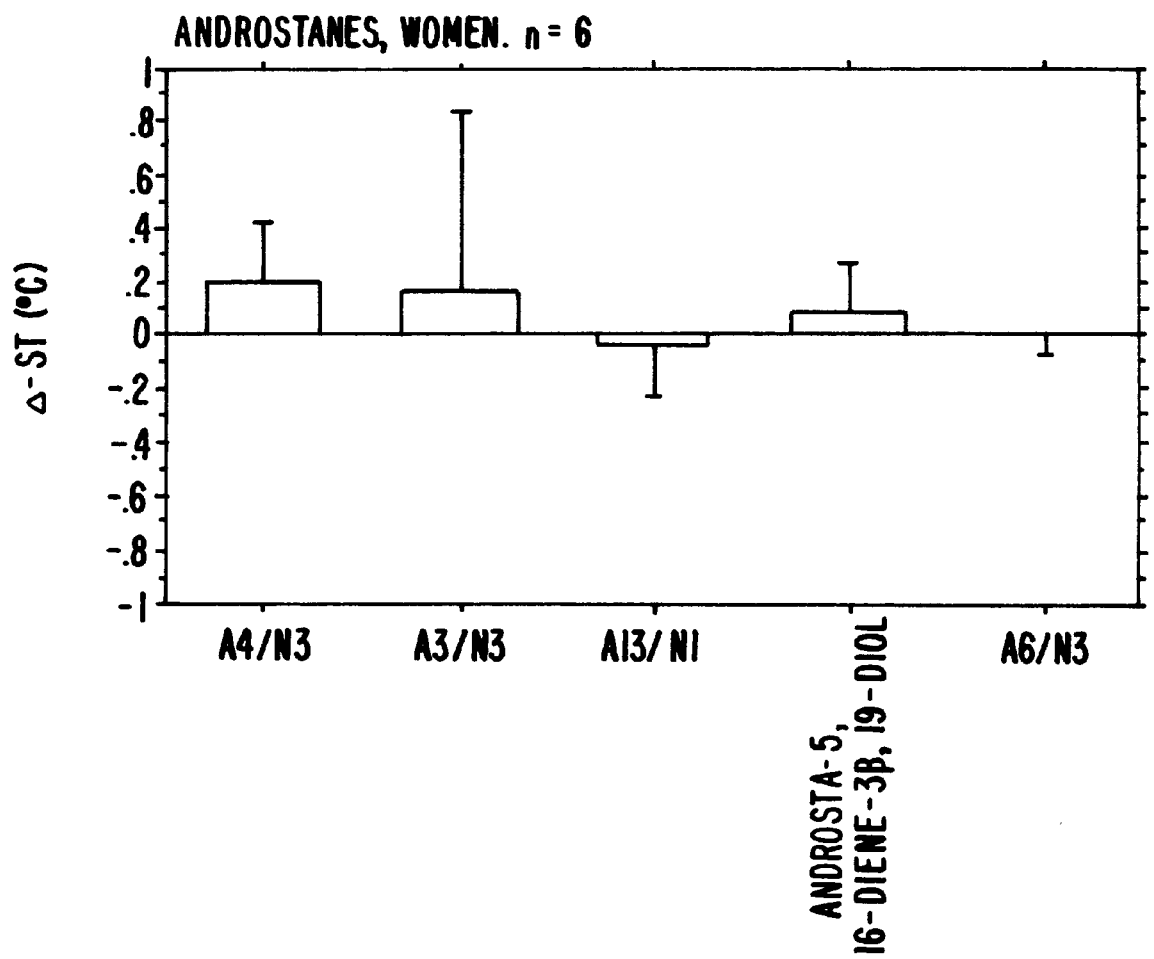
Figure 19A:
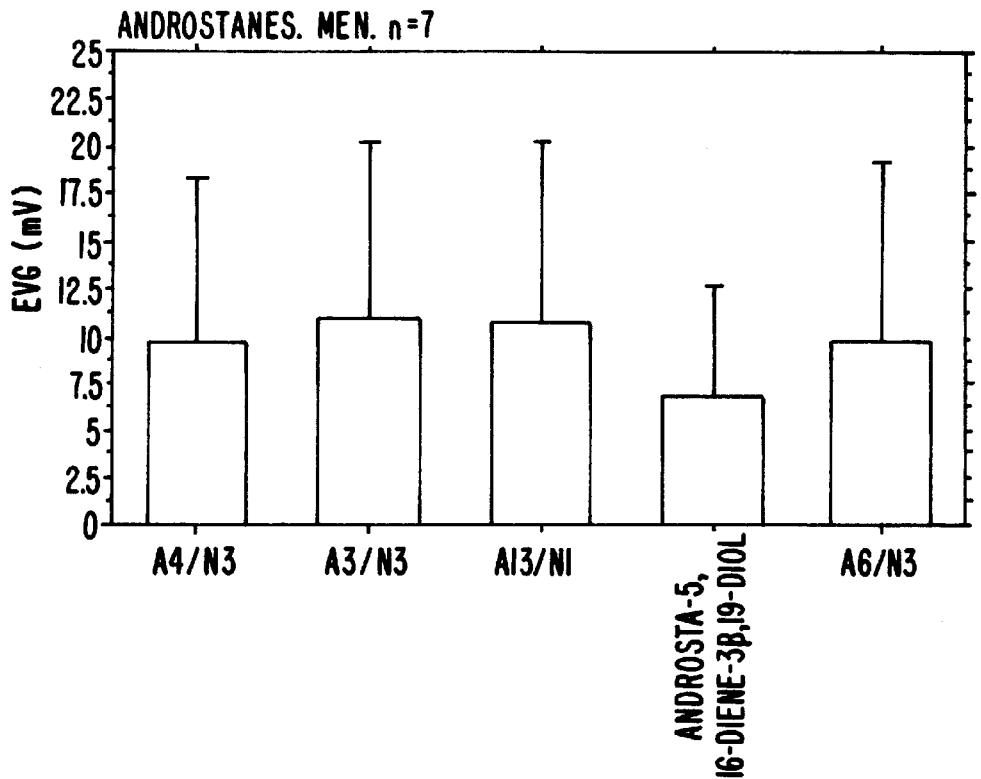
FIGS. 19A, B and C show the EVG, GSR and ST data in men for the five androstanes identified in FIG. 18.
Figure 19B:
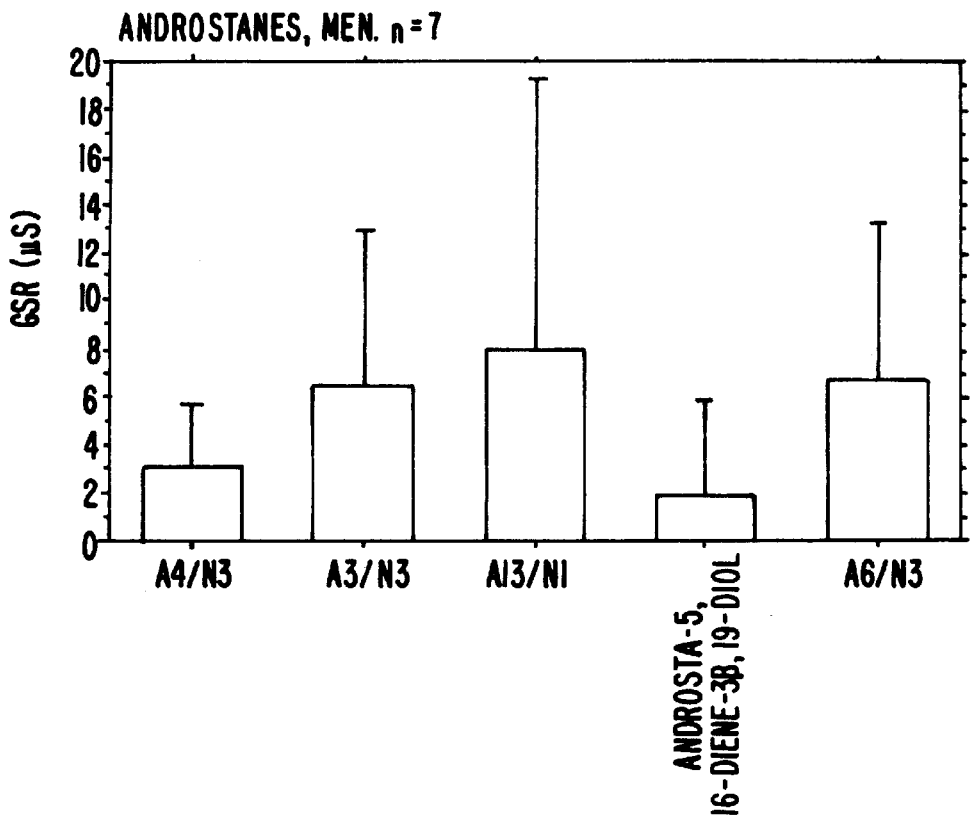
Figure 19C:
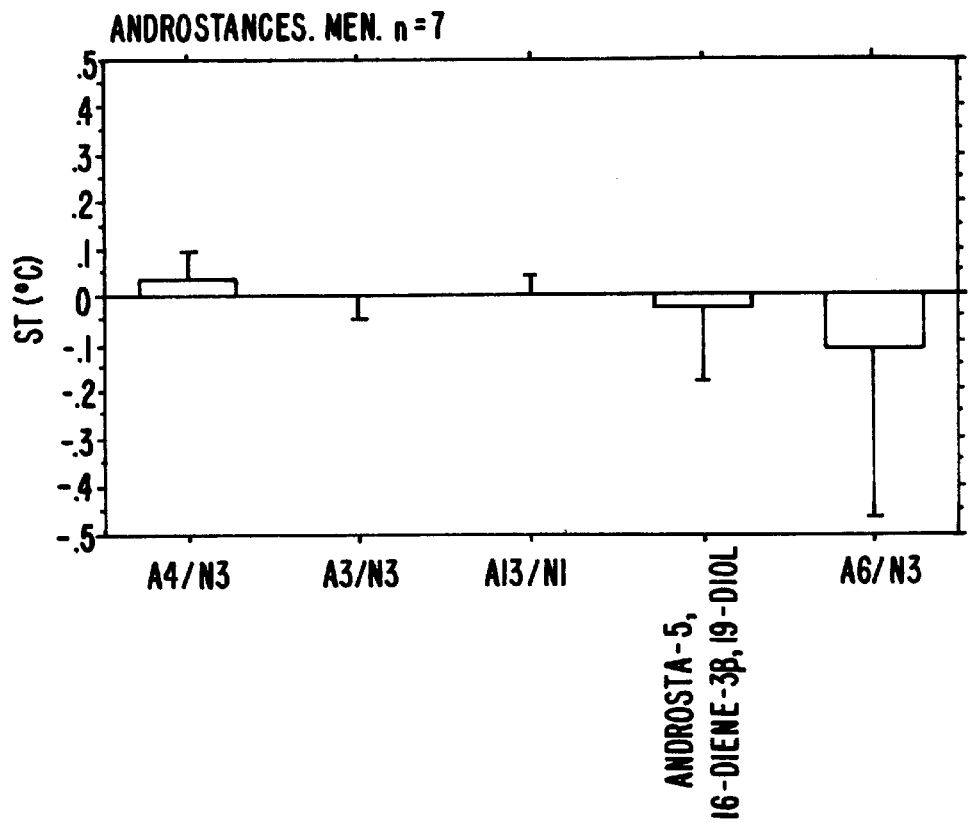
Figure 20A:
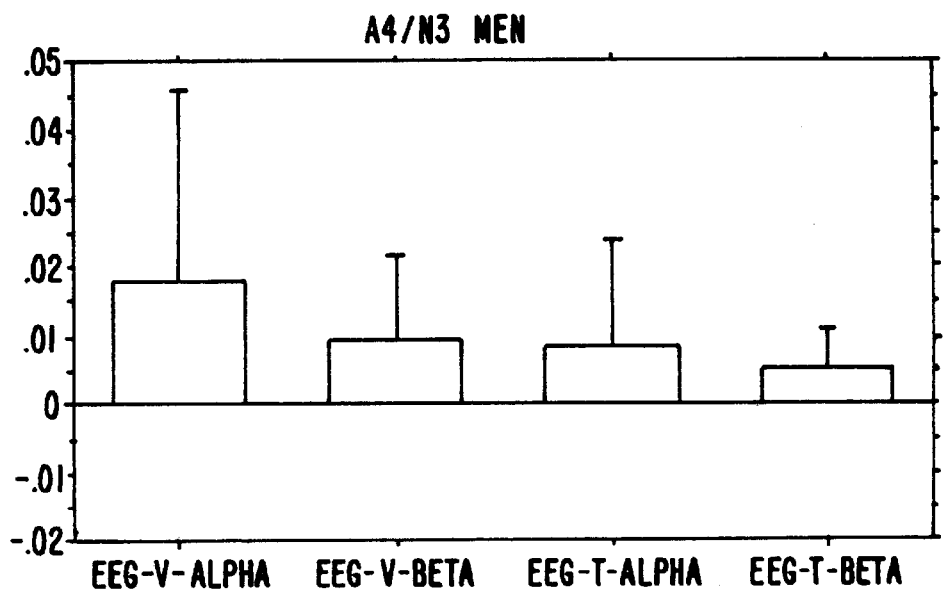
FIGS. 20A and 20B show the EEG data in men and women for androstane A4/N3.
Figure 20B:
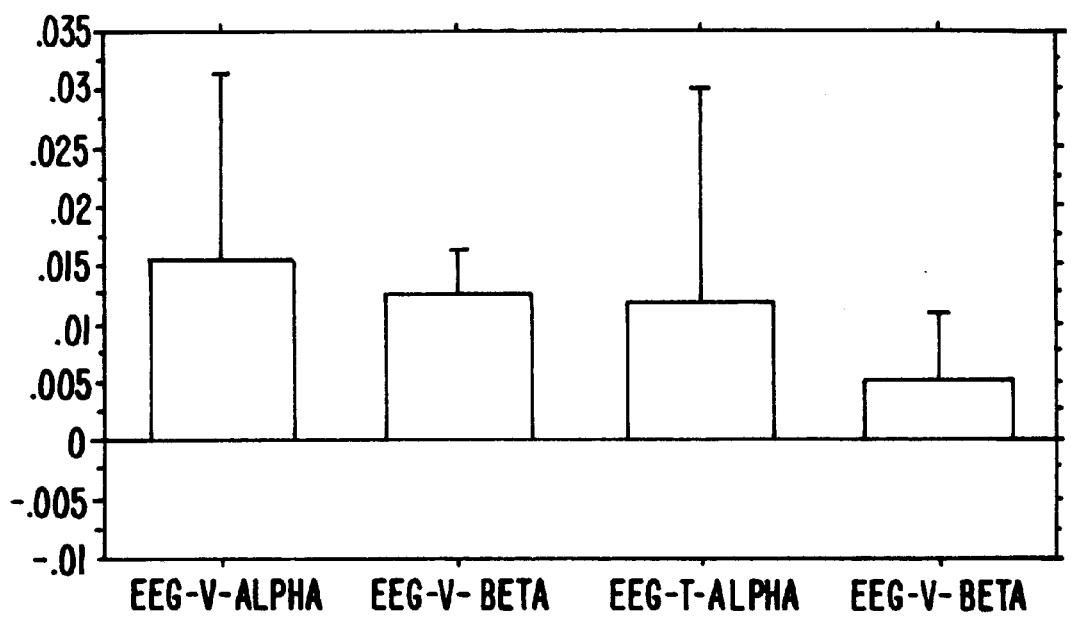
Figure 21A:
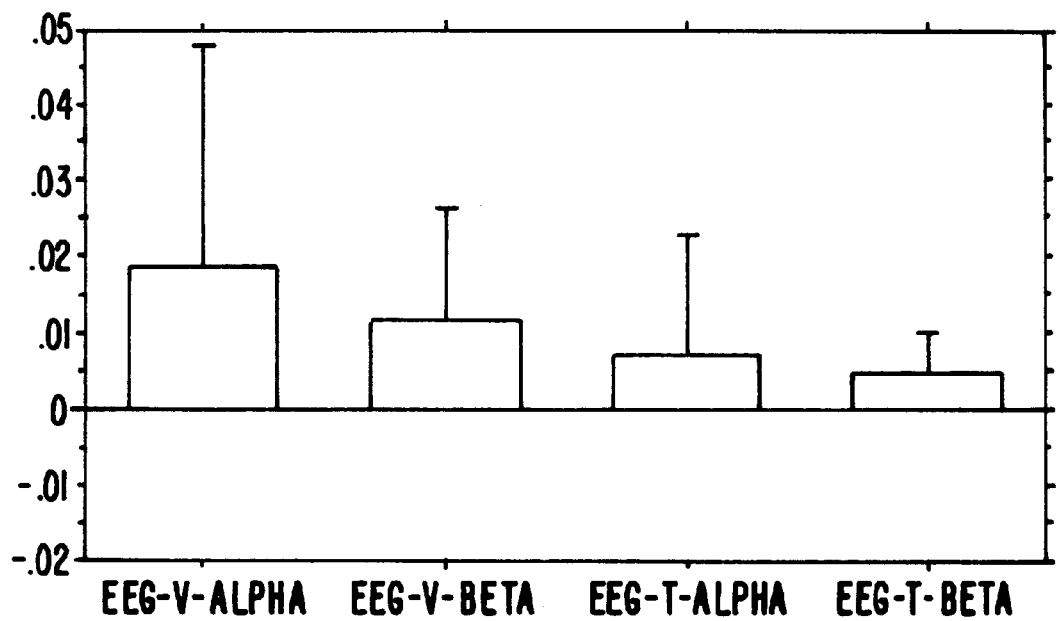
FIGS. 21A and 21B show the EEG data in men and women for androstane A3/N3.
Figure 21B:
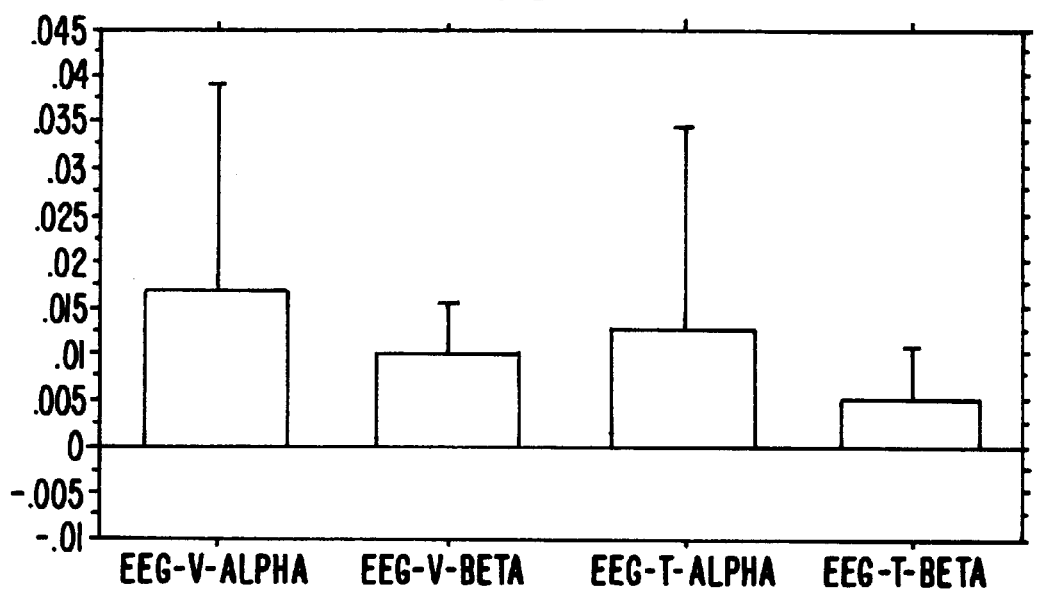
Figure 22A:
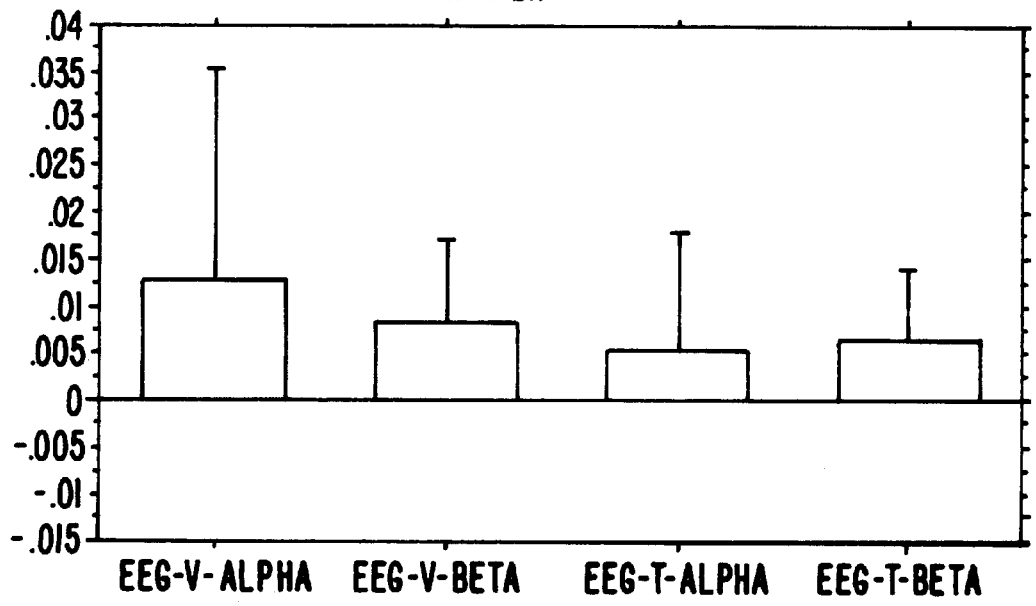
FIGS. 22A and 22B show the EEG data in men and women for androstane A13/N1.
Figure 22B:
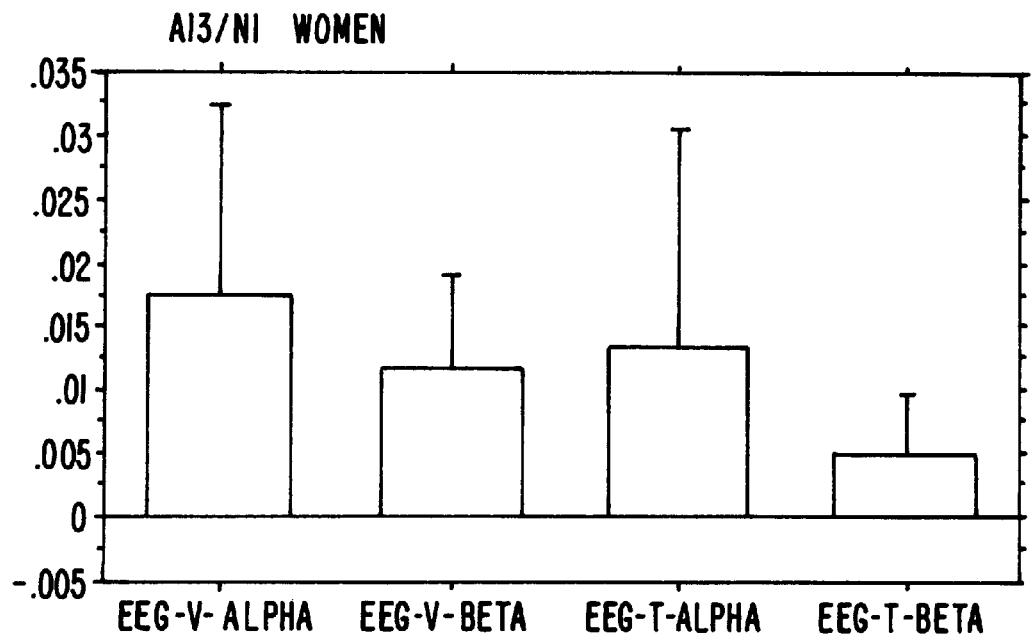
Figure 23A:
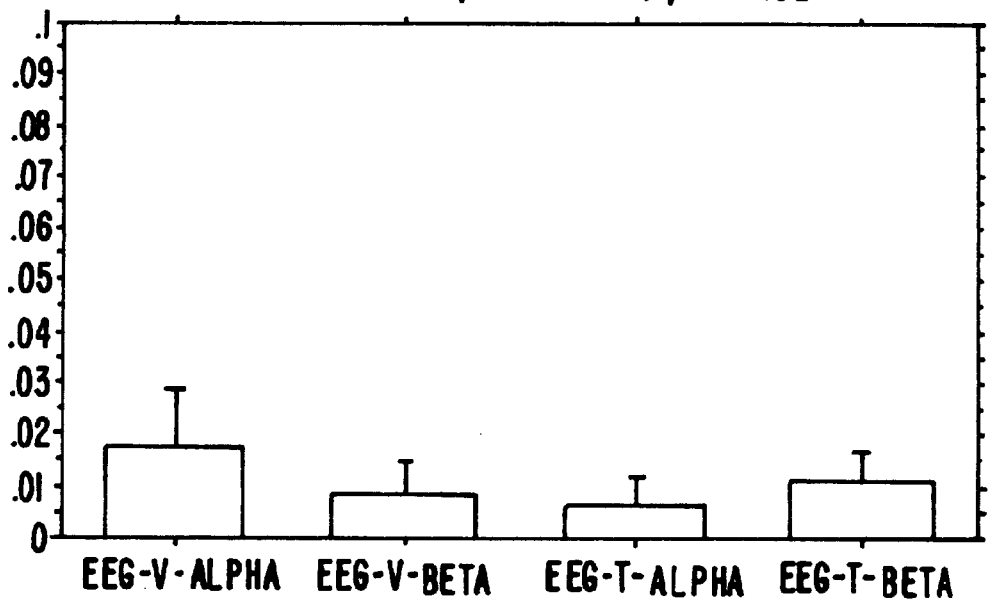
FIGS. 23A and 23B show the EEG data in men and women for androst-5,16-dien-3β,19-diol.
Figure 23B:
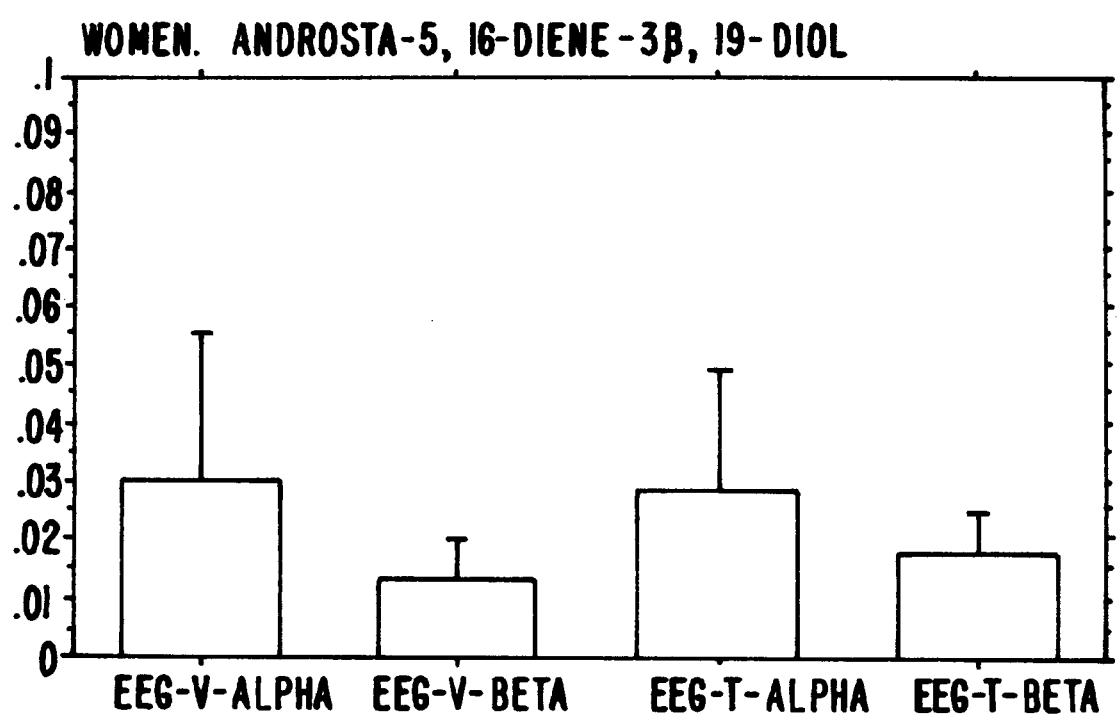
Figure 24A:
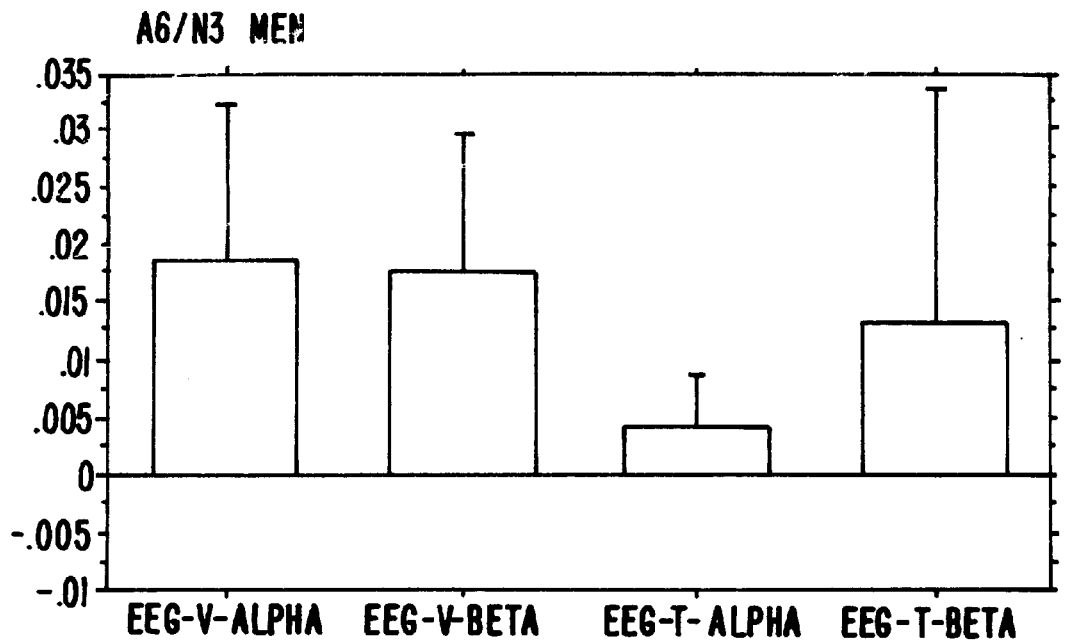
FIGS. 24A and 24B show the EEG data in men and women for androstane A6/N3.
Figure 24B:
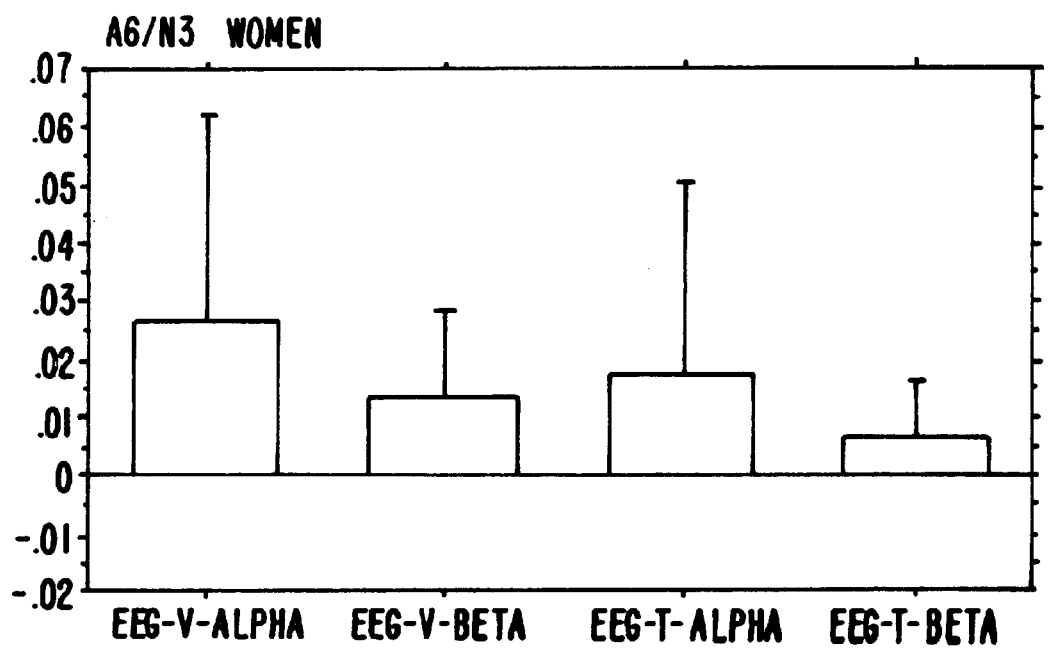

Androst-5-en-3β,19-diol-17-(p-toluenesulfonyl)hydrazone, 2:

Refer to FIG. 16. A suspension of androst-5-en-3β,19-diol-17-one (1, commercially available from Research Plus, 512.5 mg, 1.684 mmol) and p-toluenesulfonylhydrazide (p-TsNHNH$_2$, 392.1 mg, 2.105 mmol) in 2-propanol (6.0 mL) was refluxed 24 h. To the cool reaction mixture were added 20 mL of ether and the solvent was removed under reduced pressure. The residue was taken up in 10 mL of ether and the solution was filtered through diatomaceous earth. 10 mL of hexanes were added to the filtrate and the suspension was concentrated under reduced pressure. Residue was taken up in 10 mL of hot benzene and the cooled suspension was filtered. The filtrate was concentrated under reduced pressure and then flash chromatographed (40% ethyl acetate/hexanes on silica gel) to give an opaque resin (0.69 g, 1.5 mmol, 87%).
(NA-1993B-47)

Example 28

Androsta-5,16-dien-3β,19-diol, 3:

Refer to FIG. 16. A solution of androst-5-en-3β,19-diol-17-(p-toluenesulfonyl)hydrazone (2, 0.69 g, 1.5 mmol) in anh. tetrahydrofuran (THF, 35 mL) was cooled in an ice/acetone bath under argon and n-butyllithium (2.5 M in hexanes, 3.7 mL, 9.3 mmol) was added dropwise, with stirring, over the period of 1 min. The reaction mixture was stirred 4 days, during which time it was allowed to gradually warm to room temperature. The reaction was then poured into 50 mL of ice-saturated ammonium chloride and the layers were separated. The aqueous layer was extracted twice with 25 mL portions of ethyl acetate. The combined organic phases were washed with 25 mL of saturated sodium bicarbonate +25 mL of brine, dried over magnesium sulfate, and filtered through diatomaceous earth. The residue was washed with 10 mL of ethyl acetate and the combined filtrates were concentrated under reduced pressure. The residual yellow resin was flash chromatographed (50–55–60% ethyl acetate/hexanes on silica gel) and crystallized from methyl t-butyl ether/benzene to give fluffy white crystals (92.5 mg, 0.361 mmol, 24%), m.p. 169–171° C.
(NA-1993B-66)

Example 29

Electrophysiology of Androstane Stimulation of the Human VNO and Olfactory Epithelium.

A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. This electrode and delivery system has been described by Monti and Grosser (*J. Steroid Biochem. and Molec. Biol.* (1991) 39:573) and in commonly owned, copending U.S. Ser. No. 07/771,414, incorporated herein by reference. The local response of the VNO and the OE showed a correlation with the concentration of the ligand stimulus.

The study was performed on ten clinically normal (screened) volunteers—2 males and 8 females, ranging in age from 18 to 85 years. The studies were conducted without general or local anesthetics.

The catheter/electrodes were designed to deliver a localized stimulus and simultaneously record the response. In the case of VNO recording, the right nasal fosa of the subject was explored using a nasoscope (nasal specule) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then removed. In the case of the OE, recording the procedure was similar except the positioning of the catheter/electrode was gently placed deep in the lateral part of the medial nasal duct, reaching the olfactory mucosa.

Localized gaseous stimulation was done through the catheter/electrode. A constant stream of clean, nonodorous, humidified air at room temperature was continuously passed through a channel of the stimulating system. The stimulating ligand substances were diluted in propylene glycol, mixed with the humidified air, and puffed for from 1 to 2 seconds through the catheter/electrode. It is estimated that this administration provides about 25 pg of the steroid-ligand to the nasal cavity.

Figure 4A:
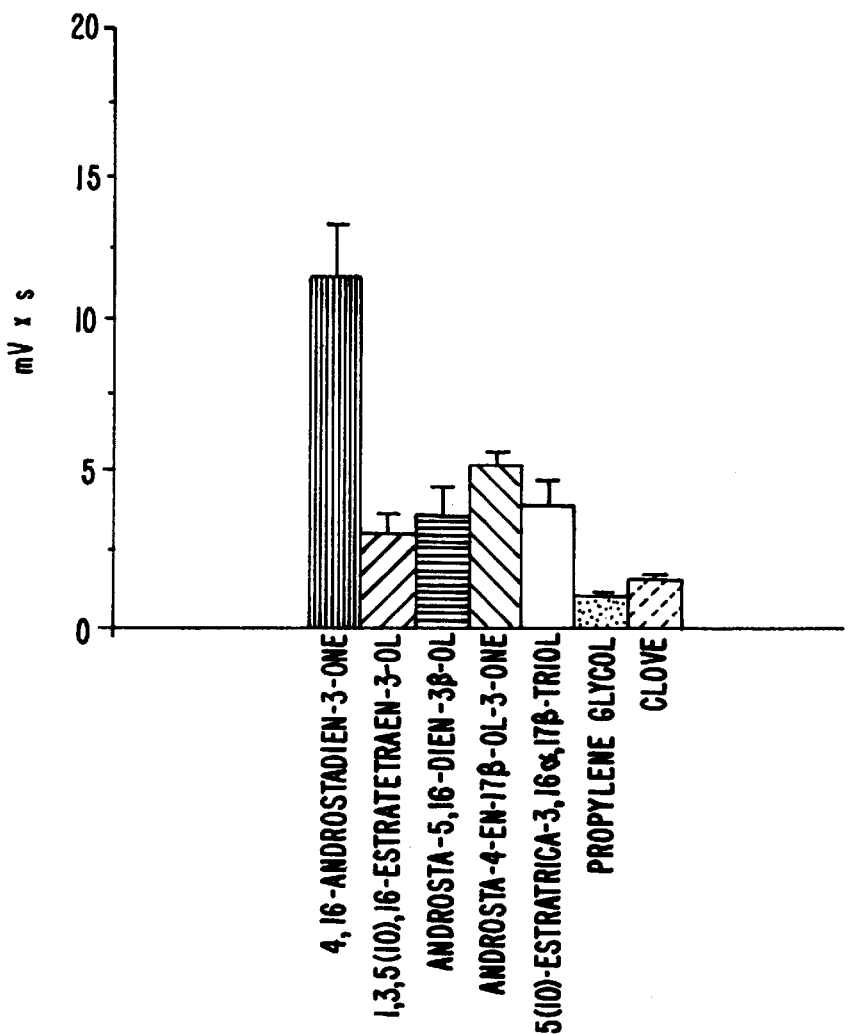
FIG. 4 is a graphic representation of the electrophysiological effect on receptor potential of the localized administration of particular steroids to the vomeronasal organ of female subjects (4A) and to the olfactory epithelium (4C).
FIG. 4B is a graphic comparison of the effect of an Androstane on the VNO receptor potential of male and female subjects.
Figure 4C:
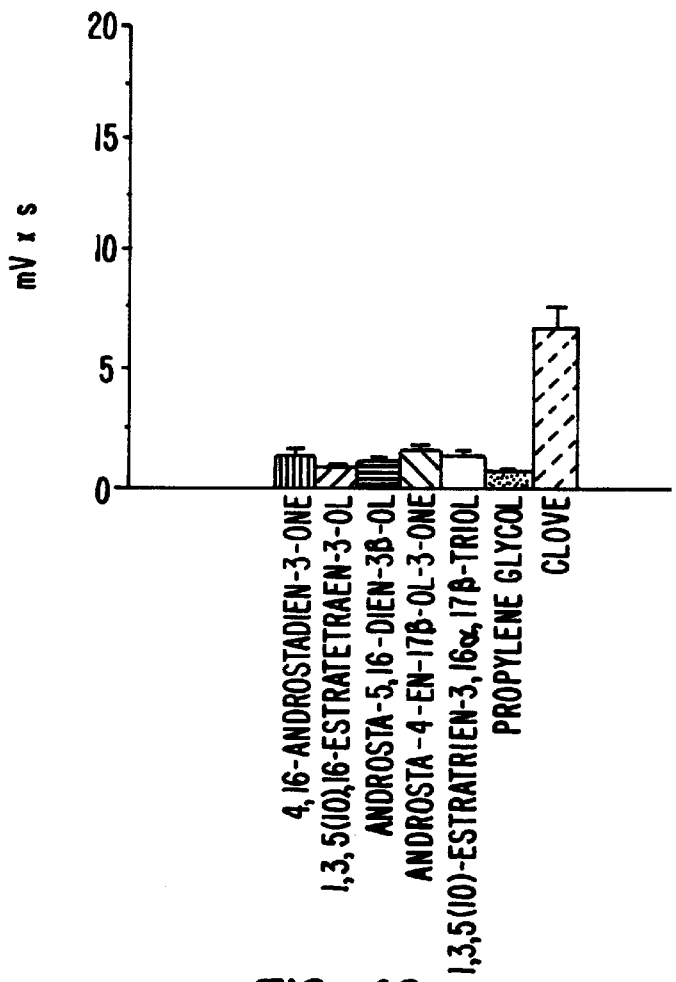
Figure 4B:
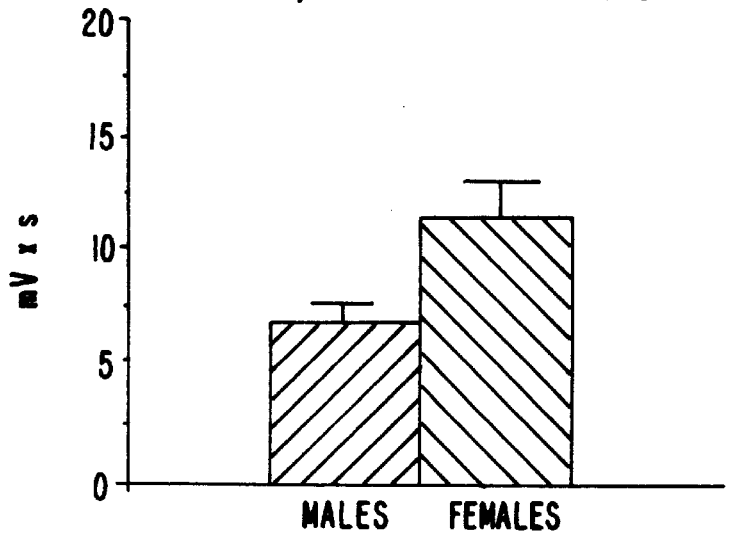

The results of this study are presented in FIGS. 4A, 4B, and 4C. The response is measured in millivolt-seconds (mV×s). Androsta-4,16-dien-3-one elicits a significantly stronger VNO response in females than do the other compounds tested (FIG. 4A). Furthermore, the VNO response to Androsta-4,16-dien-3-one is sexually dimorphic—twice as strong in females as it is in males (FIG. 4B). In contrast, the OE response in both males and females is low compared to a strong odorant such as clove (FIG. 4C).

Example 30
Measurement of the Chance in Receptor Potential of the Neuroepitihelium of the VNO in Response to Various Steroids.

Figure 5A:
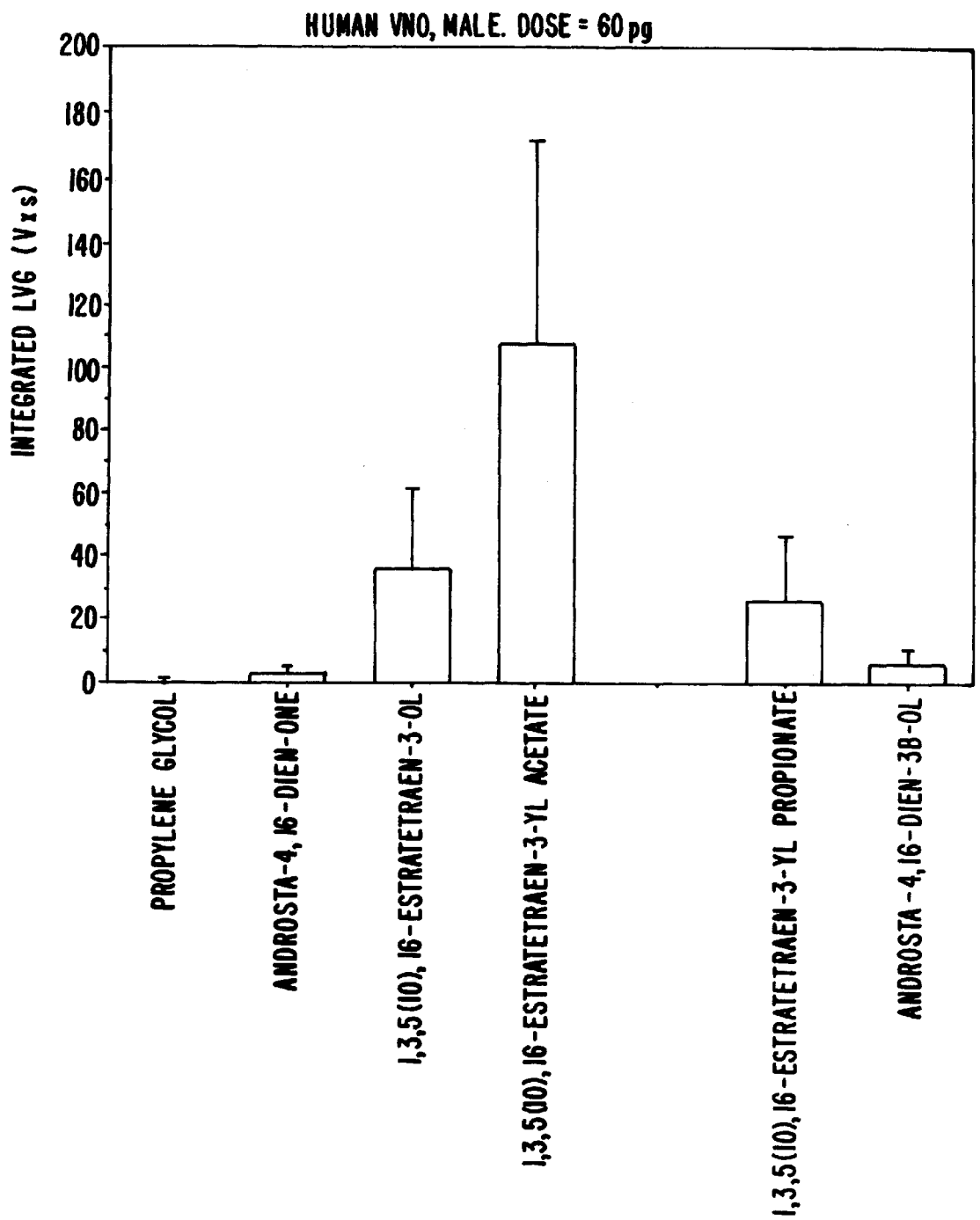
FIG. 5 is a graphic representation of the electrophysiological effect of the localized administration of particular steroids to the vomeronasal organ of male (5A) and female (5B) subjects.
Figure 5B:
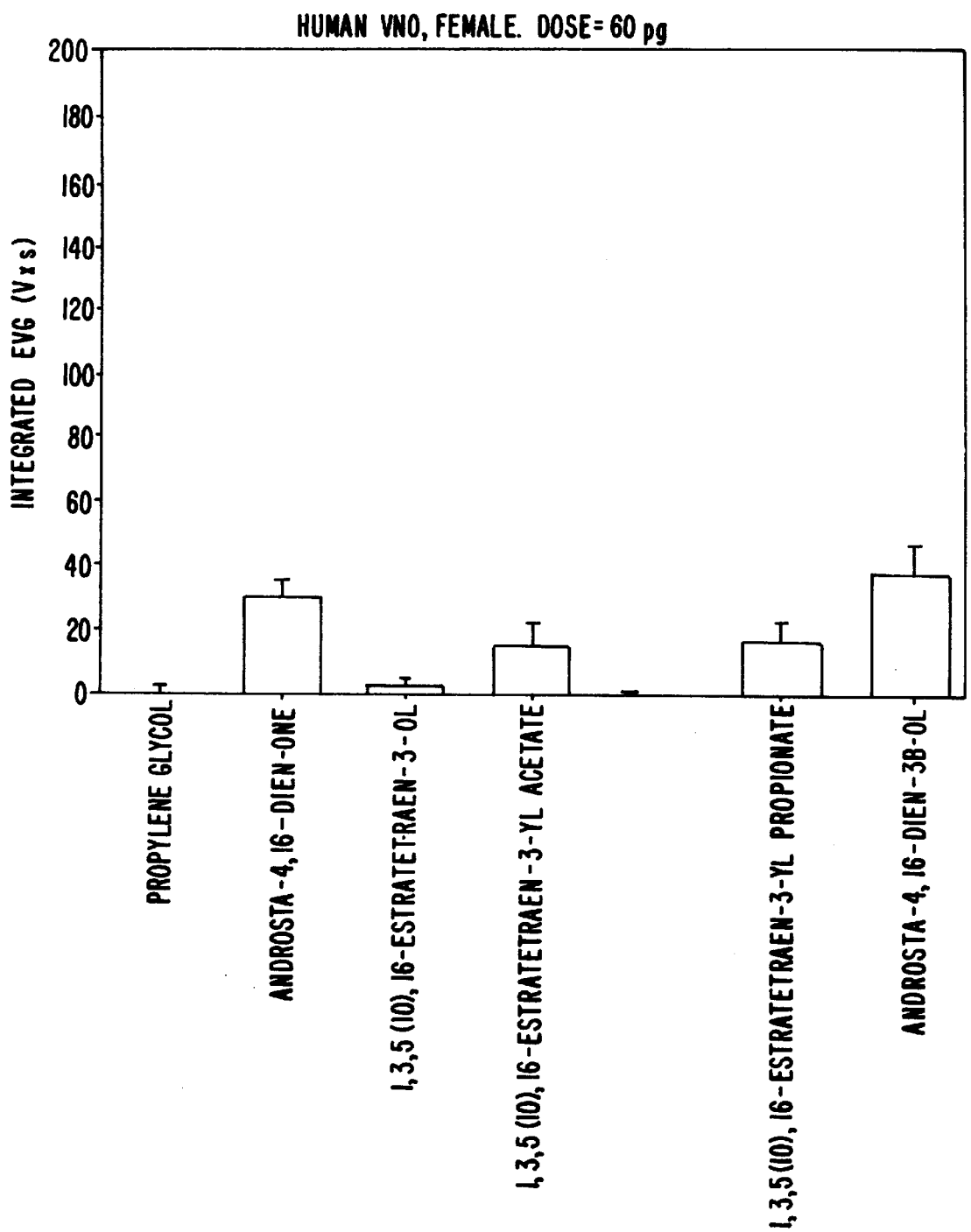
Figure 6A:
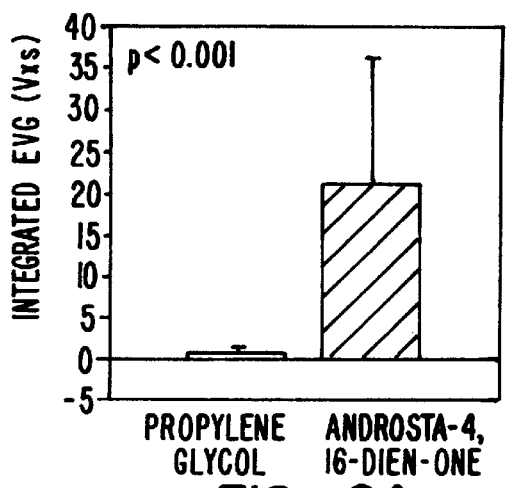
FIG. 6 depicts various autonomic responses of female subjects to an Androstane. A=receptor potential of the vomeronasal neuroepithelium; B=change in cortical alpha activity of an electroencephalogram (%); C=change in galvanic skin response (K-ohms); D=change in peripheral arterial pulse (counts/min.); E=change in skin temperature (degrees C.); and, F=change in respiratory frequency (counts/min.).
Figure 6B:
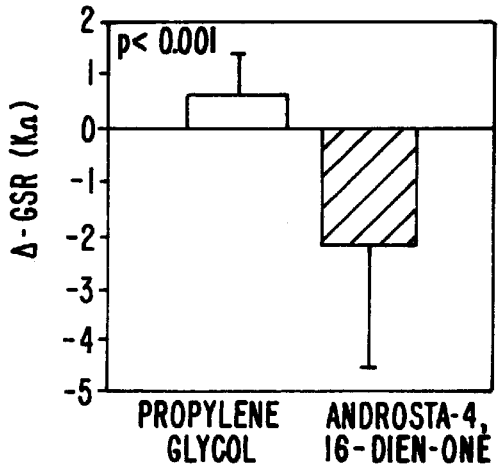
Figure 6C:
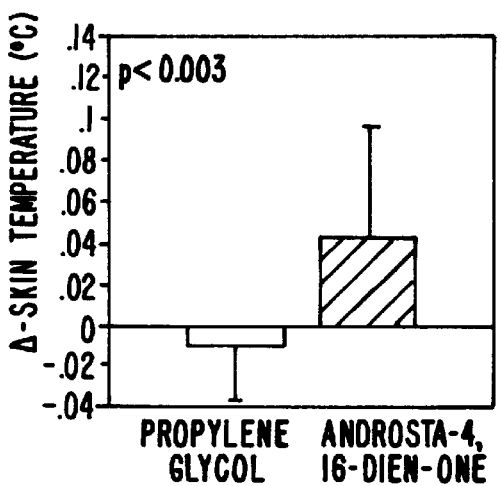
Figure 6D:
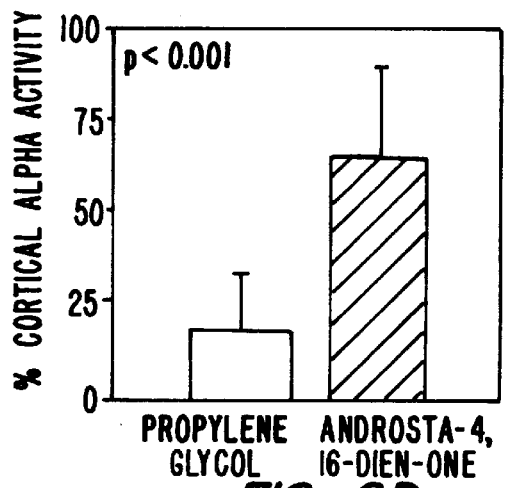
Figure 6E:
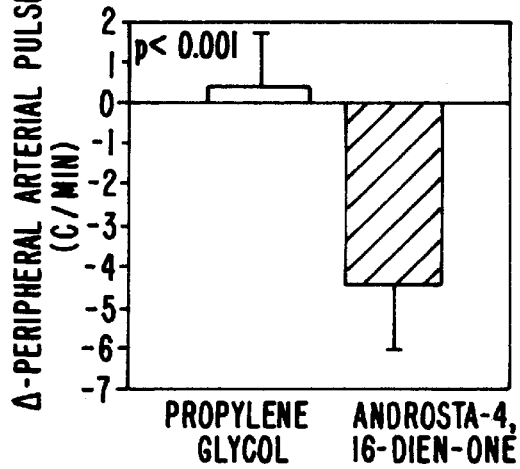
Figure 6F:
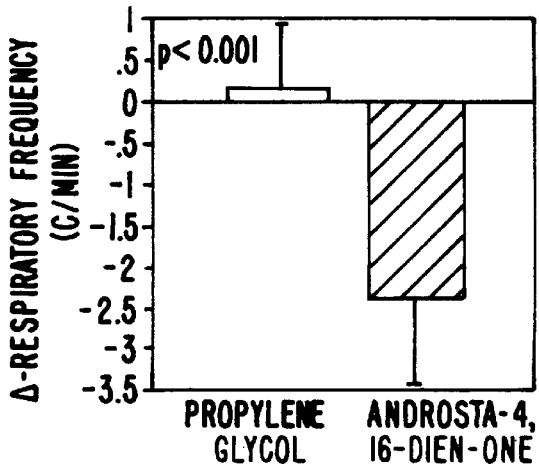

The change in receptor potential in response to five different ligands was measured in 40 female (FIG. 5A) and 40 male (FIG. 5B) subjects. Each subject was administered 60 pg of each of seven substances as indicated in the figure. The substances were administered separately for 1 second, using the procedure described in Example 10. The change in potential of the neuroepithelium of the VNO was recorded over time and the integral of the change in potential for each of the forty subjects was averaged. The results are shown in the figure. Comparison of FIGS. 5A and 5B show that each steroid is sexually dimorphic in its activity, and that some ligand substances are stronger in males while others are stronger in females.

Example 31
Measurement of Autonomic Responses to 16-Androstene Stimulation of the VNO.

Various autonomic parameters were monitored as Androsta-4,16-dien-3-one was administered to 40 female subjects using the procedure described in Example 10. Propylene glycol was also administered as a control. The ligand was administered as a 1 second pulse. The change in autonomic function was first noted within 2 seconds and lasted for up to 45 seconds. As shown in FIG. 6, when compared to a propylene glycol control, the Androstane induced a significant change in the integrated receptor potential in the VNO (6A), galvanic skin response (6B), skin temperature (6C), the percentage of cortical alpha wave activity as measured by electroencephalogram (6D), peripheral arterial pulse (6E), and respiratory frequency (6F).

Example 32
Comparison of the Chance in Receptor Potential Induced by Two Androstane Steroids.

Figure 7:
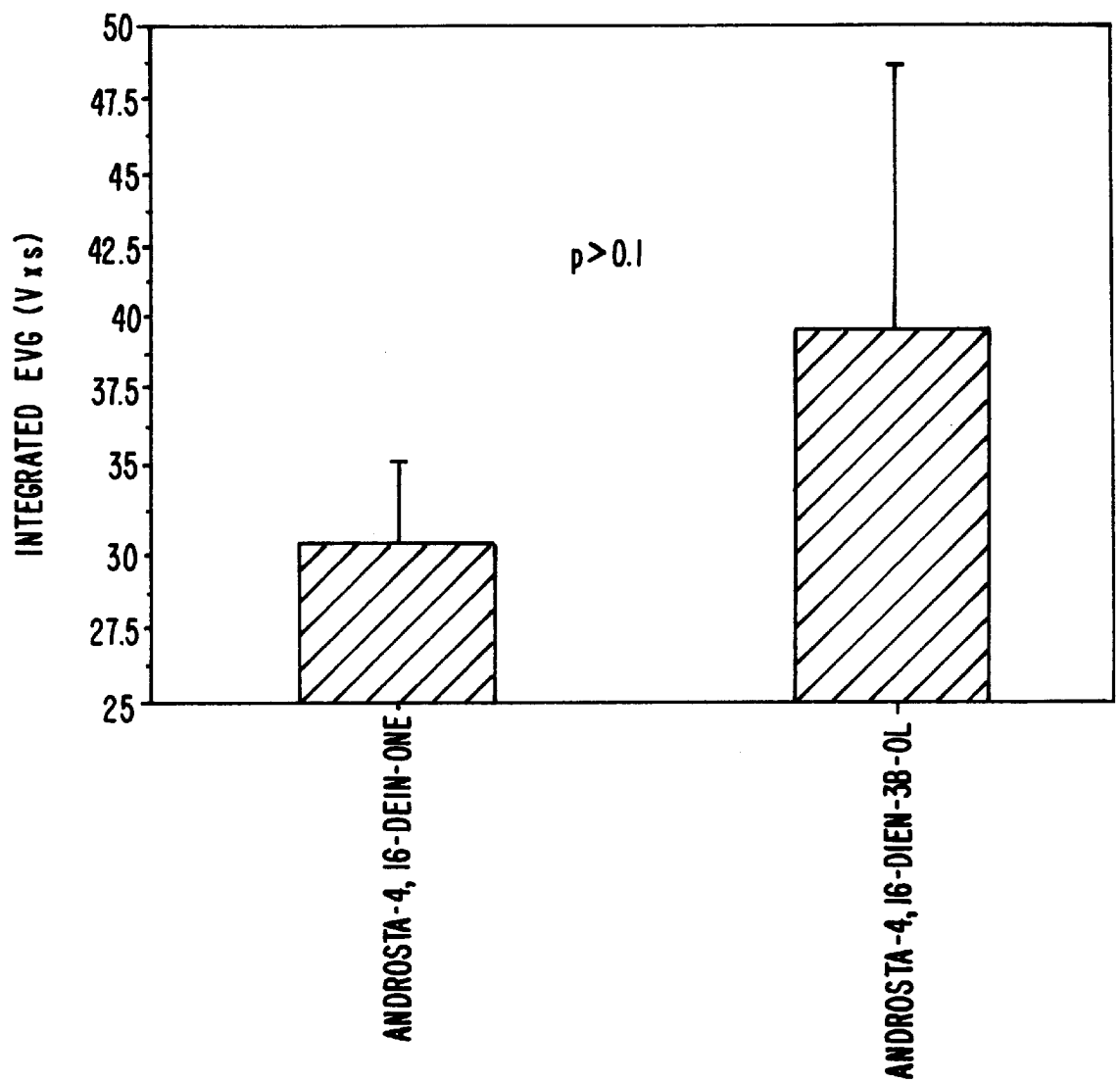
FIG. 7 depicts changes in receptor potential of the VNO after exposure of 5 females to two different Androstanes.

60 picograms of each ligand steroid and of a propylene glycol control were administered to 5 female subjects as described in Example 10. As shown in FIG. 7, Androsta-4, 16-dien-3β-ol induced a greater change in receptor potential than did Androsta-4,16-dien-3-one.

Example 33
Psychophysiological Effect of Androstane Stimulation of the VNO.

The psychophysiological effect of Androstane stimulation of the VNO was measured by the coordinate administration of pheromone and questionnaire evaluation of the subject before and after administration. The questionnaire included a panel of adjectives used as part of the standard Derogatis Sexual Inventory evaluation.

The subjects were 40 women between the ages of 20 and 45, all in good health. The women were randomly assigned—20 exposed to placebo and 20 exposed to about 20 picograms of Androsta-4,16-dien-3-one, administered as described in Example 10, supra. Subjects were given a 70 item questionnaire evaluating feeling states immediately before and 30 minutes after administration of either placebo or experimental substance. The 70 adjectives of the questionnaire were randomly administered and subsequently clustered for evaluation based on their relevance to each mood, feeling, or character trait. The results were as follows: Changes in feelings of social warmth, personal well-being, arousal/excitement, and aggression, from before administration to 30 minutes after administration, were not significant in those exposed to the 16-Androstene compared to the changes resulting from administration of the control. However, the decrease in negative affect (nervous, tense, ashamed, anxious, irritable, angry, enraged—T-test: $p<0.0001$, Anova: $p<0.04$), negative mood and character (sensitive, regretful, blameworthy, guilty, remorseful, sad, hopeless, resentful, worthless, miserable, unhappy, bitter, timid—T-test: $p<0.0004$, Anova: $p<0.06$), and overall negativity (the combination of affect and character—T-test: $p<0.0003$, Anova: $p<0.05$) were highly significant after 16-Androstene administration as compared to administration of the control.

Overall, these results suggest a sedative and/or anti-anxiety, and/or anti-depressant effect of Androsta-4, 16-dien-3-one when administered intranasally.

Example 34
Treatment of Women for Premenstrual Stress.

Women experiencing the symptoms of premenstrual stress (PMS) are provided with a pharmaceutical preparation of an Androstane steroid (preferably Androsta-4,16-dien-3-one, or Androsta-4, 16-dien-3α(β)-ol) suitable for nasal administration. The steroid is provided as an ointment at a concentration of about 1 microgram/ml and about 0.1 ml is applied. The ointment is applied just inside the nare of each nostril, three times daily. A similar method of treating PMS uses an aerosol preparation of the same steroid. The aerosol is sprayed into each nostril threes times daily.

Example 35
Electrophysiological Studies

The following electrophysiological studies were performed in 60 clinically normal human volunteers of both sexes (30 male and 30 female) whose ages ranged from 20 to 45 years. No anesthetics were used, and female subjects were excluded if pregnant.

The stimulation and recording system consists of a "multifunctional miniprobe" described elsewhere (Monti-Bloch, L. and Grosser, B. l. (1991) "Effect of putative pheromones on the electrical activity of the human vomeronasal organ and olfactory epithelium," *J. Steroid Biochem. Molec. Biol.* 39:573–582.). The recording electrode is a 0.3 mm silver ball attached to a small (0.1 mm) silver wire insulated with Teflon® the surface of the electrode is first treated to produce a silver chloride interface, and is then covered with gelatin It is positioned within a small caliber Teflon® catheter (dia=5 mm) such that the tip of the electrode protrudes approximately 2 mm. The Teflon® catheter is 10 cm in length and constitutes the terminal extension for a multichannel delivery system which delivers a continuous air stream carrying discreet pulses of chemosensory stimuli. The air stream first passes into a small chamber and is bubbled through a solution containing either a vomeropherin or an olfactant in a diluent or the diluent alone. A solenoid is used to rapidly redirect the air stream from the chamber to a route which bypasses the chamber. This creates a discreet pulse of stimulant in the air stream. A second, outer Teflon® tube with a diameter of 2 mm surrounds the catheter-electrode assemblage, and its central end is connected to an aspirator that provides continuous suction of 3 ml/s. This concentric arrangement of the outer suction tube allows the emitted chemosensory stimuli to be localized to an area we call a "minifield" (approx. dia=1 mm), and it avoids diffusion of substances either to the area outside the intended stimulation site or into the respiratory system. The entire stimulating and recording assemblage may be positioned either on the neurosensory epithelium within the VNO, or on the surface of the olfactory or respiratory epithelium.

Electro-vomeronasogram (EVG): Recordings are carried out in a quiet room with the subject supine; the multi-functional miniprobe is initially stabilized within the nasal cavity using a nasal retractor placed in the vestibule. Reference and ground electrodes consist of silver discs (8 mm), both of which are positioned on the glabella.

The entrance to the VNO, or vomeronasal pit, is identified by first dilating the nasal aperture and vestibule. A 6× magnifying binocular loupe with halogen illumination is then used to introduce the tip of the Teflon® catheter and recording electrode assemblage into the VNO opening where it is stabilized at an approximate depth of 1 mm within the vomeronasal passage. Optimal placement of the recording electrode is signaled after testing for an adequate depolarization in response to a test substance.

Electrical signals from the recording electrode are fed to a DC amplifier after which they are digitized, computer monitored, and stored. The peak-to-peak amplitude of the signals is measured, and the area under the depolarization wave is integrated, while continuously monitoring the signal both on the computer screen and on a digital oscilloscope. Artifacts produced by respiratory movements are deleted by training the subjects to practice mouth breathing with velopharyngeal closure.

Chemosensory Stimulants: Olfactory test substances are cineole, and 1-carvone; vomeropherins are A, B, C, D, E and F. Samples of vomeropherins in concentration of 25–800 fmoles are delivered in the continuous air stream for durations from 300 milliseconds to 1 second. Usually, intervals of 3 to 5 minutes separated each series of short test pulses. All components of the lines carrying the test stimuli are made of Teflon®, glass or stainless steel and are carefully cleaned and sterilized before each use.

Electro-olfactgram (EOG): Olfactory recordings employed the same stimulating and recording multifunctional miniprobe as that used for the VNO. The tip was slowly introduced until the recording electrode touched the olfactory mucosa. Adequate placement was signaled by a depolarization in response to a pulse of the odorant test substance.

Cortical evoked activity was induced by VNO stimulation with vomeropherins, and olfactory stimulation with odorants delivered in 300 ms air pulses. It was recorded using standard electroencephalographic (EEG) electrodes placed at positions Cz-A1 and Tz-A1 of the international 10120 system; the ground electrode was placed on the mastoid process. Electrodermal activity (EDA) was recorded using standard 8 mm silver electrodes in contact with palmar skin of the medial and ring fingers respectively, through a conductive gel interface. Skin temperature (ST) was recorded by a small (1.0 mm) thermistor probe placed in the right ear lobe. Peripheral arterial pulse (PAP) was monitored with a plethysmograph attached to the tip of the index finger. Respiratory frequency (RF) was measured with an adjustable strain gauge placed around the lower thorax. All electrical signals were DC amplified, digitized (MP-100, Biopac Systems) and continuously monitored utilizing a computer. Statistical Analysis: EVGs or EOGS, peak-to-peak changes and frequency changes of other parameters were measured and statistically analyzed. The significance of the results was determined by either using paired t-tests or analysis of variance (ANOVA).

Figure 8A:
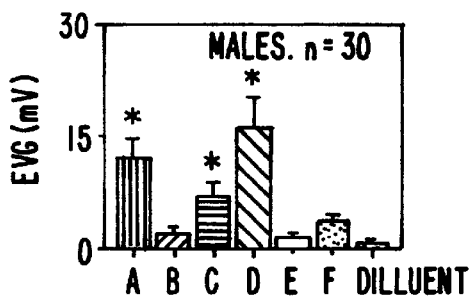
FIGS. 8A & B: EVG responses were measured as described in male (A) and female (B) subjects.
Figure 8C:
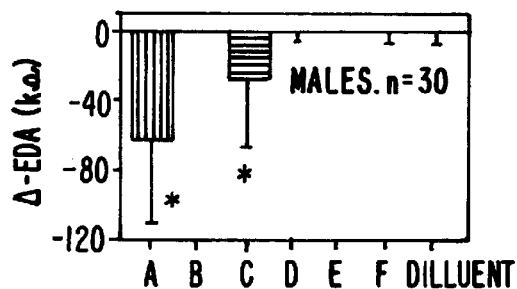
FIGS. 8C & D: Electrodermal activity was measured as described. Changes (measured in xΩ) in response due to delivery of vomeropherins to the VNO of each subject are shown in male (C) and female (D) subjects.
Figure 8B:
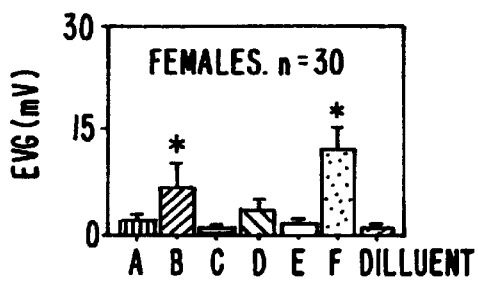
FIG. 8 depicts sexual dimorphism in local and autonomic responses to the stimulation of the VNO with vomeropherins. Various vomeropherins (200 fmoles) and the diluent control were administered to 30 male and 30 female subjects (ages 20 to 45) as described. Bars indicate the mean response of the population.
FIGS. 8E & F: Alpha-cortical activity was measured as described. Changes in response due to delivery of vomeropherins to the VNO of male (E) and female (F) subjects.
FIGS. 8G & H: Skin temperature (ST) was measured as described. Changes in response due to delivery of vomeropherins to the VNO of each subject are shown in male (G) and female (H) subjects.
The Compounds in the graphs are:
A=1, 3, 5(10),16-Estratetraen-3-yl acetate
B=Androsta-4,16-dien-3-one
C=1,3,5(10),16-Estratetraen-3-ol
D=3-Methoxy-Estra-1,3,5(10),16-tetraene
E=Androsta-4,16-dien-3α-ol
F=Androsta-4,16-dien-3β-ol
Figure 8D:
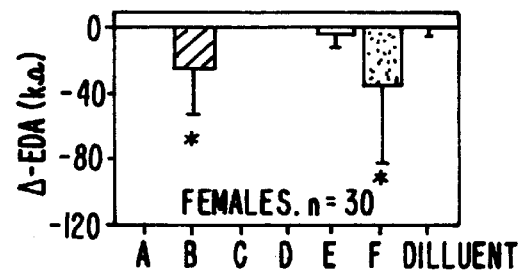
Figure 8E:
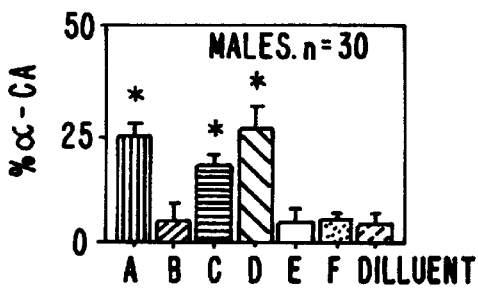

Effect of Vomeropherins on the EVG: Each of the vomeropherins was found to produce a sexually dimorphic receptor potential (FIGS. 8A–B). Recordings of the EVG were performed on 30 men and 30 women (ages 20 to 45). Vomeropherins were diluted and applied as 1 second pulses to the VNO with b minute intervals between pulses when questioned, the subjects were not able to "smell" or otherwise consciously detect any of the vomeropherins. This finding is in agreement with results previously reported (Monti-Bloch, L. and Grosser, B. l. (1991) "Effect of putative pheromones on the electrical activity of the human vomeronasal organ and olfactory epithelium," *J. Steroid Biochem. Molec. Biol.* 39:573–582.) which indicated that neither olfactory nor vomeropherin test stimuli delivered to the VNO elicit a perceptible sensation at the delivered concentration.

FIG. 8A shows the average response of male subjects (ages 20 to 38) to the diluent, and to equimolar quantities (100 fmoles) of five vomeropherins (A, B, C, D and F), and to E, a stereoisomer of F. The profile of the response to each of the substances was similar in all subjects regardless of age, and no significant differences were revealed either by t-tests or by analysis of variance. For example, A, C and D produced significant effects ($M_{15}$=11.4 mV, SD=3.6 mV; $M_{76}$=6.4 mV, SD 2.5 mV, and $M_{84}$=15.1 mV, SD=4.9 mV; $p<0.01$), that were consistent in all individual cases. Other vomeropherins depolarized the VNO-receptors to a much lesser extent, but with consistent mean response amplitudes from individual to individual. Vomeropherins active in male subjects produced larger responses than the diluent ($p<0.001$). B, F and similar concentrations of olfactants induced significantly reduced responses in the male VNO (FIG. 8A and FIG. 9).

A similar experimental protocol was followed with the 30 female subjects (ages 20–45). Among the vomeropherins, F (100 fmoles) produced the most significant differences within the group (FIG. 8B). Here, A induced a small effect that was significantly different from F (p<0.01). In both populations of subjects, active vomeropherins induced receptor responses having large standard deviations (FIG. 8). When the frequency distribution of the effects of A and F was studied in males and females respectively, we found a bimodal distribution. The significance of this observation is being studied at this point.

E, a stereoisomer of F, does not stimulate the VNO in female subjects while F does (FIG. 8B). This is a demonstration of the specificity of VNO recognition of vomeropherins. In this regard it is interesting to note that while F is a superior vomeropherin, E generates a stronger olfactory effect than does F (FIG. 8B and FIG. 9).

Figure 9A:
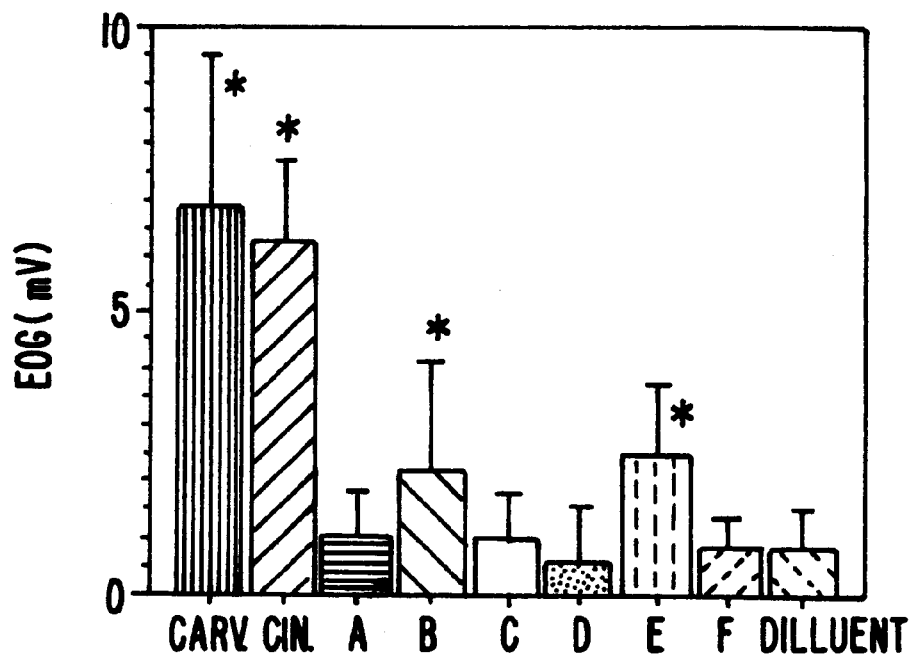
FIG. 9 depicts electro-olfactgrams of male and female subjects induced by stimulation of the OE with olfactants and vomeropherins A: 400 fmoles of the olfactants 1-carvone and cineole as well as 200 fmoles of the vomeropherins A, B, C, D and F; and the stereoisomer E were applied separately as one second pulses to the OE of 20 subjects (both male and female) and each EOG response was recorded as described. The olfactants as well as E and B produced significant (p<0.01) local response. B: 400 fmoles of the olfactants 1-carvone and cineole do not induce a significant EVG response when delivered to the VNO of male and female subjects.

Effects of Vomeropherins on the EOG: The summated receptor potential from the olfactory epithelium (OE) was recorded in 20 subjects: 10 males and 10 females. In contrast to the sensitivity of the VNO to vomeropherins, the OE is less sensitive to these substances. This is true for both males and females (FIG. 9A). The mean receptor potential amplitude ranged from 2.3 mV to 0.78 mV. In this study, B was the only vomeropherin having significant effect in the OE (p<0.02). Of the subjects questioned about odorant sensations following each stimulus presentation, 16 reported no olfactory sensation, while three males and one female described B as an unpleasant odor. This finding reveals that at the concentrations used in our study, most vomeropherins are not effective stimulants of the olfactory receptors, but do have a clear effect on vomeronasal receptors.

Figure 9B:
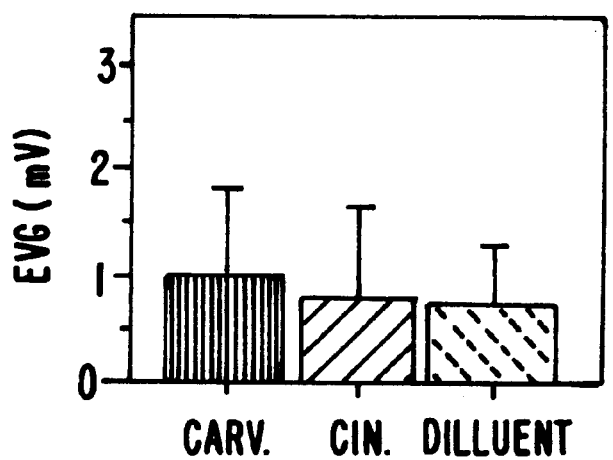
Figure 10A:
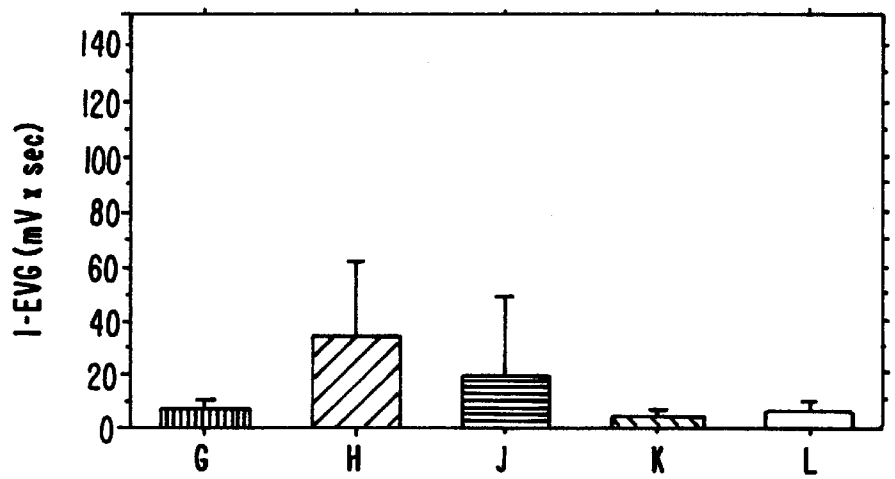
FIG. 10 depicts the electrophysiological effect of the following vomeropherins on the vomeronasal organ of 20 female subjects:
G=Androst-4-en-3-one
H=Androsta-4,16-diene-3,6-dione
J=10,17-Dimethylgona-4,13(17)-dien-3-one
K=1,3,5(10),16-Estratetraen-3-ol-methyl ether
L=1,3,5(10),16-Estratetraen-3-yl-propionate
EVG=Electro-vomeronasogram
GSR=Galvanic Skin Response
=Electrodermal Activity, EDA
ST=Skin Temperature
Figure 10B:
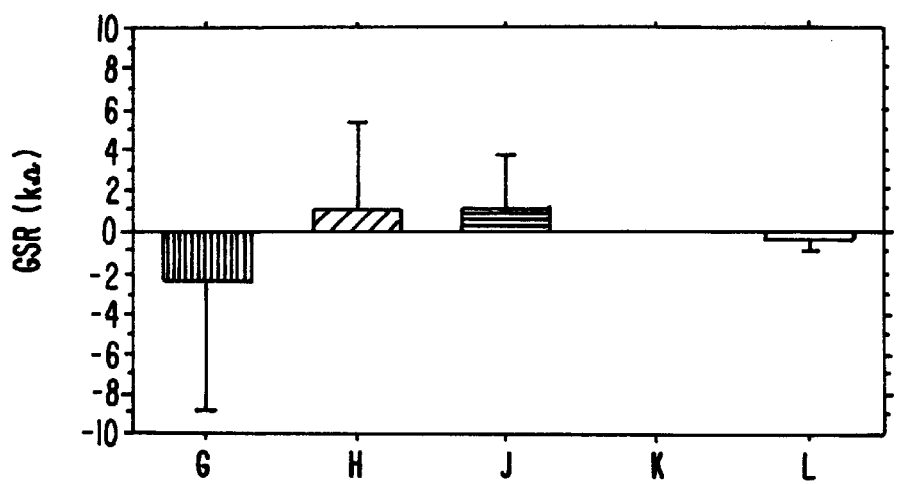
Figure 10C:
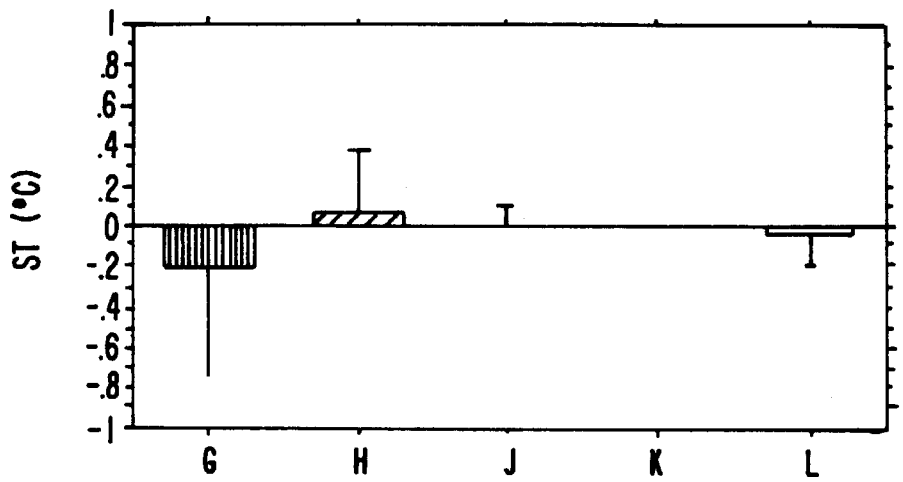
Figure 11A:
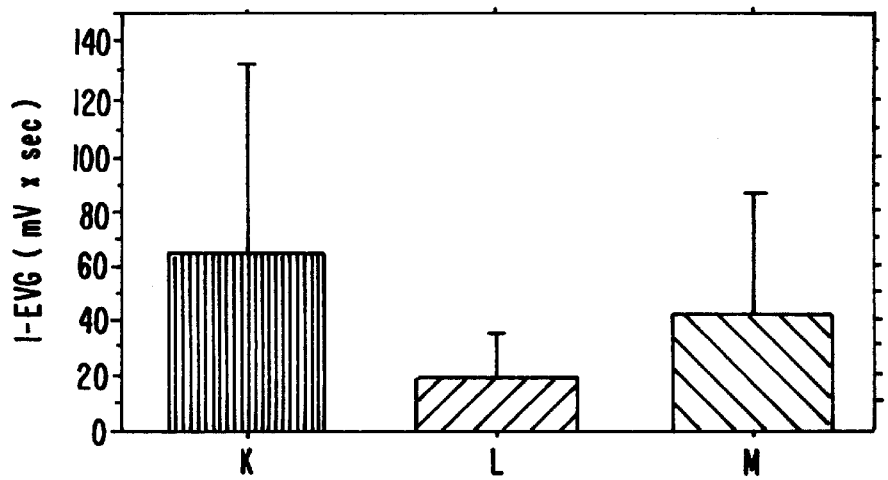
FIG. 11 depicts the electrophysiological effect of vomeropherins on the vomeronasal organ of 20 male subjects.
M=1,3,5(10)-Estratrien-3-ol
Figure 11B:
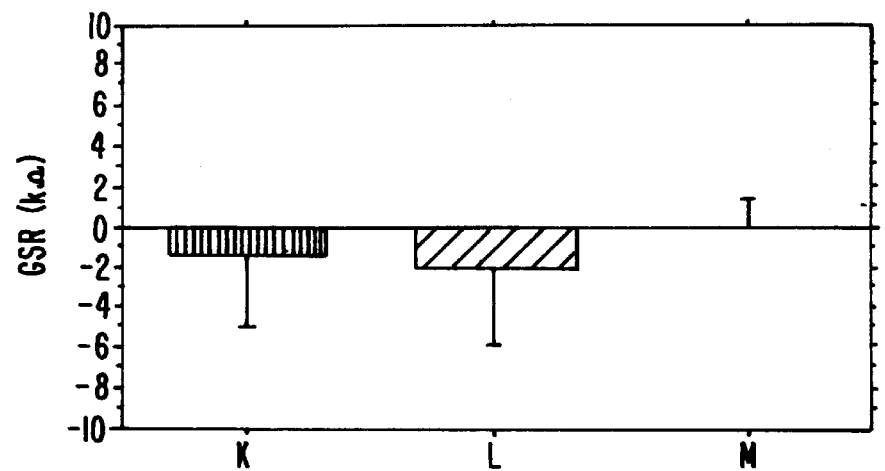
Figure 11C:
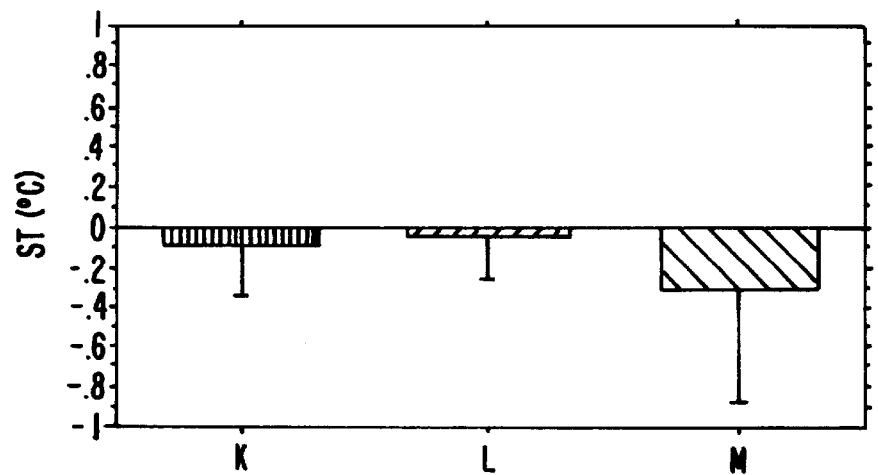

Effects of Olfactants on the EVG and EOG: In contrast to vomeropherins, the olfactants 1-carvone and cineole produce only a minor local response in the VNO (FIG. 9B). This was true for both men and women. As expected, these olfactants produced a strong response in both men and women (p<0.01) when locally applied to the OE (FIG. 9A). The diluent depolarized olfactory receptors to a lesser extent than cineole or 1-carvone (p<0.01), and it did not produce an olfactory sensation.

Reflex Effects of Vomeropherins: Studies were conducted to determine the central nervous system (CNS) reflex responses to vomeropherin stimulation of the VNO. The sexually dimorphic local responses induced by vomeropherins (FIGS. 8A and B) were mirrored in the autonomic response of male & female subjects. In male subjects (FIG. 8C), A and C decreased skin resistance (electrodermal activity=EDA) (p<0.01, n=30). In female subjects. (FIG. 8B), F and B produced greater decrease in EDA than A or C (p<0.01, n=30).

Vomeropherins A and C induced a significant increase in skin temperature (ST) (FIG. 8G) in 30 male subjects (p<0.01); however D induced significant temperature decrease (p<0.01). In 30 female subjects (FIG. 8H) B and F evoked a significant increase in skin temperature (ST) (p<0.01) compared to A and C. In female subjects vomeropherins produced changes in EDA and ST with a greater standard deviation than in males.

Figure 8G:
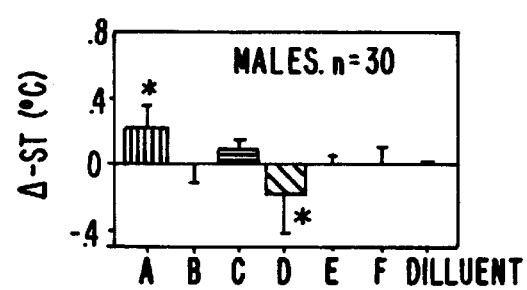
Figure 8F:
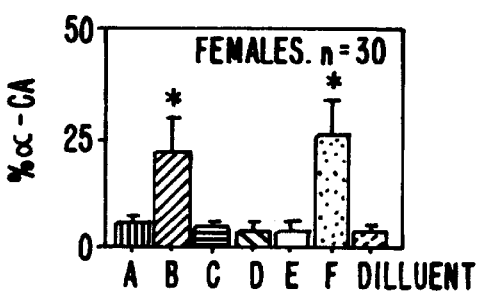
Figure 8H:
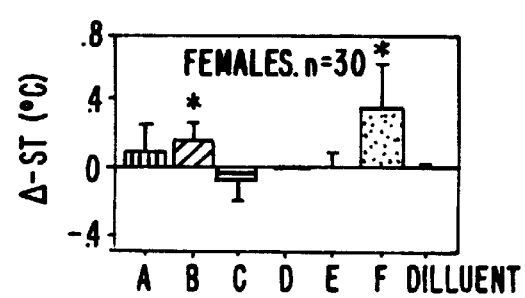

Cortical activity was recorded from Cz and Tz in male and female subjects during application to the VNO of air pulses (300 ms to 1 sec) containing 200 fmoles of vomeropherin (FIG. 8G and H). In males (FIG. 8E) A, C and D significantly increased alpha cortical activity with a latency of 270–380 ms. D and A evoked the strongest effect (p<0.01). Synchronization of the EEG was sustained for 1.5 to 2.7 minutes after application of a single pulse of active substance. In females (FIG. 8F), a single pulse (200 fmoles) of B or F applied to the VNO increased alpha cortical independent of the response of olfactory receptors. We found characteristic specificities in the response of the human VNO and the olfactory epithelium which suggests that they are independent functional systems with separate connections to the CNS (Brookover, C. (1914) The nervus terminalis in adult man. J. Comp. Neurol. 24:131–135.) There is also preliminary evidence that the EVG is not associated with trigeminal nociceptor endings since application of a local anesthetic (2% lidocaine) to the respiratory epithelium of the nasal septum neither blocks nor diminishes the EVG (Monti-Bloch, L. and Grosser, B. 1. (1991) "Effect of putative pheromones on the electrical activity of the human vomeronasal organ and olfactory epithelium," *J. Steroid Biochem. Molec. Biol.* 39:573–582.), also, subjects failed to report sensations of pain as a consequence of any of the stimulation procedures.

Additional tests we conducted using androsta-5,16-diene-3β,19-diol and four other androstanes, identified by their positions on the chart. The results are shown in FIGS. 17 through 24. The EEG, RF and EKG response for androsta-5,16-diene-3β,19-diol is stronger in females compared to males, while the ST, GSR and EVG response is stronger in males. Some females to whom were administered the compound reported feelings of happiness, which is unusual in that such reports are normally accompanied by much higher RF and GSR data than shown in FIGS. 18B and 18C.

VNO receptors are clearly more sensitive to vomeropherins than to any of the olfactants tested; the opposite is true for olfactory receptors. While the OE may have receptor sites for some vomeropherins, the response specificity of the VNO is clearly different.

Sexual differences were noted in the specificities and effects of two groups of vomeropherins, A, C and D; and B and F. This suggests a possible receptor-related sexual dimorphism. The findings suggest the activation of components of the autonomic nervous system in the adult human by vomeropherin stimulation of the VNO.

Furthermore, the results suggest that stimulation of the VNO with vomeropherins produces synchronization of the EEG (FIGS. 8G and H) Thus, the evidence herein indicates that the vomeronasal system responds to a variety of chemosensory stimuli, and that some are able to induce reflex autonomic activity.

We claim:

1. A compound of the formula:

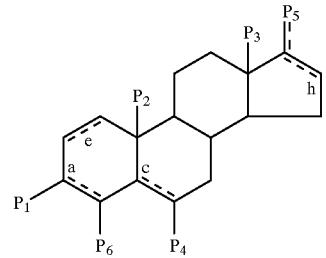

wherein $P_1$ is α-(β-) hydroxy; $P_2$ is hydroxymethyl; $P_3$ is selected from the group consisting of hydrogen, methyl, hydroxymethyl, acyloxymethyl, alkoxymethyl, lower alkyl, hydroxyalkyl, acyloxyalkyl, and alkoxylalkyl; $P_4$ is selected from the group consisting of hydrogen, halo, hydroxy, alkoxy, and acyloxy; $P_5$ is selected from the group consisting of a hydrogen atom, a methyl, and a halogen atom; $P_6$ is hydrogen or halo; "c" and "h" are double bonds; and "a" and "e", are alternative sites for optional double bonds; with the proviso that;

I: if $P_3$ is a methyl group, $P_5$ is hydrogen, then
(a) $P_4$ cannot be hydrogen if $P_1$ is β-hydroxy and "a" and "e" are absent.

2. A compound of the formula:

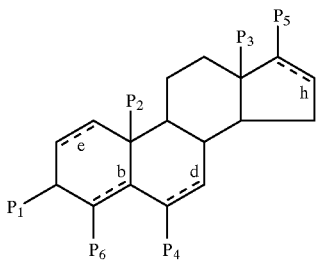

wherein $P_1$ is oxo; $P_2$ is selected from the group consisting of methyl, hydroxymethyl, acyloxymethyl, alkoxymethyl, lower alkyl, hydroxyalkyl, acyloxyalkyl, and alkoxylalkyl; $P_3$ is selected from the group consisting of hydrogen, methyl, hydroxymethyl, acyloxymethyl, alkoxymethyl, lower alkyl, hydroxyalkyl, acyloxyalkyl, and alkoxylalkyl; $P_4$ is hydroxy; $P_5$ is selected from the group consisting of a hydrogen atom, a methyl, and a halogen atom; $P_6$ is hydrogen or halo; "b" and "h" are double bonds; and "d", and "e", are alternative sites for optional double bonds; with the proviso that:

I: if $P_3$ is a methyl group, $P_5$ is hydrogen, then
(a) "d" cannot be present if "e" is absent.

3. A compound selected from the group consisting of:
17-METHYLENEANDROST-4-EN-3α-OL;
17-METHYLENEANDROST-4-EN-3β-OL;
6β-HYDROXYANDROSTA-4,16-DIEN-3-ONE;
6β-HYDROXY-17-METHYL-18-NORANDROSTA-4,13(17)-DIEN-3-ONE;
ANDROSTA-5,16-DIEN-3β,19-DIOL;
17-METHYLENEANDROST-4-ENE-3,6-DIONE;
17-METHYL-18-NORANDROSTA-4,13(17)-DIEN-3α-OL;
17-METHYL-18-NORANROSTA-4,13(17)-DIEN-3β-OL;
17β-METHYLANDROST-4-ENE-3,6-DIONE;
3-METHOXY-17-METHYLENEANDROSTA-3,5-DIENE;
6β-HYDROXY-17-METHYLENEANDROST-4-EN-3-ONE;
17-METHYLENEANDROSTA-1,4-DIEN-3-ONE;
6β-HYDROXYANDROSTA-1,4,16-TRIEN-3-ONE;
6β-HYDROXY-17-METHYLENEANDROSTA-1,4-DIEN-3-ONE;
17β-METHYLANDROST-4 -EN-3α-OL;
17β-METHYLANDROST-4-EN-3β-OL; and
3-METHOXY-17-METHYL-18-NORANDROSTA-3,5,13(17)-TRIENE.

4. A compound according to claim 1 wherein P1 is β-hydroxy.

5. A compound of claim 3 wherein the compound is 17-methyleneandrost-4-en-3α-ol.

6. A compound of claim 3 wherein the compound is 17-methyleneandrost-4-en-3β-ol.

7. A compound of claim 3 wherein the compound is androsta-5,16-diene-3β,19-diol.

* * * * *

UNITED STATES PATENT AND TRADEMARK OFFICE
CERTIFICATE OF CORRECTION

PATENT NO.   : 5,969,168
DATED        : Oct. 19, 1999
INVENTOR(S)  : Berliner et al.

It is certified that error appears in the above-identified patent and that said Letters Patent is hereby corrected as shown below:

Claim 3, at column 46, line 7 "NORANROSTA" should read -- NORANDROSTA --.

Signed and Sealed this

Twelfth Day of September, 2000

Attest:

Q. TODD DICKINSON

*Attesting Officer*     *Director of Patents and Trademarks*